United States Patent
Cosentino et al.

(10) Patent No.: US 7,577,475 B2
(45) Date of Patent: Aug. 18, 2009

(54) SYSTEM, METHOD, AND APPARATUS FOR COMBINING INFORMATION FROM AN IMPLANTED DEVICE WITH INFORMATION FROM A PATIENT MONITORING APPARATUS

(75) Inventors: Daniel L. Cosentino, Chaska, MN (US); Louis C. Cosentino, Excelsior, MN (US)

(73) Assignee: Cardiocom, Chanhassen, MN (US)

( * ) Notice: Subject to any disclaimer, the term of this patent is extended or adjusted under 35 U.S.C. 154(b) by 207 days.

(21) Appl. No.: 11/230,810

(22) Filed: Sep. 19, 2005

(65) Prior Publication Data

US 2006/0064030 A1 Mar. 23, 2006

Related U.S. Application Data

(63) Continuation-in-part of application No. 11/181,682, filed on Jul. 13, 2005, which is a continuation-in-part of application No. 10/746,325, filed on Dec. 23, 2003, which is a continuation-in-part of application No. 10/093,948, filed on Mar. 7, 2002, which is a continuation-in-part of application No. 09/949,197, filed on Sep. 7, 2001, now Pat. No. 6,755,783, which is a continuation-in-part of application No. 09/293,619, filed on Apr. 16, 1999, now Pat. No. 6,290,646.

(51) Int. Cl.
*A61B 5/04* (2006.01)

(52) U.S. Cl. .................... 600/509; 600/508

(58) Field of Classification Search ............... 600/508, 600/509; 607/6, 17–19; 705/2, 30
See application file for complete search history.

(56) References Cited

U.S. PATENT DOCUMENTS

| 3,743,040 | A | 7/1973 | Cosentino et al. |
| 3,925,762 | A | 12/1975 | Heitlinger et al. |
| 4,531,527 | A | 7/1985 | Reinhold, Jr. et al. |
| RE32,361 | E | 2/1987 | Duggan |

(Continued)

FOREIGN PATENT DOCUMENTS

DE 43 35 869 A 1 10/1994

(Continued)

OTHER PUBLICATIONS

"Technology to Help Meet Standards and Reduce Costs", Alere Medical Incorporated, 6 pages (1998).

(Continued)

*Primary Examiner*—Carl H Layno
*Assistant Examiner*—Brian T Gedeon
(74) *Attorney, Agent, or Firm*—Merchant & Gould P.C.

(57) ABSTRACT

A data set is generated by an implanted medical device, during operation of the device. The data set includes data characterizing various physiological states of the patient. The data set is communicated from the device to a patient monitoring apparatus. The patient monitoring apparatus develops its own data set by posing questions to the patient, and optionally by measuring a physiological parameter of the patient, such as weight. The two data sets are combined and are analyzed to determine medical information concerning the patient, such as impending decompensation of heart failure.

13 Claims, 43 Drawing Sheets

U.S. PATENT DOCUMENTS

| | | | |
|---|---|---|---|
| 4,712,562 A | 12/1987 | Ohayon et al. | |
| 4,803,625 A | 2/1989 | Fu et al. | |
| 4,838,275 A | 6/1989 | Lee | |
| 4,899,758 A | 2/1990 | Finkelstein et al. | |
| 4,947,858 A | 8/1990 | Smith | |
| 5,012,411 A | 4/1991 | Policastro et al. | |
| 5,054,493 A | 10/1991 | Cohn et al. | |
| 5,092,330 A | 3/1992 | Duggan | |
| 5,113,869 A | 5/1992 | Nappholz et al. | |
| 5,241,966 A | 9/1993 | Finkelstein et al. | |
| 5,307,263 A | 4/1994 | Brown | |
| 5,331,549 A | 7/1994 | Crawford, Jr. | |
| 5,390,238 A | 2/1995 | Kirk et al. | |
| 5,402,794 A | 4/1995 | Wahlstrand et al. | |
| 5,406,955 A | 4/1995 | Bledsoe et al. | |
| 5,434,611 A | 7/1995 | Tamura | |
| 5,437,285 A | 8/1995 | Verrier et al. | |
| 5,441,047 A | 8/1995 | David et al. | |
| 5,522,396 A | 6/1996 | Langer et al. | |
| 5,553,609 A | 9/1996 | Chen et al. | |
| 5,553,623 A | 9/1996 | Ochs | |
| 5,560,370 A | 10/1996 | Verrier et al. | |
| 5,584,868 A | 12/1996 | Salo et al. | |
| 5,594,638 A | 1/1997 | Iliff | |
| 5,635,060 A | 6/1997 | Hagen et al. | |
| 5,660,176 A | 8/1997 | Iliff | |
| 5,687,717 A | 11/1997 | Halpern et al. | |
| 5,704,366 A | 1/1998 | Tacklind et al. | |
| 5,711,297 A | 1/1998 | Iliff | |
| 5,724,032 A | 3/1998 | Klein et al. | |
| 5,724,968 A | 3/1998 | Iliff | |
| 5,725,559 A | 3/1998 | Alt et al. | |
| 5,743,267 A | 4/1998 | Nikolic et al. | |
| 5,758,652 A | 6/1998 | Nikolic | |
| 5,778,882 A | 7/1998 | Raymond et al. | |
| 5,822,715 A | 10/1998 | Worthington et al. | |
| 5,828,943 A | 10/1998 | Brown | |
| 5,832,448 A | 11/1998 | Brown | |
| 5,839,438 A | 11/1998 | Graettinger et al. | |
| 5,842,997 A | 12/1998 | Verrier et al. | |
| 5,843,139 A | 12/1998 | Godeke et al. | |
| 5,846,223 A | 12/1998 | Swartz et al. | |
| 5,868,669 A | 2/1999 | Iliff | |
| 5,876,353 A | 3/1999 | Riff | |
| 5,879,163 A | 3/1999 | Brown et al. | |
| 5,897,493 A | 4/1999 | Brown | |
| 5,899,855 A | 5/1999 | Brown | |
| 5,910,107 A | 6/1999 | Iliff | |
| 5,911,687 A | 6/1999 | Sato et al. | |
| 5,913,310 A | 6/1999 | Brown | |
| 5,918,603 A | 7/1999 | Brown | |
| 5,931,791 A | 8/1999 | Saltzstein et al. | |
| 5,933,136 A | 8/1999 | Brown | |
| 5,935,060 A * | 8/1999 | Iliff | 600/300 |
| 5,951,300 A | 9/1999 | Brown | |
| 5,957,861 A | 9/1999 | Combs et al. | |
| 5,960,403 A | 9/1999 | Brown | |
| 5,985,559 A | 11/1999 | Brown | |
| 5,987,519 A | 11/1999 | Peifer et al. | |
| 5,997,476 A | 12/1999 | Brown | |
| 6,007,493 A | 12/1999 | Ericksen et al. | |
| 6,022,315 A | 2/2000 | Iliff | |
| 6,024,699 A | 2/2000 | Surwit et al. | |
| 6,032,119 A | 2/2000 | Brown et al. | |
| 6,038,465 A | 3/2000 | Melton, Jr. | |
| 6,045,513 A | 4/2000 | Stone et al. | |
| 6,071,236 A | 6/2000 | Iliff | |
| 6,080,106 A | 6/2000 | Lloyd et al. | |
| 6,085,162 A | 7/2000 | Cherny | |
| 6,101,478 A | 8/2000 | Brown | |
| 6,113,540 A | 9/2000 | Iliff | |
| 6,144,837 A | 11/2000 | Quy | |
| 6,167,362 A | 12/2000 | Brown et al. | |
| 6,168,563 B1 | 1/2001 | Brown | |
| 6,234,964 B1 | 5/2001 | Iliff | |
| 6,246,992 B1 | 6/2001 | Brown | |
| 6,248,065 B1 | 6/2001 | Brown | |
| 6,270,456 B1 | 8/2001 | Iliff | |
| 6,290,646 B1 | 9/2001 | Cosentino et al. | |
| 6,328,699 B1 | 12/2001 | Eigler et al. | |
| 6,354,996 B1 | 3/2002 | Drinan et al. | |
| 6,454,705 B1 | 9/2002 | Cosentino et al. | |
| 6,755,783 B2 | 6/2004 | Cosentino et al. | |
| 6,849,045 B2 | 2/2005 | Iliff | |
| 7,127,290 B2 * | 10/2006 | Girouard et al. | 607/17 |
| 7,433,853 B2 * | 10/2008 | Brockwy et al. | 706/45 |
| 2001/0053875 A1 | 12/2001 | Iliff | |
| 2002/0133502 A1 | 9/2002 | Rosenthal et al. | |
| 2003/0083556 A1 | 5/2003 | Cosentino et al. | |
| 2004/0102685 A1 | 5/2004 | Cosentino et al. | |
| 2004/0117204 A1 | 6/2004 | Mazar et al. | |
| 2004/0122297 A1 | 6/2004 | Stahmann et al. | |
| 2004/0147969 A1 | 7/2004 | Mann et al. | |
| 2004/0172080 A1 * | 9/2004 | Stadler et al. | 607/17 |
| 2004/0225533 A1 | 11/2004 | Cosentino et al. | |
| 2005/0015115 A1 | 1/2005 | Sullivan et al. | |
| 2006/0015017 A1 | 1/2006 | Cosentino et al. | |
| 2006/0030890 A1 | 2/2006 | Cosentino et al. | |
| 2007/0021979 A1 | 1/2007 | Cosentino et al. | |

FOREIGN PATENT DOCUMENTS

| | | |
|---|---|---|
| EP | 0 251 520 A2 | 1/1988 |
| JP | 09173304 | 7/1997 |
| WO | WO 98/40835 | 9/1998 |
| WO | WO 00/62662 | 10/2000 |
| WO | WO 01/39089 A1 | 5/2001 |
| WO | WO 03/075756 A1 | 9/2003 |

OTHER PUBLICATIONS

"Telemedicine NEW: BP-TEL™ Transtelephonic Blood Pressure: Your Partner In Telemedicine", http://www.aerotel.com/telemed/, 2 pgs. (Feb. 6, 2001) last updated.

"Telemedicine, Your Partner in Telemedicine", Aerotel Medical Systems, Ltd., Internet at http://www.aerotel.com/telemed/under.html, last updated Sep. 5, 1998.

"Thin-Link: Like Having a Personal Coach and Dietitian in Your Home Every Day," http://web.archive.org/web/20041009141519/www.thin-link.com/program_weightloss.html, 2 pages (Date Printed Aug. 31, 2005).

International Search Report for International Application No. PCT/US 03/07099, 8 pp., Jul. 22, 2003.

Patel, U. et al., "A Computer-Based, Automated, Telephonic System to Monitor Patient Progress in the Home Setting", *Journal of Medical Systems*, vol. 16, Nos. 2/3, pp. 101-112 (1992).

Teixeira, P. et al., "Weight Loss Readiness in Middle-Aged Women: Psychosocial Predictors of Success for Behavioral Weight Reduction," *Journal of Behavioral Medicine*, vol. 25, No. 6, pp. 499-523 (Dec. 2002).

Yazolino, L., "Effective, Daily At-home Monitoring of Chronically III Patients," *Medical Electronics*, 4 pages (Sep. 1998).

Lüthje, L. et al., "Detection of heart failure decompensation using intrathoracic impedance monitoring by a triple-chamber implantable defibrillator," *Heart Rhythm*, vol. 2, No. 9, pp. 997-999 (Sep. 2005).

* cited by examiner

SYSTEM, METHOD, AND APPARATUS FOR COMBINING INFORMATION FROM AN IMPLANTED DEVICE WITH INFORMATION FROM A PATIENT MONITORING APPARATUS

RELATED APPLICATIONS

This application is a continuation-in-part of U.S. application Ser. No. 11/181,682 filed on Jul. 13, 2005, entitled "SYSTEM, METHOD, AND APPARATUS FOR AUTOMATED INTERACTIVE VERIFICATION OF AN ALERT GENERATED BY A PATIENT MONITORING DEVICE," which is a continuation-in-part of U.S. application Ser. No. 10/746,325 filed on Dec. 23, 2003, entitled "WEIGHT LOSS OR WEIGHT MANAGEMENT SYSTEM," which is a continuation-in-part of U.S. application Ser. No. 10/093,948 filed on Mar. 7, 2002, entitled "REMOTE SYSTEM FOR AMBULATORY COPD PATIENTS," which is a continuation-in-part of U.S. application Ser. No. 09/949,197 filed on Sep. 7, 2001, now U.S. Pat. No. 6,755,783 entitled "APPARATUS AND METHOD FOR TWO-WAY COMMUNICATION IN A DEVICE FOR MONITORING AND COMMUNICATING WELLNESS PARAMETERS OF AMBULATORY PATIENTS," which is a continuation-in-part of U.S. application Ser. No. 09/293,619 filed on Apr. 16, 1999, now U.S. Pat. No. 6,290,646 entitled "APPARATUS AND METHOD FOR MONITORING AND COMMUNICATING WELLNESS PARAMETERS OF AMBULATORY PATIENTS," all of which are hereby incorporated by reference in their entirety.

BACKGROUND

There is a need in the medical profession for an apparatus and method capable of monitoring and transmitting physiological and wellness parameters of ambulatory patients to a remote site where a medical professional caregiver evaluates such physiological and wellness parameters. Specifically, there is a need for an interactive apparatus that is coupled to a remote computer such that a medical professional caregiver can supervise and provide medical treatment to remotely located ambulatory patients.

There is needed an apparatus that monitors and transmits physiological and wellness parameters of ambulatory patients to a remote computer, whereby a medical professional caregiver evaluates the information and provokes better overall health care and treatment for the patient. Accordingly, such an apparatus can be used to prevent unnecessary hospitalizations of such ambulatory patients.

Also, there is needed an apparatus for monitoring and transmitting such physiological and wellness parameters that is easy to use and that is integrated into a single unit. For example, there is a need for an ambulatory patient monitoring apparatus that comprises: a transducing device for providing electronic signals representative of measured physiological parameters, such as weight; an input/output device; and a communication device as a single integrated unit that offers ambulatory patients ease of use, convenience and portability.

Patients suffering from chronic diseases, such as chronic heart failure, will benefit from such home monitoring apparatus. These patients normally undergo drug therapy and lifestyle changes to manage their medical condition. In these patients, the medical professional caregiver monitors certain wellness parameters and symptoms including: weakness, fatigue, weight gain, edema, dyspnea (difficulty breathing or shortness of breath), nocturnal cough, orthopnea (inability to lie flat in bed because of shortness of breath), and paroxysmal nocturnal dyspnea (awakening short of breath relieved by sitting or standing); and body weight to measure the response of drug therapy. Patients will also benefit from daily reminders to take medications (improving compliance), reduce sodium intake and perform some type of exercise. With the information received from the monitoring device, the medical professional caregiver can determine the effectiveness of the drug therapy, the patient's condition, whether the patient's condition is improving or whether the patient requires hospitalization or an office consultation to prevent the condition from getting worse.

Accordingly, there is needed an apparatus and method for monitoring the patients from a remote location, thus allowing medical professional caregivers to receive feedback of the patient's condition without having to wait until the patient's next office visit. In addition, there is needed an apparatus and method that allows medical professional caregivers to monitor and manage the patient's condition to prevent the rehospitalization of such patient, or prevent the patient's condition from deteriorating to the point where hospitalization would be required. As such, there are social as well as economic benefits to such an apparatus and method.

The patient receives the benefits of improved health when the professional caregiver is able to monitor and quickly react to any adverse medical conditions of the patient or to any improper responses to medication. Also, society benefits because hospital resources will not be utilized unnecessarily.

As a group, patients suffering from chronic heart failure are the most costly to treat. There are approximately 5 million patients in the U.S.A. and 15 million worldwide with chronic heart failure. The mortality rate of patients over 65 years of age is 50%. Of those that seek medical help and are hospitalized, 50% are rehospitalized within 6 months. Of these, 16% will be rehospitalized twice. The patients that are hospitalized spend an average of 9.1 days in the hospital at a cost of $12,000.00 for the period. Accordingly, there is a need to reduce the rehospitalization rate of chronic heart failure patients by providing improved in-home patient monitoring, such as frequently monitoring the patient's body weight and adjusting the drug therapy accordingly.

Approximately 60 million American adults ages 20 through 74 are overweight. Obesity is a known risk factor for heart disease, high blood pressure, diabetes, gallbladder disease, arthritis, breathing problems, and some forms of cancer such as breast and colon cancer. Americans spend $33 billion dollars annually on weight-reduction products and services, including diet foods, products and programs.

There is a need in the weight management profession for an apparatus and method capable of monitoring and transmitting physiological and wellness parameters of overweight/obese patients to a remote site where a weight management professional or nutritionist evaluates such physiological and wellness parameters. Specifically, there is a need for an interactive apparatus that is coupled to a remote computer such that a weight management professional or nutritionist can supervise and provide nutritional guidance to remotely located individuals.

The apparatus allows overweight individuals to participate in a weight loss/management program with accurate weight monitoring from home. The apparatus improves the convenience for the individual participant by eliminating the need to constantly commute to the weight management center and "weigh-in." Furthermore, the individual can participate in a weight management program while under professional supervision from the privacy and comfort of their own home. Moreover, the apparatus allows the weight management professional to intervene and adapt the individuals diet and exercise routine based on the weight and wellness information received.

For the foregoing reasons, there is a need for an apparatus, system and method capable of monitoring and transmitting physiological and wellness parameters of ambulatory patients, such as body weight, to a remote location where a medical professional caregiver, weight management professional or nutritionist can evaluate and respond to the patient's medical wellness condition.

SUMMARY

Against this backdrop the present invention was created. According to one embodiment of the present invention, a computer-implemented method of detecting an impending decompensation of heart failure in a patient includes receiving transthoracic impedance data measured by a cardiac rhythm management device implanted in the patient. Also, a weight measurement of the patient is obtained. Additionally, impending decompensation of acute heart failure is detected, based at least in part upon the weight measurement and the transthoracic impedance data received from the cardiac rhythm management device.

According to another embodiment of the present invention, a computer-implemented method of detecting impending decompensation of heart failure in a patient, may include receiving transthoracic impedance data measured by a cardiac rhythm management device implanted in the patient. Also, one or more questions are posed to the patient. Additionally, answers to the one or more questions are received. Finally, impending decompensation of heart failure is detected, based at least in part upon the answers and the transthoracic impedance data received from the cardiac rhythm management device.

According to yet another embodiment of the present invention, a computer-implemented method of detecting impending decompensation of heart failure in a patient may include receiving, with a processor device external to the patient, transthoracic impedance data measured by a cardiac rhythm management device implanted in the patient. Additionally, a physiological parameter of the patient is measured. Further, the physiological parameter is communicated to the processor device. The processor device receives answers to one or more questions posed to the patient. Finally, the processor device detects impending decompensation of heart failure, based at least in part upon a score generated based upon the answers and the physiological parameter.

BRIEF DESCRIPTION OF THE DRAWINGS

These and other features, aspects and advantages of the invention will become better understood with regard to the following description, appended claims and accompanying drawings where:

DESCRIPTION

The embodiments of the invention described herein are implemented as a medical apparatus, system and method capable of monitoring wellness parameters and physiological data of ambulatory patients and transmitting such parameters and data to a remote location. At the remote location a medical professional caregiver monitors the patient's condition and provides medical treatment as may be necessary.

The monitoring device incorporates transducing devices for converting the desired measured parameters into electrical signals capable of being processed by a local computer or microprocessor system. The device interacts with the ambulatory patient and then, via an electronic communication device such as a modem, transmits the measured parameters to a computer located at a remote site. At the remote location the various indicia of the ambulatory patient's condition are monitored and analyzed by the medical professional caregiver. To provide the ambulatory patient with an added level of convenience and ease of use, such monitoring device is contained in a single integrated package. Communication is established between the monitoring apparatus and a remote computer via modem and other electronic communication devices that are generally well known commercially available products. At the remote location, the caregiver reviews the patient's condition based on the information communicated (e.g. wellness parameters and physiological data) and provokes medical treatment in accordance with such information.

Figure 1A:
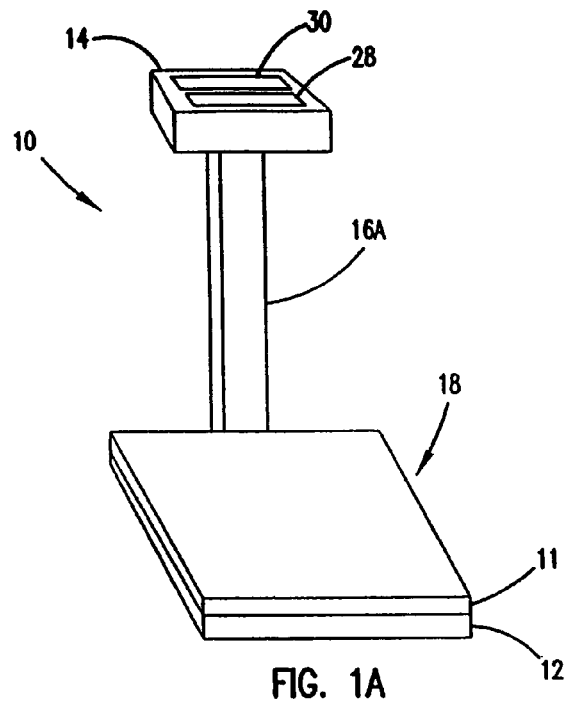
FIGS. 1A-E illustrates several embodiments of the monitoring apparatus in accordance with the invention.

Referring now to FIG. 1A, as this embodiment of the invention is described herein, an integrated monitoring apparatus is shown generally at 10. The integrated monitoring apparatus 10 includes an electronic scale 18. The electronic scale 18 further includes a top plate 11 and a base plate 12. The integrated monitoring apparatus 10 further includes a housing 14 and a support member 16A. The base plate 12 is connected to the housing 14 through the support member 16A. The housing 14 further includes output device(s) 30 and input device(s) 28. The apparatus 10 is integrated as a single unit with the support member coupling the base plate 12 and the housing 14, thus providing a unit in a one-piece construction.

It will be appreciated that other physiological transducing devices can be utilized in addition to the electronic scale 18. For example, blood pressure measurement apparatus and electrocardiogram (EKG) measurement apparatus can be utilized with the integrated monitoring apparatus 10 for recordation and/or transmission of blood pressure and EKG measurements to a remote location. It will be appreciated that other monitoring devices of physiological body functions that provide an analog or digital electronic output may be utilized with the monitoring apparatus 10.

Figure 1B:
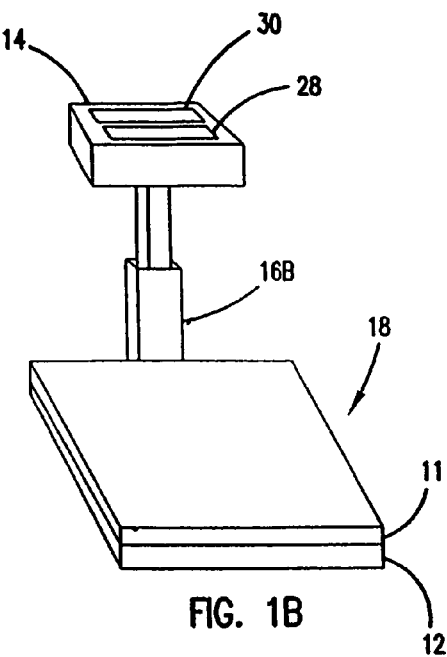
Figure 1C:
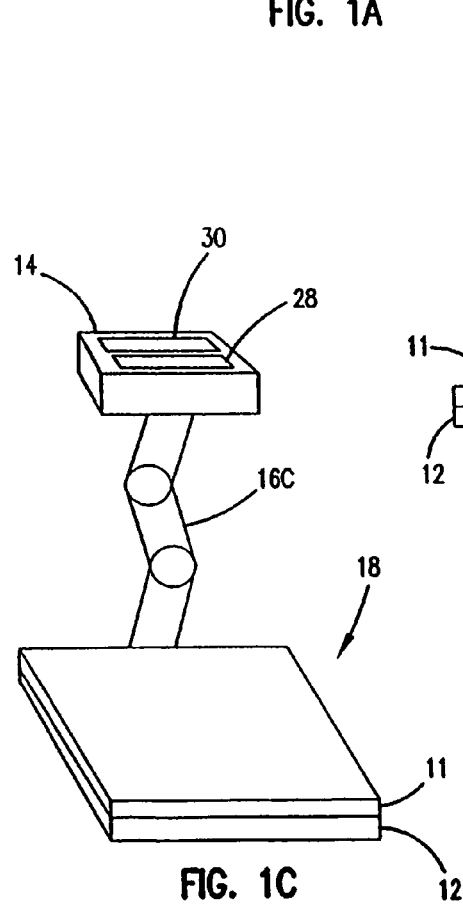
Figure 1D:
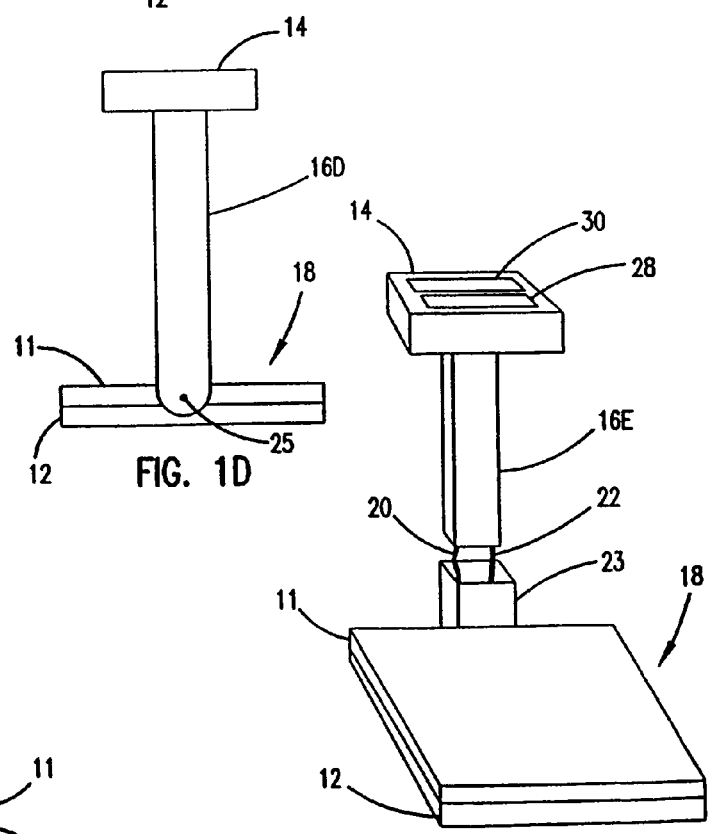
Figure 1E:
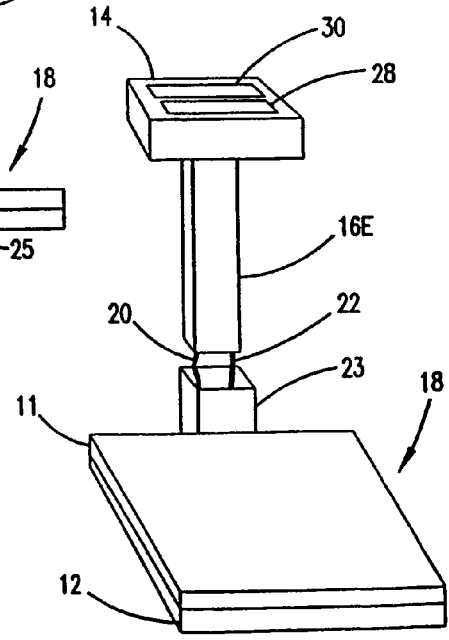

Referring to FIGS. 1B, 1C, 1D and 1E it will be appreciated that the support member 16A (FIG. 1A) can be made adjustable. For example, FIG. 1B illustrates an embodiment of the invention utilizing a telescoping support member 16B. Likewise, FIG. 1C illustrates an embodiment of the invention utilizing a folding articulated support member 16C. FIG. 1D illustrates yet another embodiment of the invention utilizing support member 16D that folds at a pivot point 25 located at its base. It will also be appreciated that other types of articulated and folding support members may be utilized in other embodiments of the invention. For example, FIG. 1E illustrates an embodiment of the invention providing a support member 16E that is removably insertable into a socket 23. A cable 22 is passed through the support member 16E to carry electrical signals from the electronic scale 18 to the housing 14 for further processing. A tether 20 is provided to restrain the movement of the support member 16E relative to the base plate 12 once the it is removed from the socket 23.

Figure 2:
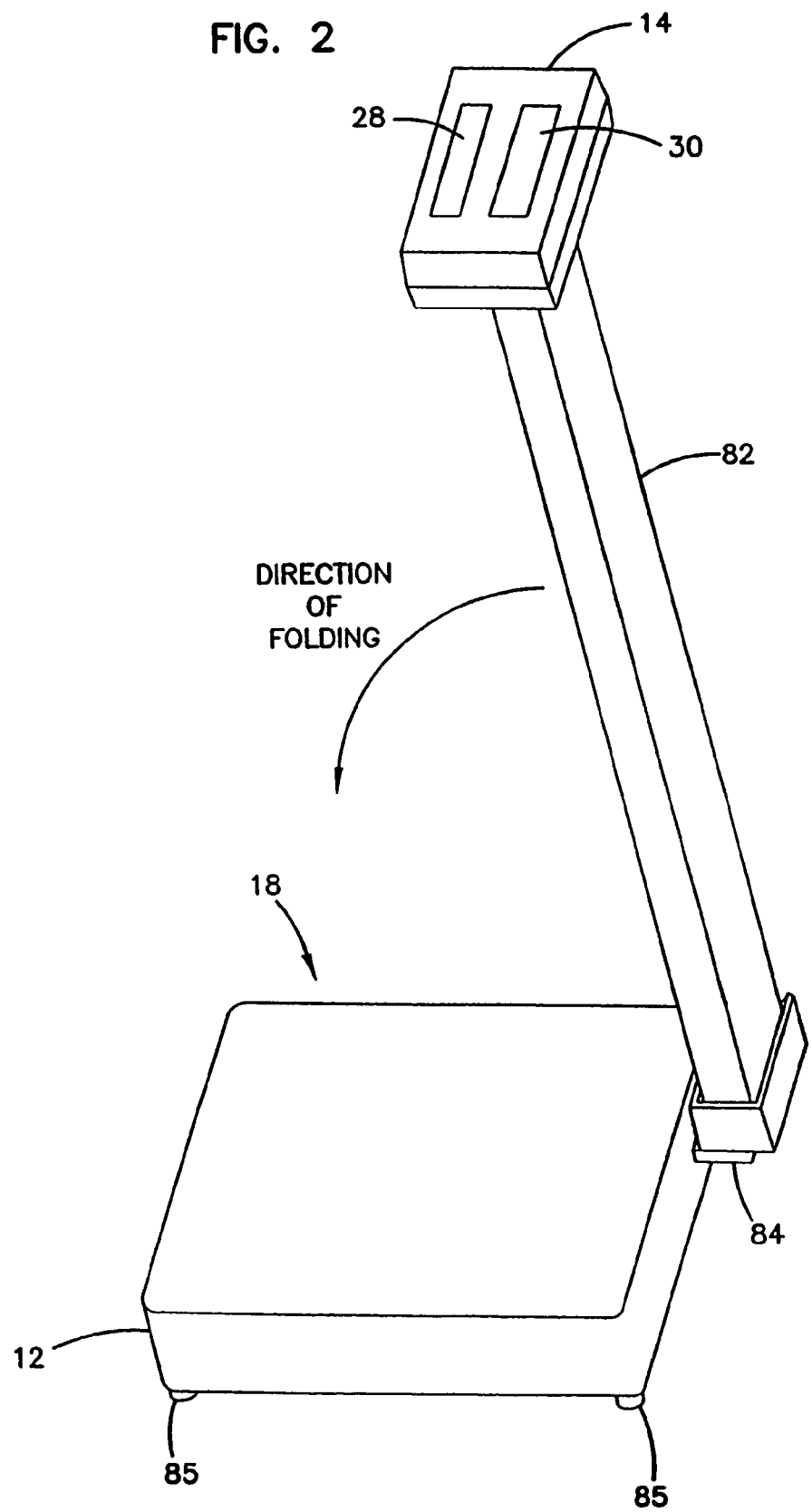
FIG. 2 illustrates a monitoring apparatus with a support member in accordance with one embodiment of the invention.

FIG. 2 illustrates an embodiment of the invention where the support member 82 folds about pivot point 84. Folding the integrated monitoring apparatus about pivot point 84 provides a convenient method of shipping, transporting or moving the apparatus in a substantially horizontal orientation. The preferred direction of folding is indicated in the figure, however, the support member 82 can be made to fold in either direction. Furthermore, an embodiment of the invention provides rubber feet 85 underneath the base plate 12.

Figure 3:
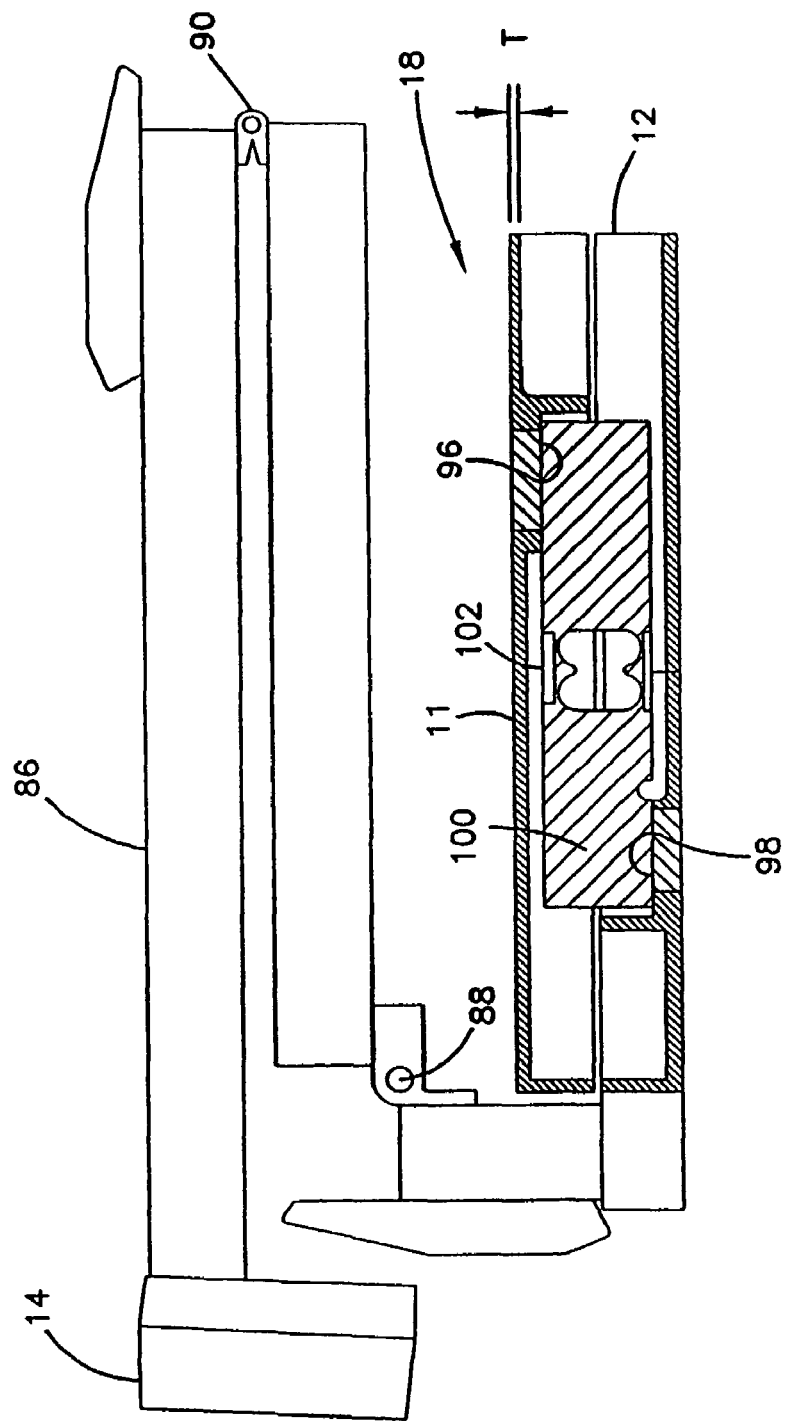
FIG. 3 illustrates a monitoring apparatus with a support member in accordance with one embodiment of the invention.

Furthermore, FIG. 3 illustrates one embodiment of the invention providing an articulated, folding support member 86. The support member 86 folds at two hinged pivot points

88, 90. Also illustrated is a sectional view of the scale 18, top plate 11, base plate 12, load cell 100 and strain gage 102.

Figure 4:
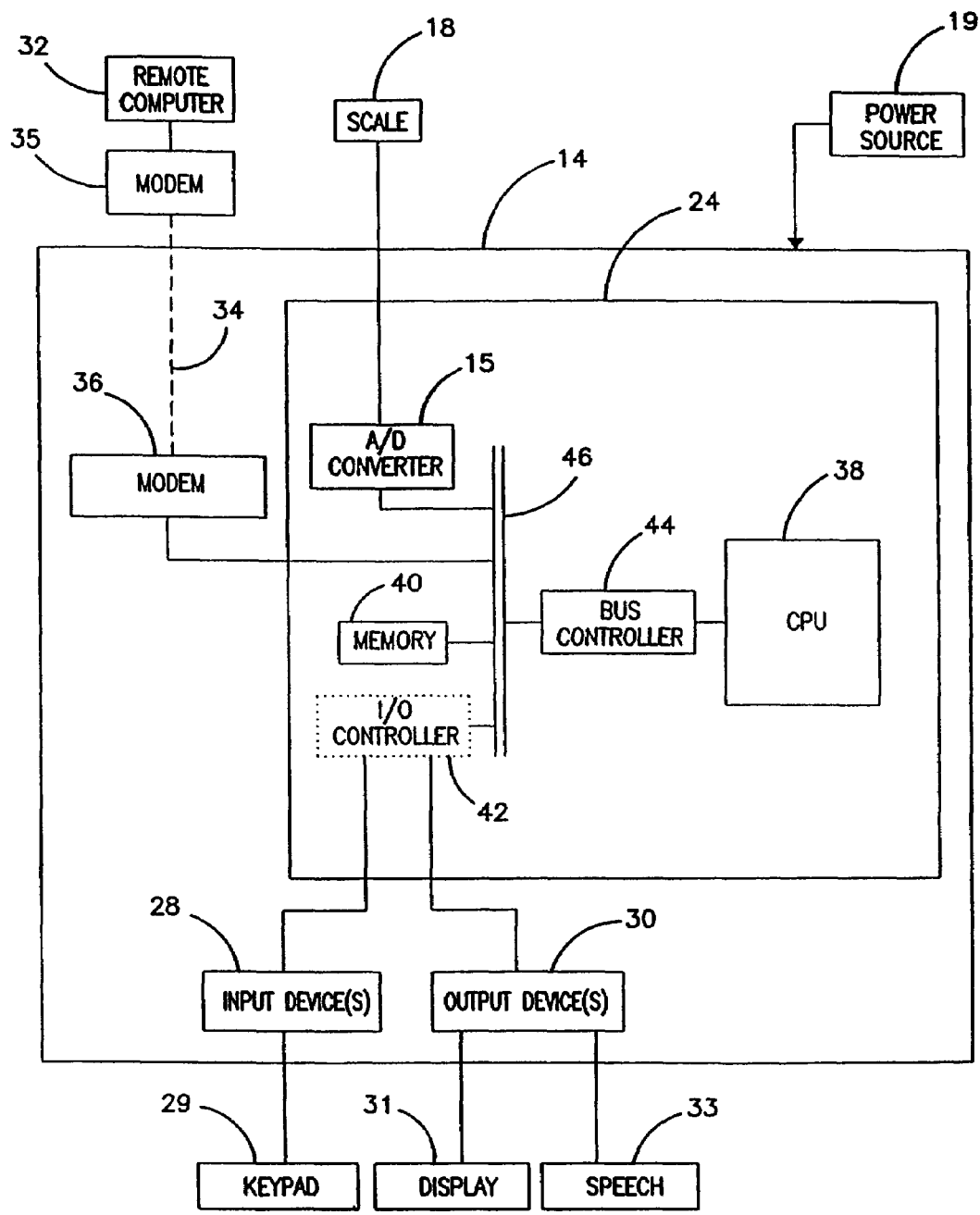
FIG. 4 is a functional block diagram of a microprocessor system forming an environment in which one embodiment of the invention may be employed.

Referring now to FIG. 4, a microprocessor system 24 including a CPU 38, a memory 40, an optional input/output (I/O) controller 42 and a bus controller 44 is illustrated. It will be appreciated that the microprocessor system 24 is available in a wide variety of configurations and is based on CPU chips such as the Intel, Motorola or Microchip PIC family of microprocessors or microcontrollers.

It will be appreciated by those skilled in the art that the monitoring apparatus requires an electrical power source 19 to operate. As such, the monitoring apparatus may be powered by: ordinary household A/C line power, DC batteries or rechargeable batteries. Power source 19 provides electrical power to the housing for operating the electronic devices. A power source for operating the electronic scale 18 is generated within the housing, however those skilled in the art will recognize that a separate power supply may be provided or the power source 19 may be adapted to provide the proper voltage or current for operating the electronic scale 18.

The housing 14 includes a microprocessor system 24, an electronic receiver/transmitter communication device such as a modem 36, an input device 28 and an output device 30. The modem 36 is operatively coupled to the microprocessor system 24 via the electronic bus 46, and to a remote computer 32 via a communication network 34 and modem 35. The communication network 34 being any communication network such as the telephone network, wide area network or Internet. It will be appreciated that the modem 36 is a generally well known commercially available product available in a variety of configurations operating at a variety of BAUD rates. In one embodiment of the invention the modem 36 is asynchronous, operates at 2400 BAUD and is readily available off-the-shelf from companies such as Rockwell or Silicon Systems Inc. (SSI).

It will be appreciated that output device(s) 30 may be interfaced with the microprocessor system 24. These output devices 30 include a visual electronic display device 31 and/or a synthetic speech device 33. Electronic display devices 31 are well known in the art and are available in a variety of technologies such as vacuum fluorescent, liquid crystal or Light Emitting Diode (LED). The patient reads alphanumeric data as it scrolls on the electronic display device 31. Output devices 30 include a synthetic speech output device 33 such as a Chipcorder manufactured by ISD (part No. 4003). Still, other output devices 30 include pacemaker data input devices, drug infusion pumps or transformer coupled transmitters.

It will be appreciated that input device(s) 28 may be interfaced with the microprocessor system 24. In one embodiment of the invention an electronic keypad 29 is provided for the patient to enter responses into the monitoring apparatus. Patient data entered through the electronic keypad 29 may be scrolled on the electronic display 31 or played back on the synthetic speech device 33.

The microprocessor system 24 is operatively coupled to the modem 36, the input device(s) 28 and the output device(s) 30. The electronic scale 18 is operatively coupled to the central system 24. Electronic measurement signals from the electronic scale 18 are processed by the A/D converter 15. This digitized representation of the measured signal is then interfaced to the CPU 38 via the electronic bus 46 and the bus controller 44. In one embodiment of the invention, the physiological transducing device includes the electronic scale 18. The electronic scale 18 is generally well known and commercially available. The electronic scale 18 may include one or more of the following elements: load cells, pressure transducers, linear variable differential transformers (LVDTs), capacitance coupled sensors, strain gages and semiconductor strain gages. These devices convert the patient's weight into a useable electronic signal that is representative of the patient's weight.

In will be appreciated that Analog-to-Digital (A/D) converters are also generally well known and commercially available in a variety of configurations. Furthermore, an A/D converter 15 may be included within the physiological transducing device or within the microprocessor system 24 or within the housing 14. One skilled in the art would have a variety of design choices in interfacing a transducing device comprising an electronic sensor or transducer with the microprocessor system 24.

The scale 18 may provide an analog or digital electronic signal output depending on the particular type chosen. If the electronic scale 18 provides an analog output signal in response to a weight input, the analog signal is converted to a digital signal via the A/D converter 15. The digital signal is then interfaced with the electronic bus 46 and the CPU 38. If the electronic scale 18 provides a digital output signal in response to a weight input, the digital signal may be interfaced with electronic bus 46 and the CPU 38.

Figure 5:
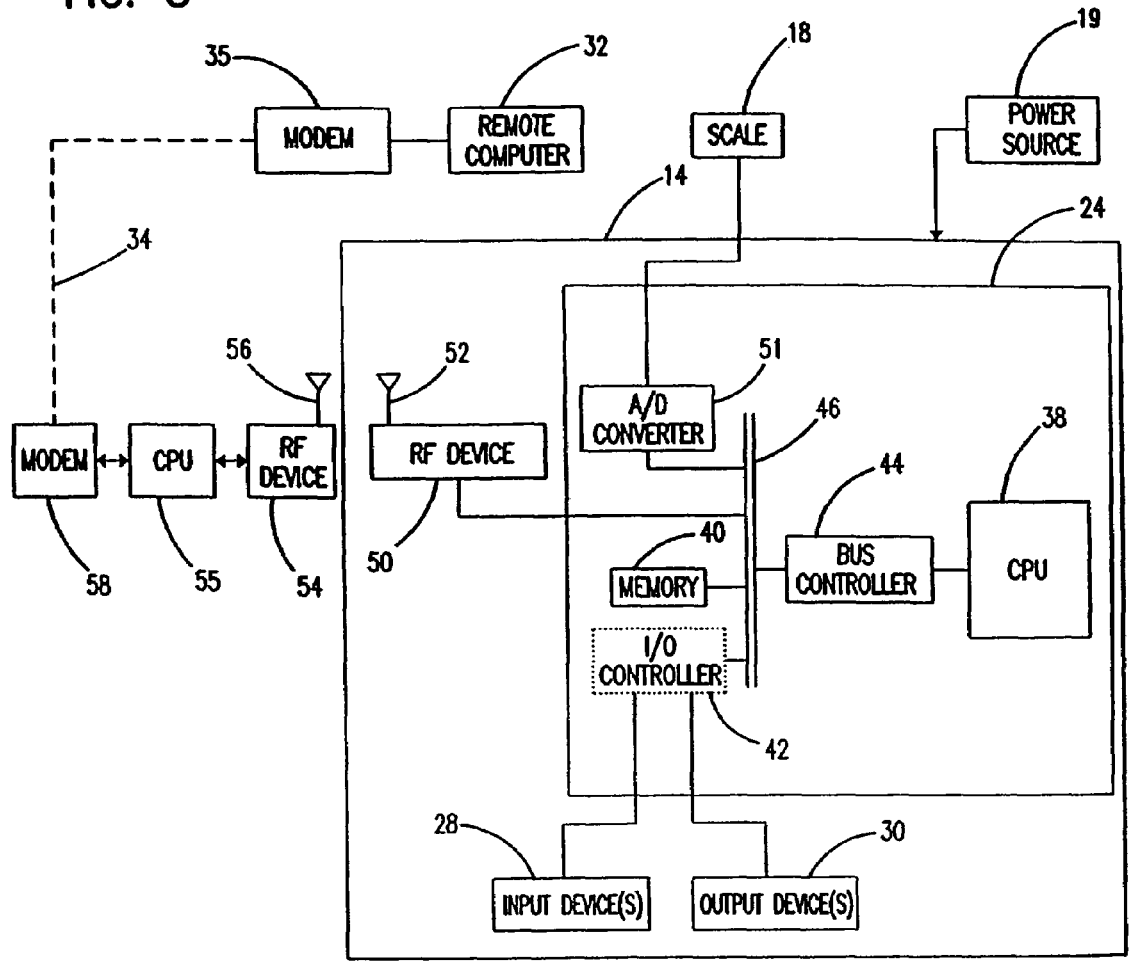
FIG. 5 is functional block diagram of a microprocessor system forming the environment in which one embodiment of the invention may be employed.

FIG. 5 illustrates one embodiment of the invention where the communication device is a radio frequency (RF) transceiver. The transceiver comprises a first radio frequency device 50 including an antenna 52, and a second radio frequency device 54, including an antenna 56. The first radio frequency device 52 is operatively coupled to the microprocessor system 24 via the electronic bus 46, and is in radio communication with the second radio frequency device 54. The second radio frequency device 54 is operatively coupled through a microprocessor 55 which is operatively coupled to a modem 58. The modem 58 is coupled to the communication network 34 and is in communication with the remote computer 32 via the modem 35. The first radio frequency device 50 and the second radio frequency device 54 are remotely located, one from the other. It will be appreciated that such radio frequency devices 50, 54 are generally well known and are commercially available products from RF Monolithics Inc. (RFM).

In one embodiment of the invention, such transceivers operate at radio frequencies in the range of 900-2400 MHz. Information from the microprocessor system 24 is encoded and modulated by the first RF device 50 for subsequent transmission to the second RF device 54, located remotely therefrom. The second RF device 54 is coupled to a conventional modem 58 via the microprocessor 55. The modem 58 is coupled to the communication network 34 via a in-house wiring connection and ultimately to the modem 35 coupled to the remote computer 32. Accordingly, information may be transmitted to and from the microprocessor system 24 via the RF devices 50, 54 via a radio wave or radio frequency link, thus providing added portability and flexibility to the monitoring apparatus 10. It will be appreciated that various other communications devices may be utilized such as RS-232 serial communication connections, Internet communications connection as well as satellite communication connections. Other communications devices that operate by transmitting and receiving infra-red (IR) energy can be utilized to provide a wireless communication link between the patient monitoring apparatus 10 and a conveniently located network connection. Furthermore, X-10™ type devices can also be used as part of a communication link between the patient monitoring apparatus 10 and a convenient network connection in the home. X-10 USA and other companies manufacture a variety of devices that transmit/receive data without the need for any special wiring. The devices works by sending signals through the home's regular electrical wires using what is called power line carrier (PLC).

Figure 6:
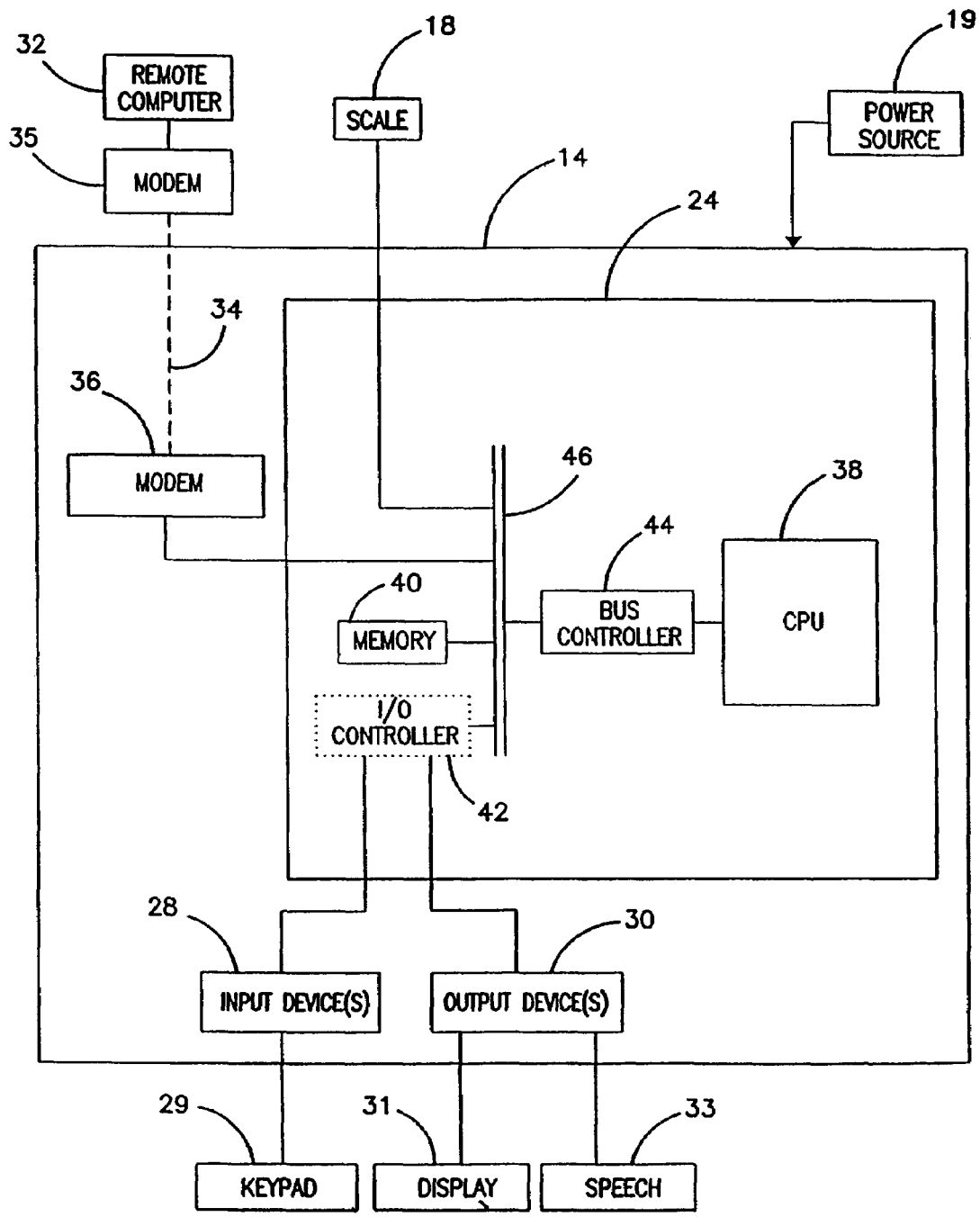
FIG. 6 is a functional block diagram of a microprocessor system forming the environment in which one embodiment of the invention may be employed.

Referring now to FIG. 6, one embodiment of the invention wherein a digital electronic scale 21 is provided. Digital weight measurements from the digital electronic scale 21 may be interfaced with the microprocessor system and CPU 38 without requiring additional amplification, signal conditioning and A/D converters.

Figure 7:
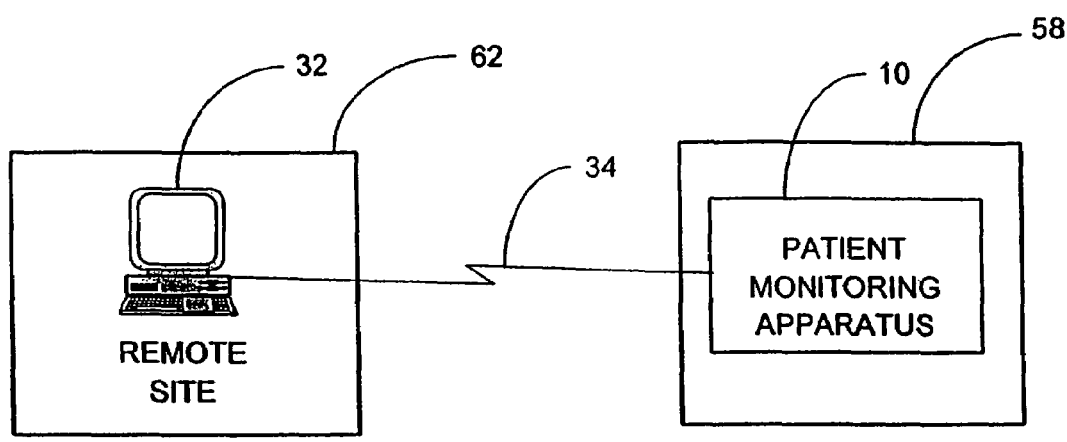
FIG. 7 illustrates a system in which one embodiment of the invention may be employed.

Referring now to FIG. 7, a two way communication system in accordance with the principals of the present invention is shown. The physiological data of an ambulatory patient is monitored utilizing monitoring apparatus 10 at a local site 58 and is transmitted to a remote computer 32 located at a remote computer site 62 via communication network 34. At the remote computer site 62 a medical professional caregiver such as a nurse, physician or nurse practitioner monitors the patient data and provokes treatment in accordance with such data.

Figure 8:
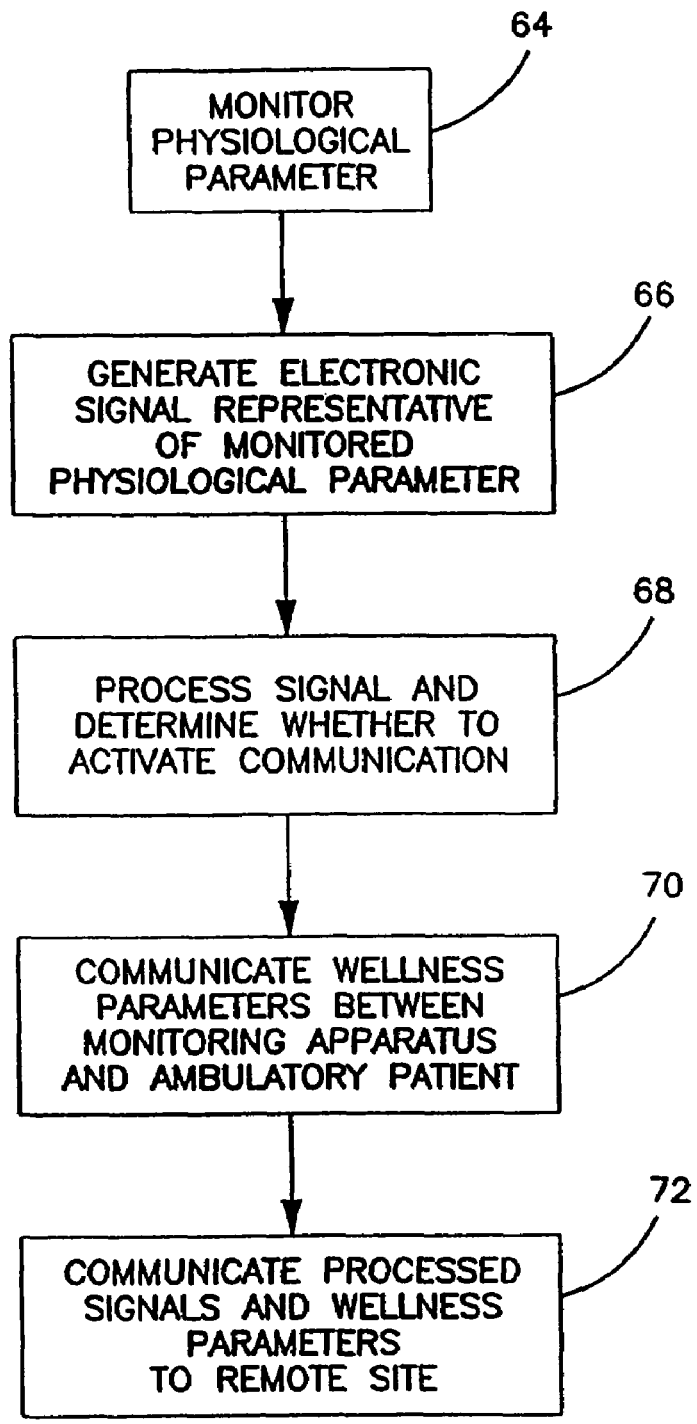
FIG. 8 is a logic flow diagram illustrating the steps utilized to implement one embodiment of the invention.

Operations to perform the preferred embodiment of the invention are shown in FIG. 8. Block 64 illustrates the operation of monitoring or measuring the ambulatory patient's physiological parameter. In one embodiment of the invention, namely for chronic heart failure patients, the physiological parameter monitored is the patient's weight. However, it will be appreciated by those skilled in the art that the physiological parameters may include blood pressure, EKG, temperature, urine output and any other.

Block 66 illustrates the operation of converting a monitored or measured physiological parameter from a mechanical input to an electronic output by utilizing a transducing device. In one embodiment of the invention the transducing device is an electronic scale 18, which converts the patient's weight into a useable electronic signal.

At block 68, the microprocessor system 24 processes the electronic signal representative of the transduced physiological parameter. If the resulting parameter value is within certain preprogrammed limits the microprocessor system 24 initiates communication within the remote computer 32 via the communication device 36 over the communication network 34.

Block 70 illustrates the operation whereby information such as wellness parameters and physiological data are communicated between the monitoring apparatus 10 and the ambulatory patient. An exemplary list of the questions asked to the patient by the monitoring apparatus are provided in Table 5.

Referring now to FIGS. 7 and 8, upon establishing communication between the local monitoring apparatus 10, at the local site 58, and the remote computer 32, at remote site 62, block 72 illustrates the operation of communicating or transmitting processed signals representative of physiological data and wellness parameters from the local site 58 to the remote site 62.

Figure 9:
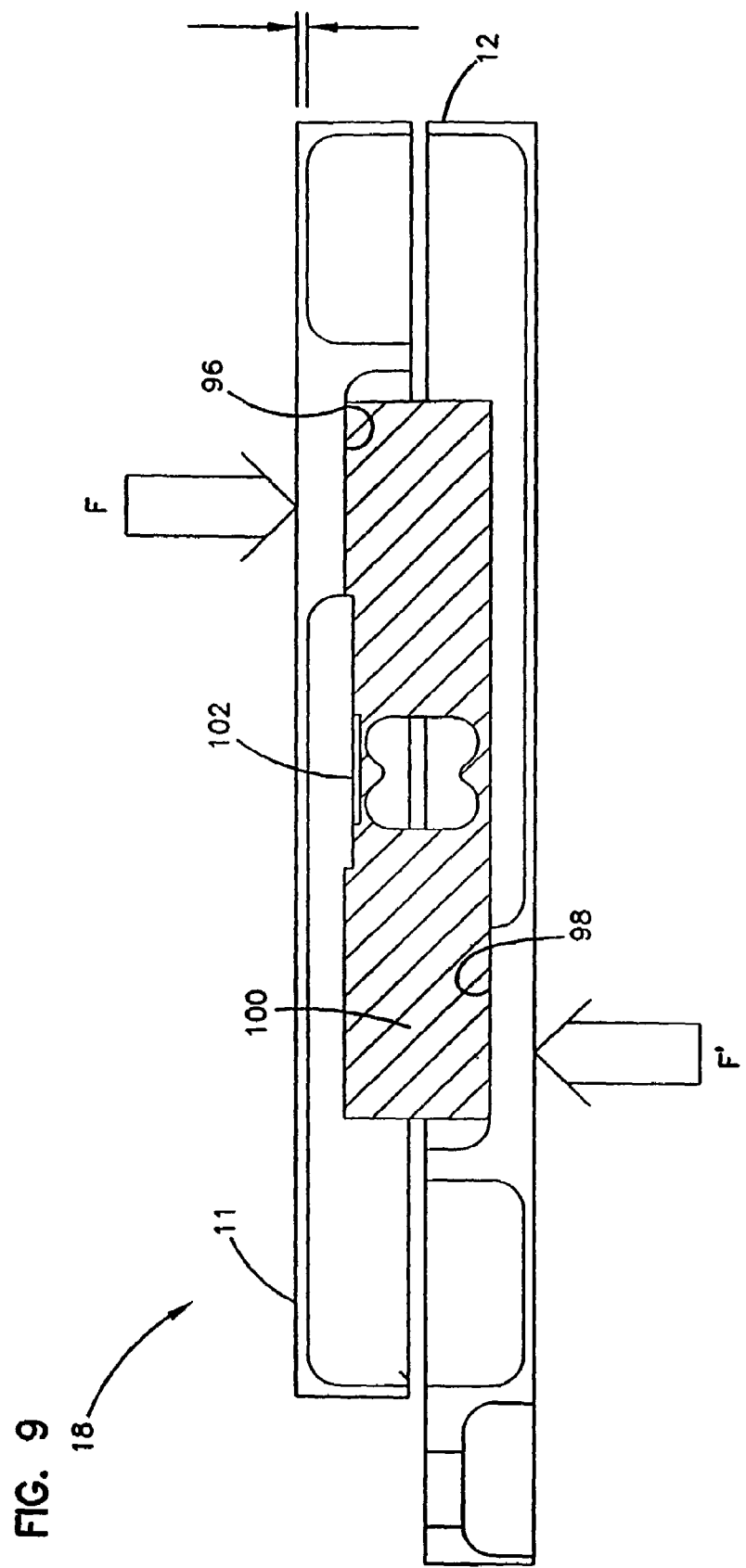
FIG. 9 illustrates a sectional view of the electronic scale in accordance with one embodiment of the invention.

FIG. 9 is a sectional view the scale 18 portion of one embodiment of the invention. The scale 18 comprises a top plate 11 and a base plate 12. The top plate 11 and the base plate 12 having a thickness "T". A load cell 100 is disposed between the top plate 11 and the base plate 12 and rests on support/mounting surfaces 96 and 98.

The load cell 100 is a transducer that responds to a forces applied to it. During operation, when a patient steps on the electronic scale 18, the load cell 100 responds to a force "F" transmitted through the top plate 11 and a first support/mounting surface 96. The support/mounting surface 96 is contact with a first end on a top side of the load cell 100. A force "F'" that is equal and opposite to "F" is transmitted from the surface that the electronic scale 18 is resting on, thorough the base plate 12 and a second support/mounting surface 98. The second support/mounting surface 98 is in contact with a second end on a bottom side of the load cell 100. In one embodiment, the load cell 100 is attached to the top plate 11 and the base plate 12, respectively, with bolts that engage threaded holes provided in the load cell 100. In one embodiment the load cell 100 further comprises a strain gage 102.

The strain gage 102 made from ultra-thin heat-treated metallic foils. The strain gage 102 changes electrical resistance when it is stressed, e.g. placed in tension or compression. The strain gage 102 is mounted or cemented to the load cell 100 using generally known techniques in the art, for example with specially formulated adhesives, urethanes, epoxies or rubber latex. The positioning of the strain gage 102 will generally have some measurable effect on overall performance of the load cell 100. Furthermore, it will be appreciated by those skilled in the art that additional reference strain gages may be disposed on the load cell where they will not be subjected to stresses or loads for purposes of temperature compensating the strain gage 102 under load. During operation over varying ambient temperatures, signals from the reference strain gages may be added or subtracted to the measurement signal of the strain gage 102 under load to compensate for any adverse effects of ambient temperature on the accuracy of the strain gage 102.

The forces, "F" and "F'", apply stress to the surface on which the strain gage 102 is attached. The weight of the patient applies a load on the top plate 11. Under the load the strain gage(s) 102 mounted to the top of the load cell 100 will be in tension/compression as the load cell bends. As the strain gage 102 is stretched or compressed its resistance changes proportionally to the applied load. The strain gage 102 is electrically connected such that when an input voltage or current is applied to the strain gage 102, an output current or voltage signal is generated which is proportional to the force applied to the load cell 100. This output signal is then converted to a digital signal by A/D converter 15.

Figure 10:
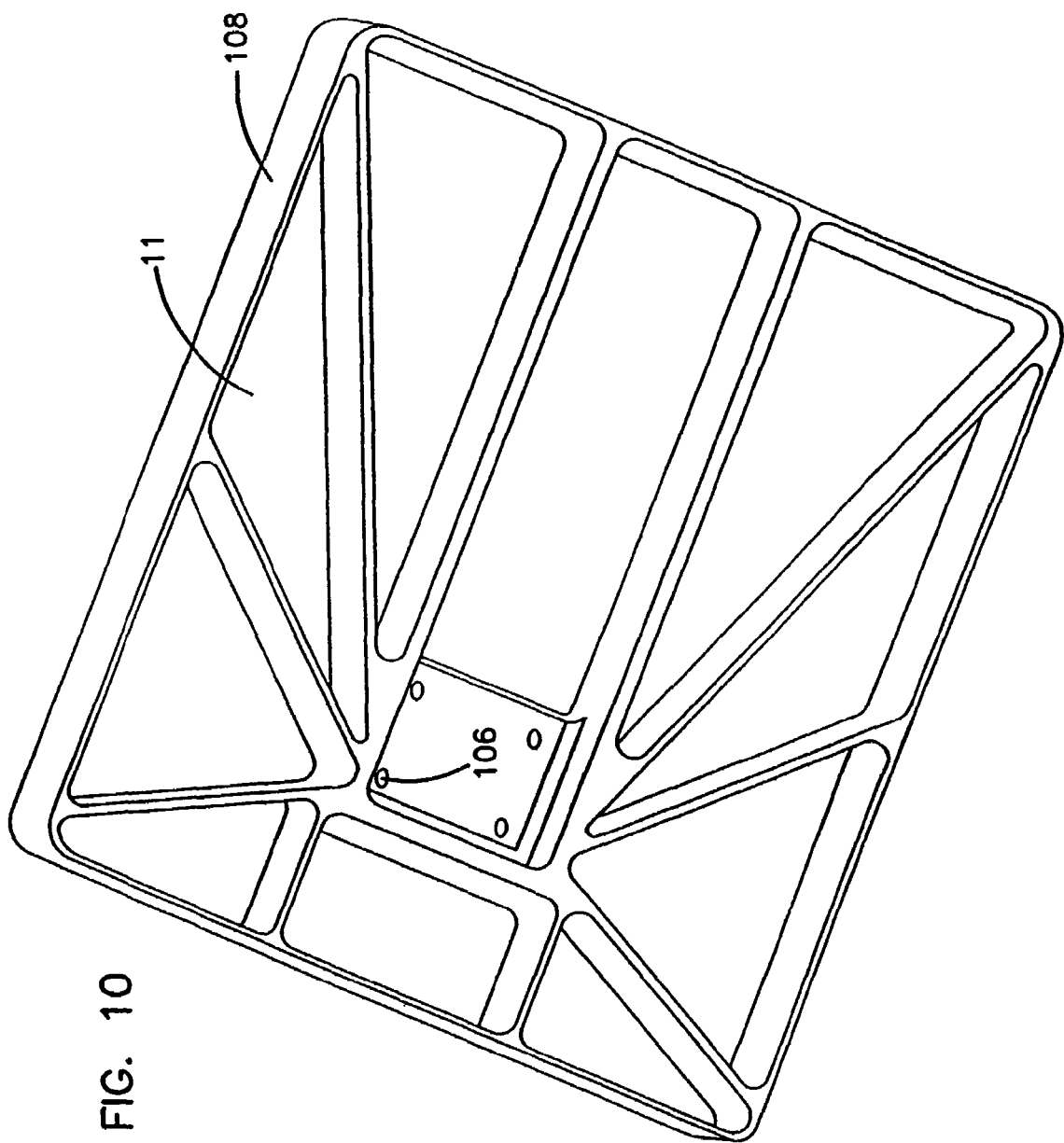
FIG. 10 illustrates a top plate of the electronic scale in accordance with one embodiment of the invention.

The design of the load cell 100 having a first end on a top side attached to the top plate 11 and a second end on a bottom side attached to the base plate 12 provides a structure for stressing the strain gage 102 in a repeatable manner. The structure enables a more accurate and repeatable weight measurement. This weight measurement is repeatable whether the scale 18 rests on a rigid tile floor or on a carpeted floor. FIG. 10 illustrates one embodiment of the top plate 11 that provides four mounting holes 106 for attaching the base plate 12 to one end of the load cell 100. The base plate 12 provides similar holes for attaching to the other end of the load cell 100. The top plate 11 and the base plate 12 (not shown) each comprise a plurality of stiffening ribs 108 that add strength and rigidity to the electronic scale 18.

Table 1 shows multiple comparative weight measurements taken with the electronic scale 18 resting on a tile floor and a carpeted floor without rubber feet on the scale 18. The measurements were taken using the same load cell 100. The thickness "T" of the top plate 11 and supporting ribs was 0.125" except around the load cell, where the thickness of the supporting ribs was 0.250". The thickness of the load cell 100 support/mounting surfaces 96, 98 (FIG. 9) was 0.375". As indicated in Table 1, with the scale 18 resting on a tile floor, the average measured weight was 146.77 lbs., with a standard deviation of 0.11595. Subsequently, with the scale 18 resting on a 0.5" carpet with 0.38" pad underneath and an additional 0.5" rug on top of the carpet, the average measured weight was 146.72 lbs., with a standard deviation of 0.16866.

TABLE 1

Thick Scale Parts Around Load Cell 0.250"

| TILE (lbs.) | CARPET (lbs.) |
|---|---|
| 146.9 | 146.7 |
| 146.7 | 147 |
| 146.9 | 146.6 |
| 146.8 | 146.7 |
| 146.6 | 146.6 |
| 146.8 | 147 |
| 146.8 | 146.5 |
| 146.7 | 146.6 |
| 146.9 | 146.8 |
| 146.6 | 146.7 |
| 0.11595 (stddev) | 0.16866 (stddev) |
| 146.77 (average) | 146.72 (average) |

Table 2 shows multiple weight measurements taken with the scale 18 on a tile floor and a carpeted floor with rubber feet on the bottom of the scale 18. The measurements were taken using the same load cell 100. The thickness "T" of the top plate 11 was 0.125" including the thickness around the load cell. As indicated in Table 2, with the scale 18 resting on a tile floor on rubber feet, the average measured weight was 146.62 lbs., with a standard deviation of 0.07888. Subsequently, with the scale 18 resting on a 0.5" carpet with 0.38" pad underneath and an additional 0.5" rug on top of the carpet, the average measured weight was 146.62 lbs., with a standard deviation of 0.04216.

TABLE 2

Thin Scale Parts Throughout 0.125"

| TILE (lbs.) | CARPET (lbs.) |
|---|---|
| 146.7 | 146.7 |
| 146.7 | 146.7 |
| 146.6 | 146.6 |
| 146.6 | 146.6 |
| 146.6 | 146.6 |
| 146.6 | 146.6 |
| 146.5 | 146.6 |
| 146.7 | 146.6 |
| 146.5 | 146.6 |
| 146.7 | 146.6 |
| 0.07888 (stddev) | 0.04216 (stddev) |
| 146.62 (average) | 146.62 (average) |

Table 3 shows multiple weight measurements taken with an off-the-shelf conventional electronic scale. As indicated in table 3, with the off-the-shelf conventional scale resting on the tile floor, the average measured weight was 165.5571 lbs., with a standard deviation of 0.20702. Subsequently, with the off-the-shelf conventional scale resting on a 0.5" carpet with 0.38" pad underneath and an additional 0.5" rug on top of the carpet, the average measured weight was 163.5143 lbs., with a standard deviation of 0.13093.

TABLE 3

Off-The-Shelf Conventional Scale

| TILE (lbs.) | CARPET (lbs.) |
|---|---|
| 165.9 | 163.5 |
| 165.5 | 163.4 |
| 165.8 | 163.7 |
| 165.4 | 163.6 |
| 165.5 | 163.6 |
| 165.4 | 163.5 |
| 165.4 | 163.3 |
| — | 163.4 |
| 0.20702 (stddev) | 0.13093 (stddev) |
| 165.5571 (average) | 163.5143 (average) |
| 2.042857 (% of difference) | 1.249345 (% of difference) |

The summary in Table 4 is a comparative illustration of the relative repeatability of each scale while resting either on a tile floor or on a carpeted floor.

TABLE 4

SUMMARY OF DATA:

| TRIAL | TILE | STDDEV | CARPET | STDDEV | TILE VS. CARPET |
|---|---|---|---|---|---|
| Heavy Scale Parts All 0.125" Except Cell Around the Load Cell 0.250" | | | | | |
| 1 | 146.77 | 0.1159 | 146.72 | 0.1686 | 0.05 |
| 2 | 146.67 | 0.0823 | 146.72 | 0.1906 | 0.05 |
| Thin Scale Parts All 0.125" | | | | | |
| 1 | 146.62 | 0.0788 | 146.62 | 0.04216 | 0.00 |
| Off-The-Shelf Conventional Scale | | | | | |
| 1 | 165.55 | 0.207 | 163.51 | 0.1309 | 2.04 |

The foregoing description was intended to provide a general description of the overall structure of several embodiments of the invention, along with a brief discussion of the specific components of these embodiments of the invention. In operating the apparatus 10, an ambulatory patient utilizes the monitoring apparatus 10 to obtain a measurement of a particular physiological parameter. For example, an ambulatory patient suffering from chronic heart failure will generally be required to monitor his or her weight as part of in-home patient managing system. Accordingly, the patient measures his or her weight by stepping onto the electronic scale 18, integrally located within the base plate 12 of the monitoring apparatus 10.

Referring now to FIG. 4, the modem 36 of the monitoring apparatus 10 will only activate if the measured weight is within a defined range such as +/−10 lbs, +/−10% or any selected predetermined value of a previous weight measurement. The patient's previous symptom free weight (dry weight) is stored in the memory 40. The dry weight is the patient's weight whenever diuretics are properly adjusted for the patient, for example. This prevents false activation of the modem 36 if a child, pet, or other person accidentally steps onto the electronic scale 18.

Upon measuring the weight, the microprocessor system 24 determines whether it is within a defined, required range such as +/−10 lbs. or +/−10% of a previously recorded weight stored in memory 40. The monitoring apparatus 10 then initiates a call via the modem 36 to the remote site 62. Communications is established between the local monitoring apparatus 10 and the remote computer 32. In one embodiment of the invention, the patient's weight is electronically transferred from the monitoring apparatus 10 at the local site 58 to the remote computer 32 at the remote site 62. At the remote site 62 the computer program compares the patient's weight with the dry weight and wellness information and updates various user screens. The program can also analyze the patient's weight trend over the previous 1-21 days. If significant symptoms and/or excessive weight changes are reported, the system alerts the medical care provider who may provoke a change to the patient's medication dosage, or establish further communication with the patient such as placing a telephone to the patient. The communication between the patient's location and the remote location may be one way or two way communication depending on the particular situation.

To establish the patient's overall condition, the patient is prompted via the output device(s) 30 to answer questions regarding various wellness parameters. An exemplary list of questions, symptoms monitored and the related numerical score is provided in Table 5 as follows:

TABLE 5

Health Check Score

| Question | Symptom | Value |
|---|---|---|
| Above Dry Weight? | Fluid accumulation | 10 |
| Are you feeling short of breath? | Dyspnea | 10 |
| Did you awaken during the night short of breath? | Paroxysmal nocturnal dyspnea | 5 |
| Did you need extra pillows last night? | Congestion in the lungs | 5 |
| Are you coughing more than usual? | Congestion in the lungs | 3 |
| Are your ankles or feet swollen? | Pedal edema | 5 |
| Does your stomach feel bloated? | Stomach edema | 3 |
| Do you feel dizzy or lightheaded? | Hypotension | 5 |
| Are you more tired than usual? | Fatigue | 2 |
| Are you taking your medication? | Medication compliance | 7 |
| Has your appetite decreased? | Appetite | 2 |
| Are you reducing your salt intake? | Sodium intake | 1 |
| Did you exercise today? | Fitness | 1 |

At the remote site 62 the medical professional caregiver evaluates the overall score according to the wellness parameter interrogation responses (as shown in Table 5). For example, if the patient's total score is equal to or greater than 10, an exception is issued and will either prompt an intervention by the medical professional caregiver in administering medication, or prompt taking further action in the medical care of the patient.

The output device(s) 30 varies based on the embodiment of the invention. For example, the output device may be a synthetic speech generator 33. As such, the wellness parameters are communicated to the patient via the electronic synthetic speech generator 33 in the form of audible speech. It will be appreciated that electronic speech synthesizers are generally well known and widely available. The speech synthesizer converts electronic data to an understandable audible speech. Accordingly, the patient responds by entering either "YES" or "NO" responses into the input device 28, which may include for example, an electronic keypad 29. However, in one embodiment of the invention, the input device may also include a generic speech recognition device such as those made by International Business Machines (IBM), Dragon Systems, Inc. and other providers. Accordingly, the patient replies to the interrogations merely by speaking either "YES" or "NO" responses into the speech recognition input device.

In embodiments of the invention that include electronic display 31 as an output device 30, the interrogations as well as the responses are displayed and/or scrolled across the display for the patient to read. Generally, the electronic display will be positioned such that it is viewable by the patient during the information exchanging process between the patient and the remote computer 32.

Upon uploading the information to the remote computer 32, the medical professional caregiver may telephone the patient to discuss, clarify or validate any particular wellness parameter or physiological data point. Furthermore, the medical professional caregiver may update the list of wellness parameter questions listed in Table 5 from the remote site 62 over the two way communication network 34. Modifications are transmitted from the remote computer 32 via modem 35, over the communication network 34, through modem 36 and to the monitoring apparatus 10. The modified query list is then stored in the memory 40 of the microprocessor system 24.

Two-Way Communication

Figure 11:
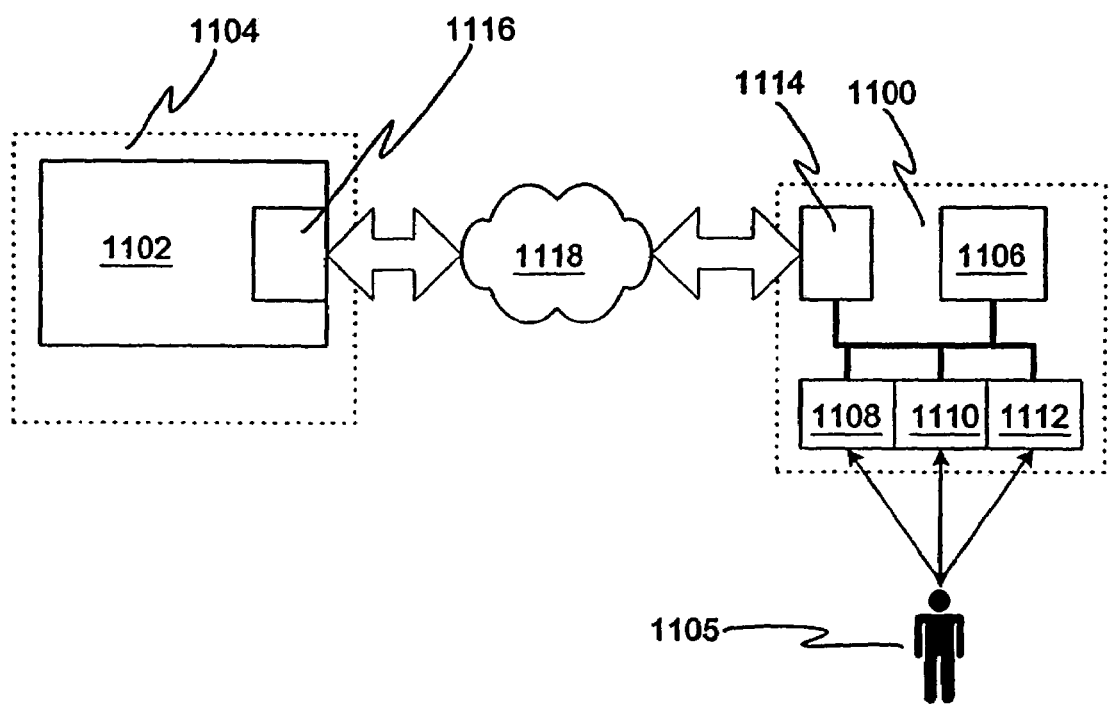
FIG. 11 illustrates a high-level depiction of a monitoring system utilizing two-way communication, in accordance with one embodiment of the present invention.

FIG. 11 is presented in furtherance of the previous discussion regarding two-way communication between the patient monitoring apparatus and the central computer. FIG. 11 is a high-level depiction of the monitoring system, and may be used as a starting point for a more detailed discussion of the two-way communication schemes.

As can be seen from FIG. 11, the system comprises a patient monitoring apparatus 1100 and a central computer 1102. The central computer 1102 is housed within a facility 1104 that is located remote from the patient monitoring apparatus 1100. For example, the patient monitoring apparatus 1100 may be located in the home of an ambulatory patient 1105, while the central computer 1102 is located in a cardiac care facility 1104.

As described previously, the patient monitoring apparatus 1100 is composed of a central processor unit 1106, which is in communication with an input device 1108, an output device 1110, and a sensor 1112. As also previously described the sensor 1112 may be a transducer used to convert a physiological measurement into a signal, such as an electrical signal or an optical signal. For example, the sensor 1112 may comprise a load cell configured with a strain gauge, arranged to determine the patient's 1105 weight; the sensor 1112 would represent the patient's 1105 weight as an electrical signal.

As discussed previously, the output device 1110 may be used to prompt the patient 1105 with questions regarding the patient's wellness. The output device 1110 may consist of a visual display unit that displays the questions in a language of the patient's 1105 choosing. Alternatively, the output device 1110 may consist of an audio output unit that vocalizes the questions. In one embodiment, the audio output unit 1110 may vocalize the questions in a language of the patient's 1105 choosing.

As discussed previously, the input device 1108 may be used to receive the patient's 1105 response to the questions posed to him/her 1105. The input device 1108 may consist of a keyboard/keypad, a set of buttons (such as a "yes" button and a "no" button), a touch-screen, a mouse, a voice digitization package, or a voice recognition package.

The patient monitoring apparatus 1100 communicates with the central computer 1102 via a network 1118; the patient monitoring apparatus 1100 uses a communication device 1114 to modulate/demodulate a carrier signal for transmission via the network 1118, while the central computer uses a communication device 1116 for the same purpose. Examples of suitable communication devices 1114 and 1116 include internal and external modems for transmission over a telephone network, network cards (such as an Ethernet card) for transmission over a local area network, a network card coupled to some form of modem (such as a DSL modem or a cable modem) for transmission over a wide area network (such as the Internet), or an RF transmitter for transmission to a wireless network. Communication may occur over a television network, such as a cable-based network or a satellite network, or via an Internet network.

A system composed as described above may be programmed to permit two-way communication between the central computer 1102 and the patient monitoring apparatus 1100.

Two-way communication may permit the central computer 1102 to upload a customized set of questions or messages for presentation to a patient 1105 via the monitoring apparatus 1100. For example, in the case where the monitoring apparatus 1100 monitors the patient's 1105 weight, a sudden increase in weight following a high sodium meal might cause the health care provider to send a customized question for presentation to the patient 1105: "Did consume any salty food in the last 24 hours?" Such a customized question could be presented to the patient 1105 the next time the patient uses the monitoring apparatus 1100 or could be presented to the patient in real time (these options are discussed in greater detail, below). Additionally, a customized message may be scheduled for delivery at certain times (such as every Friday of the week—this is also discussed in greater detail, below). Further, these customized messages may be entered on the fly or selected from a list (this is also discussed in greater detail below).

Figure 12:
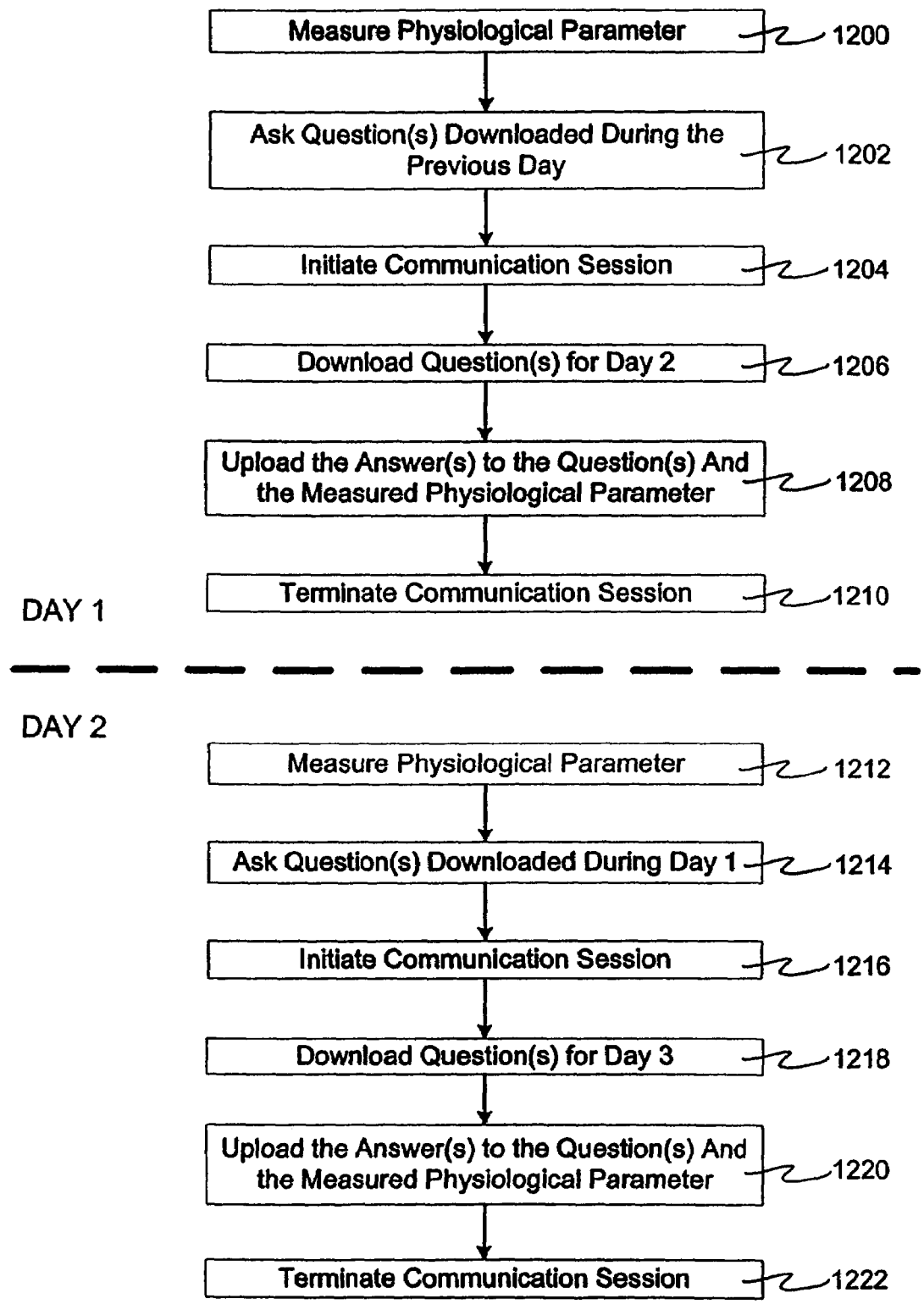
FIG. 12 depicts a flow of operation that permits two-way communication between a central computer and a monitoring apparatus.

FIG. 12 depicts a flow of operations that permits two-way communication between the central computer 1102 and the monitoring apparatus 1100. FIG. 12 presents a flow of interactions between the central computer 1102 and the monitoring apparatus 1100 on a first day (operation 1200-1210) and on a second day (1212-1222). In the discussion that follows, it will be assumed that the monitoring apparatus 1100 is formed as a scale that monitors a patient's weight, although this need not be the case. It is further assumed that the patient 1105 measures his/her weight on a daily basis (although, in principle, any frequency of measurement would operate within the bounds of this embodiment), after which a communication session is initiated between the central computer 1102 and the monitoring apparatus 1100.

On the first day, operation begins with the patient 1105 stepping on the scale, as shown in operation 1200; the patient's 1105 weight is measured, transduced, and stored by the central processing unit 1106. Next, in operation 1202, a memory device is accessed by the central processing unit 1106 for the purpose of retrieving a set of customized questions downloaded during the previous day. Each question is asked, in a one-by-one fashion, and a corresponding answer received from the patient 1105 via the input device 1108 is recorded (if the customized prompt is merely a statement, the statement is output to the patient and no answer is requested of the patient 1105). Next, in operation 1204, a communication session is initiated. The session may be initiated manually (for example, by the patient pushing a button); the session may be initiated automatically by the scale at a specific time of the day (such as at midnight, after the patient 1105 is assumed to have weighted himself/herself and recorded his/her answers to the customized wellness questions); the session may be initiated automatically by the scale upon the patient 1105 answering the final question; finally, the session may be initiated by the central computer 1102 at a specific time of the day (such as at midnight, after the patient 1105 is assumed to have weighted him/herself and recorded his/her answers to the customized wellness questions). During the communication session, customized questions to be asked to the patient 1105 the next day are downloaded by the monitoring apparatus 1100, as depicted in operation 1206. Additionally, the answers recorded in operation 1202 are uploaded to the central computer 1102, as depicted in operation 1208. Finally, in operation 1210, the communication session is terminated.

On the second day, the same set of operations takes place, with references to previous and future days now referring to "DAY 1" and "DAY 3," respectively: in operation 1214, the set of questions downloaded during the first day (in operation 1206) are asked, and the answers are recorded; similarly, in operation 1218, a set of customized questions to be asked on a third day are uploaded to the monitoring apparatus 1100.

Downloading operations (such as operations 1206 and 1218) and uploading operations (such as operation 1208 and 1220) may be influenced by the form of input device 1108 or output device 1110 chosen for use by the monitoring apparatus 1100. For example, if the output device 1110 is a visual display, then a set of data representing the text of the question is transmitted to the monitoring apparatus 1100 during the downloading operations 1206 and 1208. If, however, the output device 1110 is an audio output device, then a set of data representing a vocalization of the question may be transmitted to the monitoring apparatus 1100 during the downloading operations 1206 and 1208. In any case, the data being transmitted to the monitoring apparatus 1100 may be compressed for the sake of preservation of bandwidth. Similar considerations apply to the uploading operations 1208 and 1220, based upon the choice of input device 1108. If the input device 1108 is a set of buttons (for example, a "yes" button and a "no" button), then the data uploaded to the central computer 1102 is representative of the button that was pushed. If the input device 1108 is a voice digitization package, then the data uploaded to the central computer 1102 is representative of the digitized voice pattern from the patient 1105. As in the case of the downloading operations, the data being uploaded to the central computer 1102 may be compressed for the sake of preservation of bandwidth.

Figure 13:
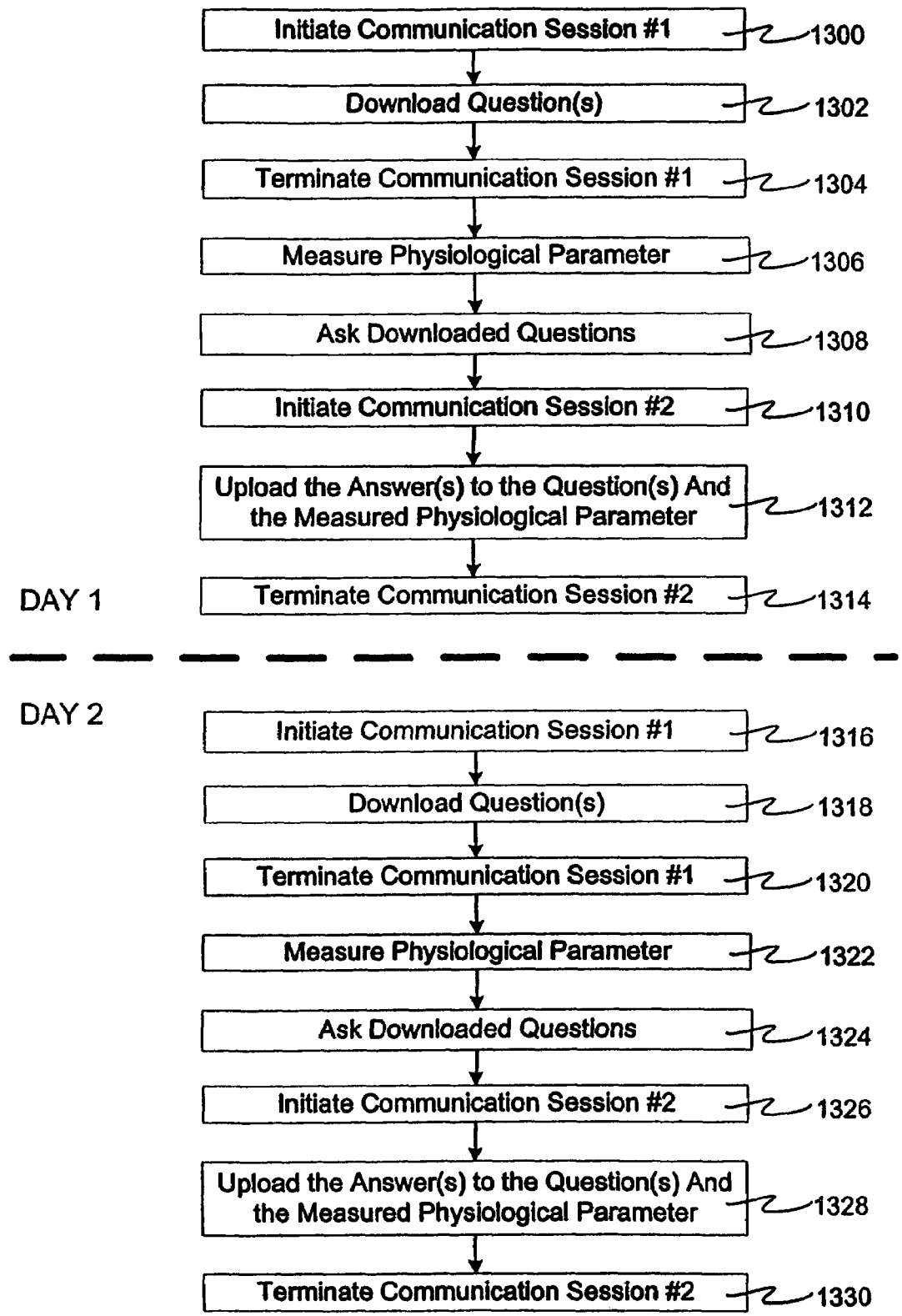
FIG. 13 depicts another flow of operation that permits two-way communication between a central computer and a monitoring apparatus.
Figure 14:
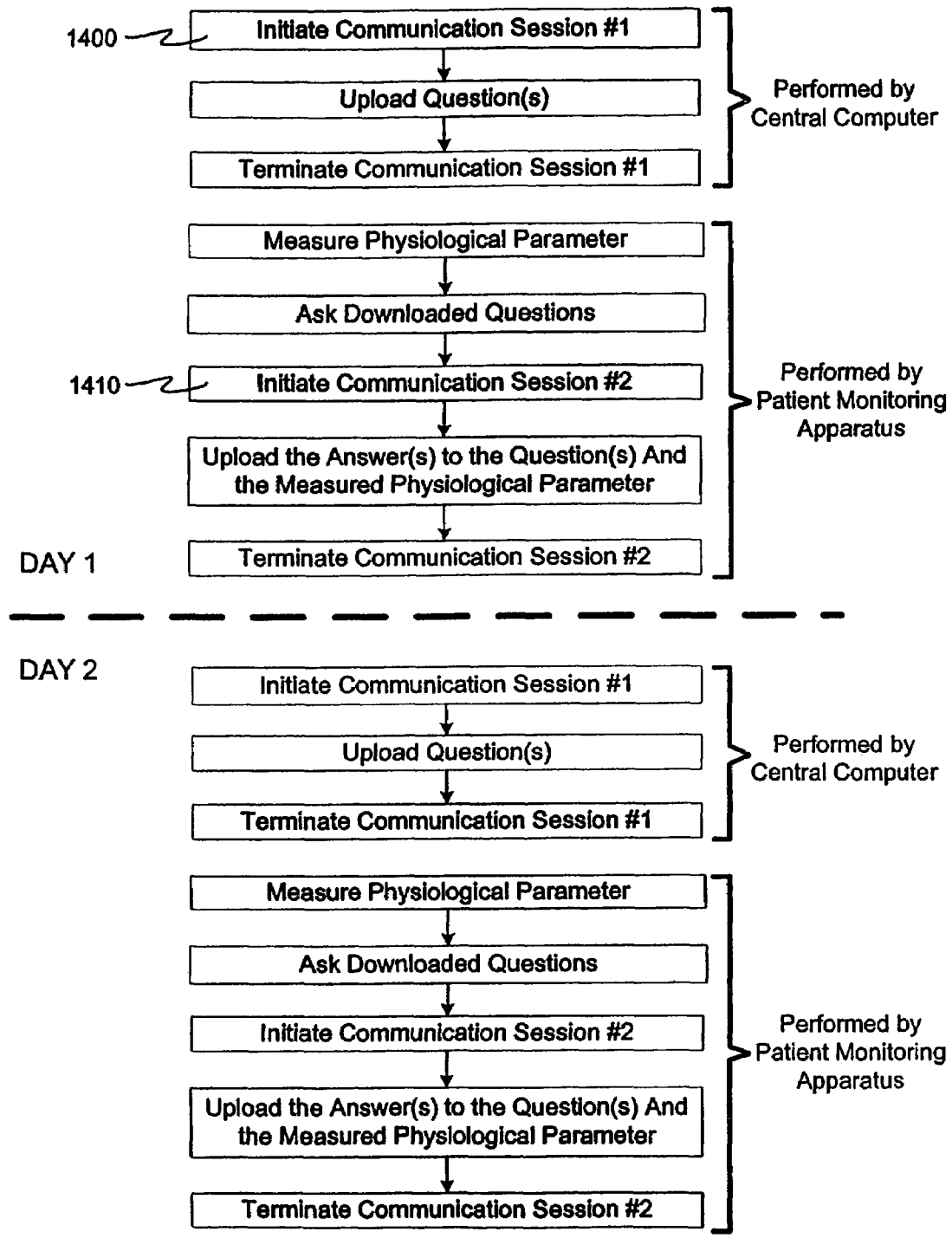
FIG. 14 depicts yet another flow of operation that permits two-way communication between a central computer and a monitoring apparatus.
Figure 15:
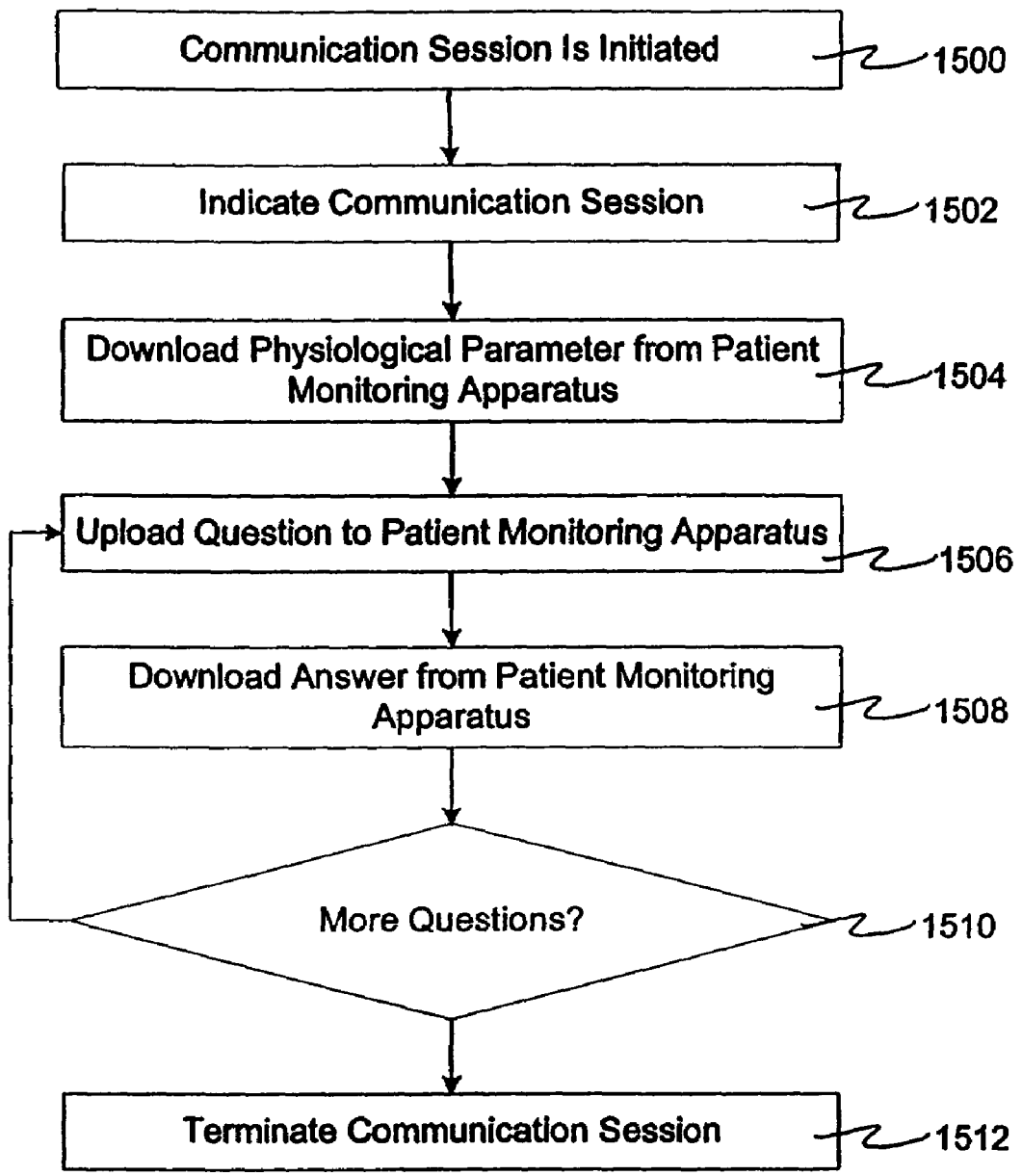
FIG. 15 depicts a flow of operation that permits real-time two-way communication between a central computer and a monitoring apparatus.

FIGS. 13, 14, and 15 depict other flows of operation for two-way communication between a central computer 1102 and a patient monitoring apparatus 1100. The considerations regarding the format of the data being uploaded and downloaded also apply to the schemes illustrated therein.

FIG. 13 depicts a flow of operations that permits two-way communication between the central computer 1102 and the monitoring apparatus 1100. FIG. 13 presents a flow of interactions between the central computer 1102 and the monitoring apparatus 1100 on a first day (operation 1300-1314) and on a second day (1316-1328). In the discussion that follows, it will be assumed that the monitoring apparatus 1100 is formed as a scale that monitors a patient's weight, although this need not be the case. It is further assumed that the patient 1105 measures his/her weight on a daily basis (although, in principle, any frequency of measurement would operate within the bounds of this embodiment).

On the first day, operation begins with a communication session between the central computer 1102 and the monitoring apparatus 1100 being initiated, as shown in operation 1300. During this communication session, a set of customized questions to be asked to the patient 1105 later in the day are downloaded by the monitoring apparatus 1100, as depicted in operation 1302. Then, in operation 1304, the communication session is terminated. The communication session initiated in operation 1300 may be initiated by the monitoring apparatus. Additionally, the session may be initiated at a time of the day that justifies the assumption that any new customized questions would have already been entered for downloading by the monitoring device 1100. At some point in the day after the termination of the communication session, the patient 1105 weighs himself on the monitoring apparatus, as shown in operation 1306, and the weight is stored by the central processor unit 1106. Next, in operation 1308, a memory device is accessed by the central processing unit 1106 for the purpose of retrieving the set of customized questions downloaded earlier in the day during operation 1302. Each question is asked, in a one-by-one fashion, and a corresponding answer received from the patient 1105 via the input device 1108 is recorded. Next, in operation 1310, a communication session is initiated. As in the scheme depicted in FIG. 12, the session may be initiated manually or automatically. During this session, the answers recorded in operation 1308 are uploaded to the central computer 1102, as depicted in operation 1312. Finally, in operation 1314, the communication session is terminated.

As can be seen from FIG. 13, the set of operations performed on the second day (operations 1316-1328) are identical to the operations performed on the first day (operations 1300-1314).

FIG. 14 depicts another flow of operations that permits two-way communication between the central computer 1102 and the monitoring apparatus 1100. The flow of operations depicted in FIG. 14 is the same as that which is shown in FIG. 13, with minor exceptions. The flow depicted in FIG. 14 is arranged such that the central computer 1102 initiates the first communication session (in operation 1400), during which a set of customized questions are downloaded by the monitoring device; however, later in the day, the monitoring device 1100 initiates the second communication session (in operation 1410), during which the patient's 1105 weight and answers to the customized questions are transmitted to the central computer 1102. This scheme has the advantage of allowing the central computer 1102 to initiate the session during which the customized questions are uploaded to the monitoring apparatus 1100, thereby ensuring that the communication session occurs after the new questions have been entered by the health care provider (if the monitoring apparatus 1100 initiates the communication session, as in FIG. 13, the session may be initiated before the new questions are entered). Just as in the scheme depicted in FIG. 13, the scheme depicted in FIG. 14 employs the same set of operations from day to day.

FIG. 15 depicts a flow of operations that permits real-time two-way communication between the central computer 1102 and the monitoring apparatus 1100. In the discussion that follows, it will be assumed that the monitoring apparatus 1100 is formed as a scale that monitors a patient's weight, although this need not be the case. It is further assumed that the patient is free to weight himself/herself at any time during the day and that the measured weight will be stored. The scheme depicted in FIG. 15 permits the patient 1105 to initiate a communication session, during which the health care provider may, via the central computer, enter questions that are posed to the patient in real-time via the monitoring apparatus 1100. The communication session does not end until the health care provider indicates that it has no further questions to ask the patient. Thus, the health care provider may adapt its questions in real-time, based upon the answers received from the patient 1105.

Operation begins with a communication session between the central computer 1102 and the monitoring apparatus 1100 being initiated, as shown in operation 1500. Next, in operation 1502, the central computer 1102 generates a visual cue on its graphical user interface to indicate that a particular patient is logged in. A health care provider/operator at the central computer 1102 is thereby made aware of his/her opportunity to prompt the patient 1105 with customized questions in real-time. Subsequently, in operation 1504, the weight of the patient 1105 is uploaded to the central computer. As mentioned earlier, the patient 1105 is assumed to have weighed himself/herself at a point in the day prior to the initiation of the communication session in operation 1500. This permits the patient 1105 to consistently measure his/her weight at a given point in the day (perhaps immediately upon waking in the morning), yet answer questions regarding his/her symptoms at a point later in the day, so that the patient 1105 has had a chance to judge his/her general feeling of health/illness before answering the questions. Of course, this is an optional feature of the invention and is not crucial. In operation 1506, a first customized question is uploaded to the monitoring apparatus. During operation 1506, a health care provider/operator may enter a question to be posed to the patient 1105; it is immediately transmitted to the monitoring apparatus 1100 and posed to the patient 1105. In operation 1508, the patient's answer is transmitted to the central computer 1102. Next, in operation 1510, the operator/health care provider at the central computer 1102 indicates whether or not any additional questions are pending. If so, control is passed to operation 1506, and the additional questions are asked and answered. Otherwise, the communication session is terminated in operation 1512.

Scheduling of Questions and Presentation of Trending Data

Figure 16:
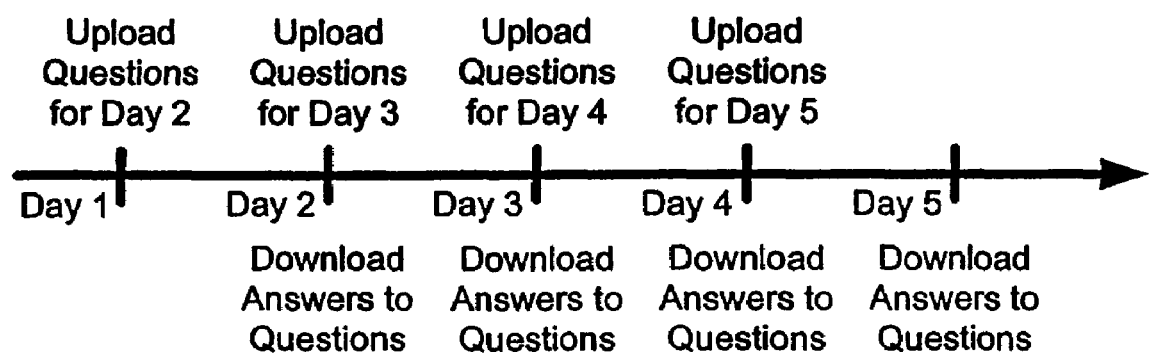
FIG. 16 depicts a scheme of asking customized questions and collecting the answers thereto.

FIG. 16 illustrates a scheme of asking customized questions and collecting the answers thereto. As can be seen from FIG. 16, a set of customized questions may be downloaded to a monitoring device 1100 on DAY N. The customized questions will be asked to the patient 1105, and the answers recorded either later in the day on DAY N or on DAY N+1 (depending upon the particular 2-way scheme employed). The answers to the customized questions are retrieved by the central computer 1102 on DAY N+1. The particular questions asked from day-to-day may vary, based upon instruction from the health care provider.

Figure 17:
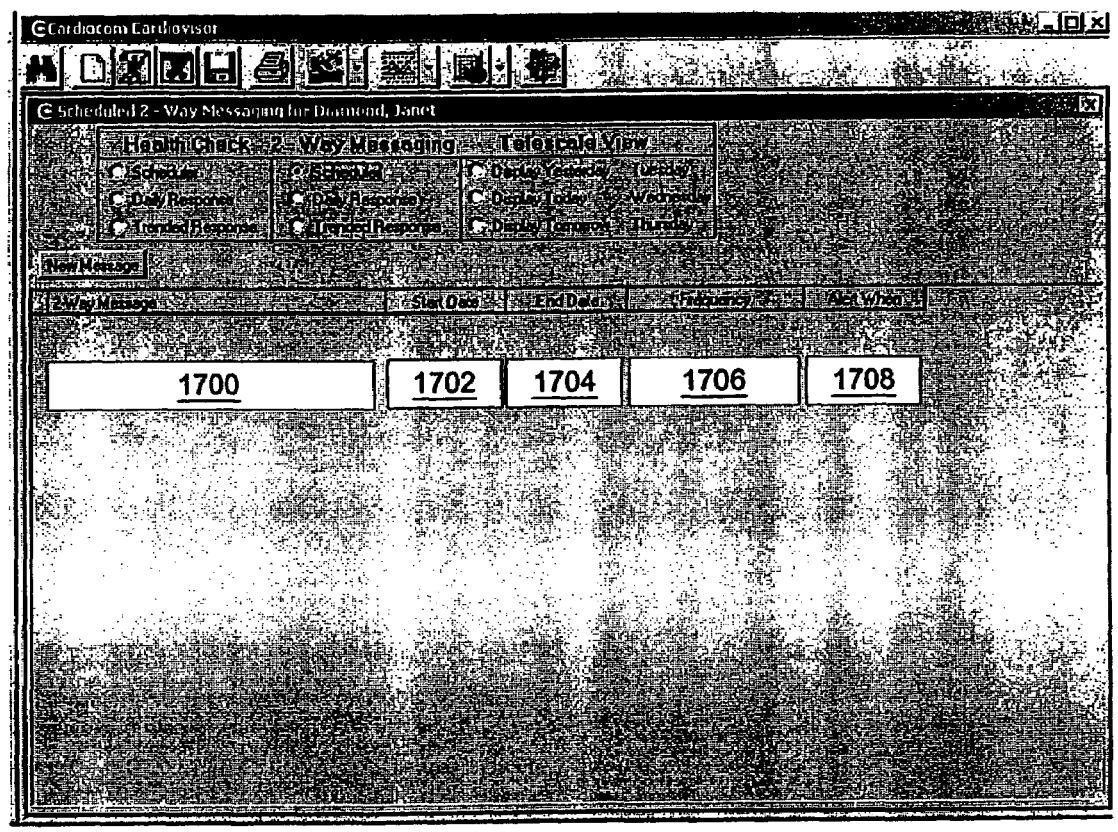
FIG. 17 illustrates a graphical user interface that may be used in conjunction with software running on a central computer for the purpose of scheduling questions to be uploaded each day to a monitoring apparatus for questioning of a patient.

FIG. 17 illustrates a graphical user interface that may be used in conjunction with software running on the central computer 1102 for the purpose of scheduling the questions to be uploaded each day to the monitoring apparatus 1100 (as illustrated by FIG. 16) for questioning of the patient 1105. As can be seen from FIG. 17, a message field 1700 is provided that permits an operator/health care provider to enter a customized message to be uploaded to the monitoring apparatus 1100. A start-date field 1702 and an end-date field 1704 define the period during which the questions are to be asked; a frequency field indicates 1706 the frequency with which the question entered in field 1700 is to be asked. For example, if the message field 1700 contained the question "Did you remember to take your medication this week?", the start-date field 1702 contained "Aug. 1, 2001," the end-date field 1704 contained "Sep. 1, 2001," and the frequency field 1706 contained "Friday," then the patient 1105 would be prompted with the question "Did you remember to take your medication this week?" on each Friday between Aug. 1, 2001 and Sep. 1, 2001. An alert field 1708 permits an operator/health care provider to define an answer that, when provided by patient 1105, sends an alert to the health care provider. For example, in the case where the question was "Did you remember to take your medication this week?", the alert field 1708 may contain the answer "No," so that the health care provider would be alerted if the patient 1105 indicated that he/she had failed to take his/her medication during the week.

The data entered via the graphical user interface depicted in FIG. 17 is stored in a database. The data may be organized based upon dates for transmission to the monitoring device 1100, so that all of the questions to be uploaded to the monitoring device 1100 on a given day may be easily acquired. The data may be sorted other ways, as well. For example, the data may be sorted based upon which questions were asked on which days, so that a presentation of the questions posed to a patient on a given day (or set of days) and the corresponding answers thereto may be easily developed. A graphical user interface that provides such a presentation is depicted in FIG. 18.

Figure 18:
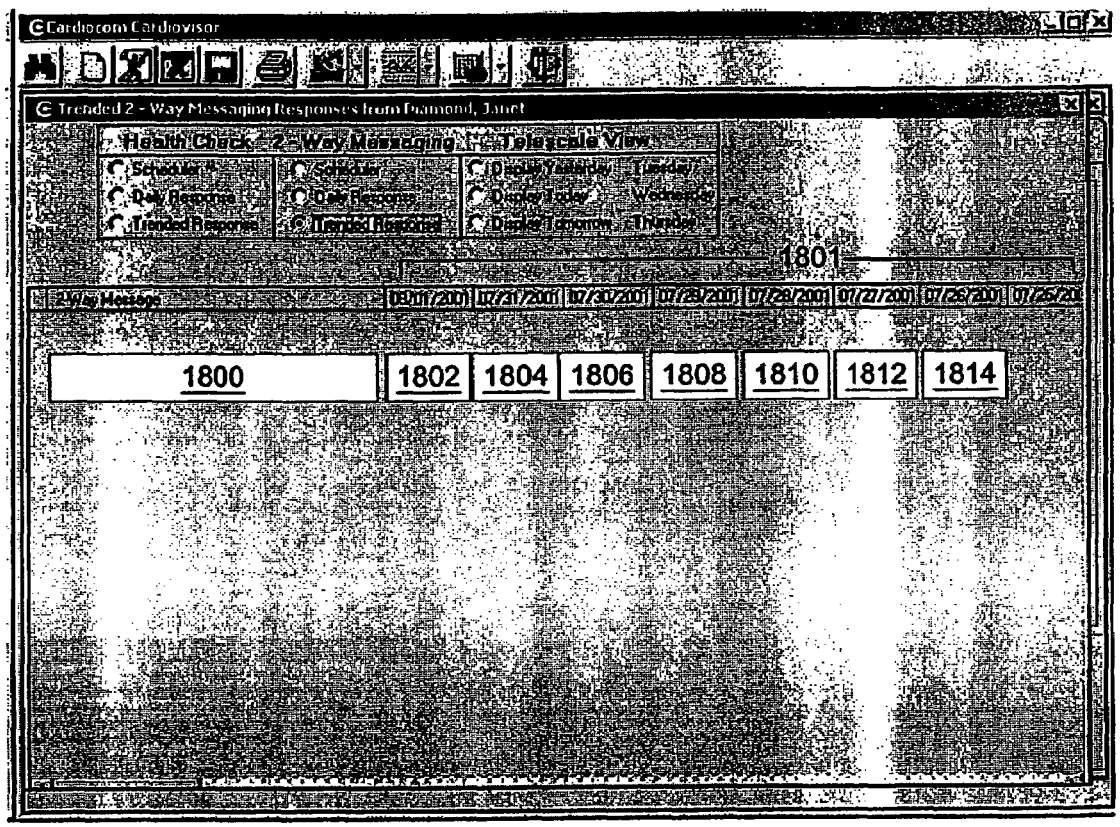
FIG. 18 illustrates a graphical user interface that may be used in conjunction with software running on a central computer for presenting a set of trending data.

FIG. 18 depicts a graphical user interface that presents all of the customized questions presented to a patient over a particular duration and all of the corresponding answers for each day. This sort of information is referred to as "trending data," because it permits a health care provider to quickly determine if a particular symptom began regularly exhibiting itself on a certain day, or if a particular symptom is randomly exhibited. As can be seen from FIG. 18, a message field 1800 is provided which presents a customized question that was asked during the timeframe indicated by the date bar 1801. Under each date presented in the date bar 1801 is an answer field 1802-1816, which presents the patient's 1105 answer to the question presented in the message field 1800. If a particular question was not asked on a given day, the graphical user interface may so indicate. For example, an answer field 1802-1816 may be grayed out on a particular day if the question was not asked, or an answer field may be highlighted on days in which the particular question was asked. As described earlier, the data used to populate fields 1800-1816 is retrieved from a database containing each of the questions asked on a given day and each of the corresponding answers.

Other reporting schemes and graphical user interfaces are taught in U.S. application Ser. No. 09/399,041 filed on Sep. 21, 1999, entitled "MEDICAL WELLNESS PARAMETERS MANAGEMENT SYSTEM, APPARATUS AND METHOD," which is hereby incorporated by reference in its entirety.

Collapsible Scale/Carpet-Spike Pads

Figure 19:
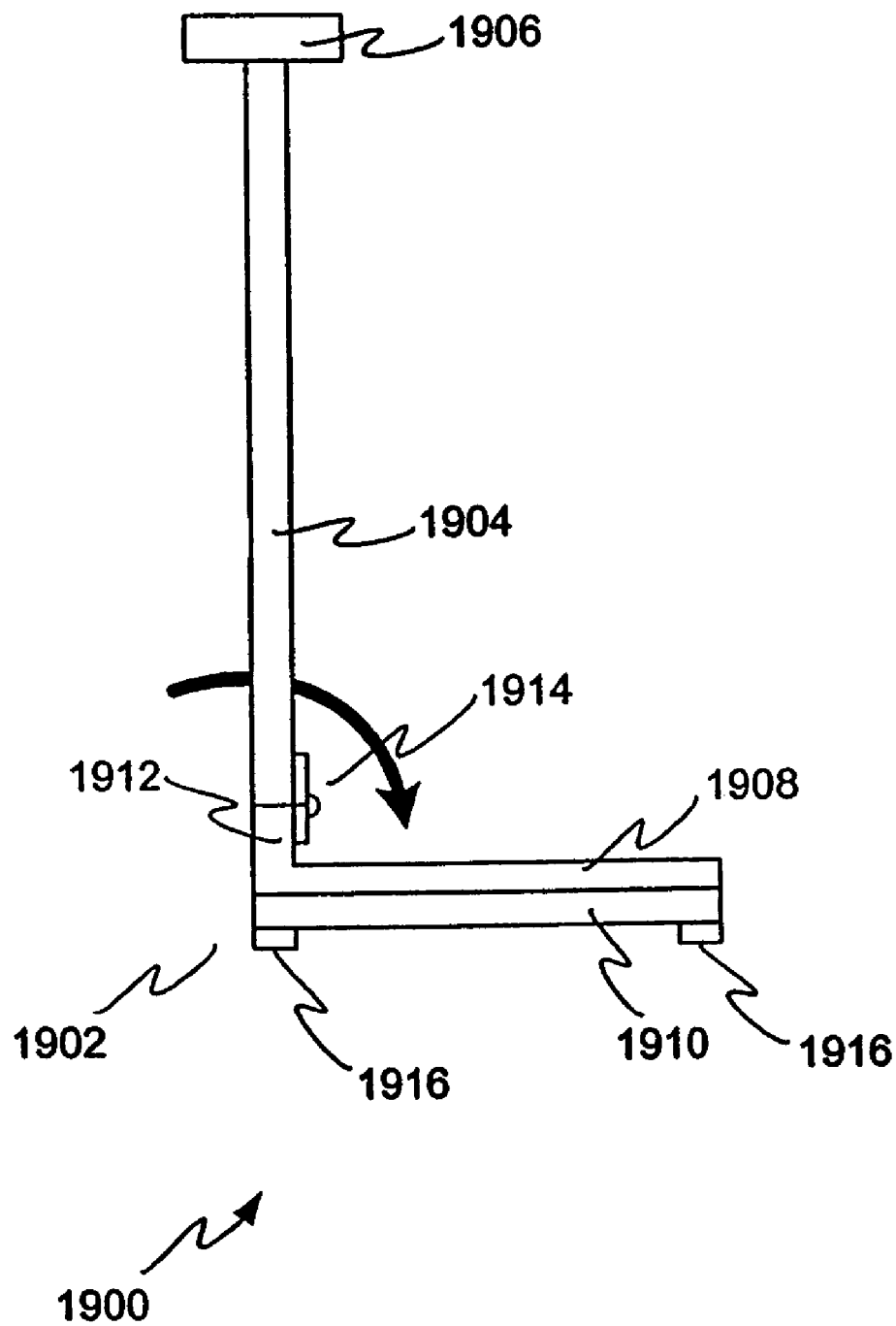
FIG. 19 depicts a collapsible scale with carpet-spike pads, in accordance with one embodiment of the invention.

FIG. 19 depicts a collapsible scale 1900 with integrated carpet-spike pads, in accordance with one embodiment of the present invention. As can be seen from FIG. 19, a collapsible scale 1900 is comprised of a base 1902, upon which a patient 1105 stands in order to weigh himself/herself. Perpendicular to the base 1902 is a support member 1904 which elevates a housing 1906 at about waist level. The housing 1906 may contain an input device, an output device, a processor, and a communication device. The support member 1904 is coupled to the base 1902 via a hinge 1914. The hinge 1914 enables the support member 1904 to fold into a position approximately parallel (though not necessarily coplanar) with the base 1902, thereby permitting the scale 1900 to fit easily (and in one piece) into a box suitable for shipping. Another advantage of the collapsible embodiment is that it relieves the patient 1105 of having to assemble the scale at his/her home.

The base 1902 may be composed of top plate 1908, upon which the patient 1105 stands, and a base plate 1910. The hinge 1914 may be coupled to the support member 1904 and the top plate 1908, so that if the patient leans upon the housing 1906, the force is conducted down the support member 1904, though the hinge 1914, and to the top plate 1908, thereby preserving the validity of the weight measurement. Alternatively, the top plate 1908 may have member 1912 rigidly coupled thereto. In such a case, the hinge 1914 may be coupled between the support member 1904 and the rigidly coupled member 1912.

In one embodiment of the scale 1900, a plurality of carpet-spike pads 1916 are attached to the bottom of the base 1902. A carpet-spike pad 1926 is a disk with a plurality of spikes that protrude downwardly therefrom. The carpet-spike pads 1916 improve the stability of the scale 1900 upon carpet-like surfaces, thereby enhancing the accuracy and repeatability of measurements taken therewith. The carpet-spike pads 1916 may be attached to the base 1902 by an adhesive, by force fit, or may be integrated into the base 1902 itself.

Question Hierarchies

Figure 20:
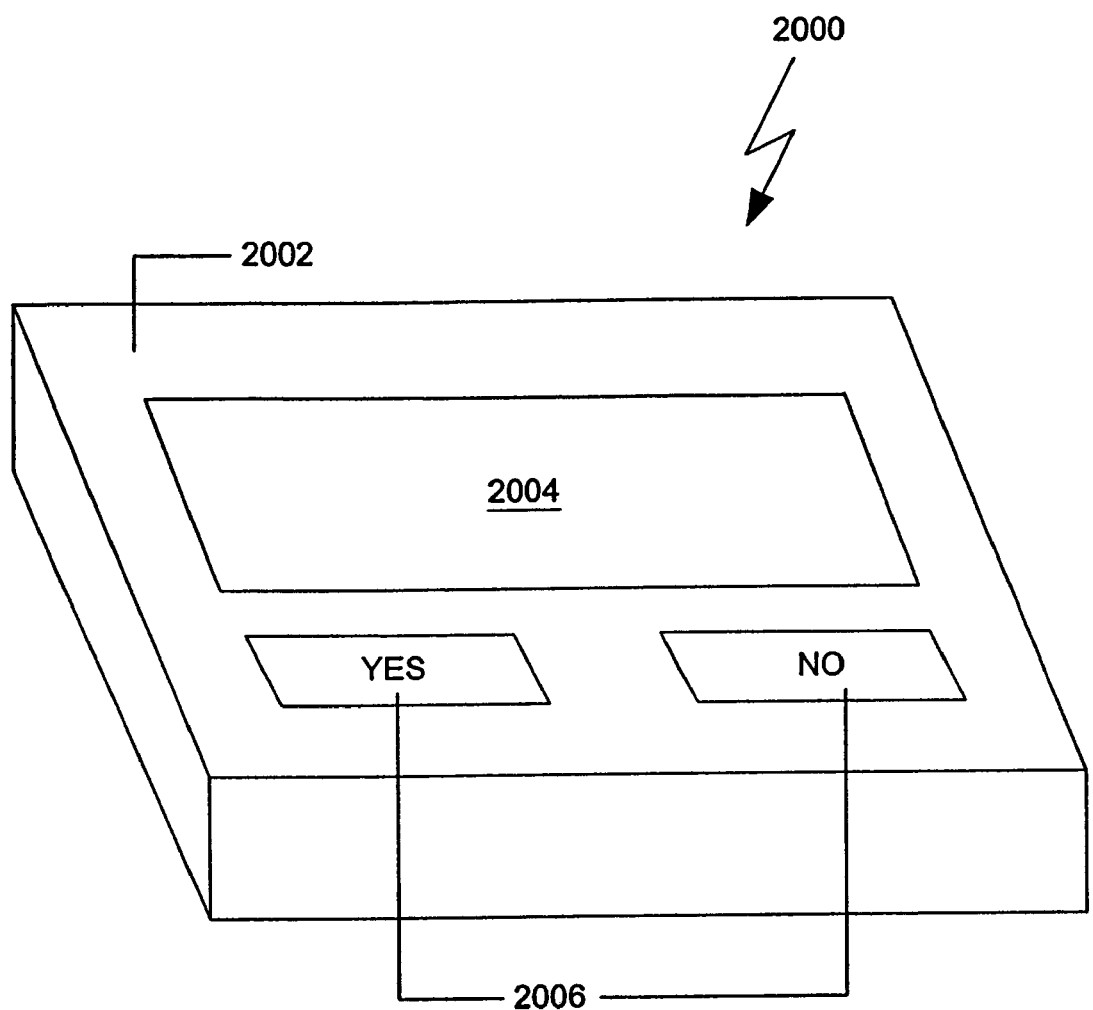
FIG. 20 depicts an embodiment of the present invention, in which a physiological parameter-measuring device is an optional component.

FIG. 20 depicts an embodiment of the patient monitoring apparatus 2000, in which the housing 2002, the output device 2004, and the input device 2006 stand alone as a complete unit. (A physiological parameter-measuring unit, such as a scale, is not required to interface with the unit 2000, but may be added). As in other embodiments, circuitry for operation of the device is held within the housing 2000. The output device 2002 may be a display, such as an LCD screen, and may include an audio output unit. The input device 2006 is depicted as two buttons, a "YES" button and a "NO" button. One skilled in the art understands that the input device may be a keypad, a mouse, a button, a switch, a light pen, or any other suitable input device. In one embodiment of the invention, the input and output devices 2004 and 2006 are combined into a touch-screen device.

The patient monitoring apparatus 2000 of FIG. 20 may be programmed to contain a plurality of question hierarchies, each of which relates to a health-related symptom. Each hierarchy contains a set of questions. Each question in a given hierarchy is aimed at characterizing a particular symptom in a particular way. Certain questions within a hierarchy may be deemed moot (and thus will not be asked) in light of a patient's answer to a previous question. Details regarding question hierarchies will be discussed in greater detail, below.

By programming the patient monitoring apparatus 2000 to contain a plurality of question hierarchies, the unit 2000 attains great flexibility as a tool for monitoring chronic diseases of many varieties. A particular chronic disease may be monitored by asking questions about symptoms associated with the disease. Thus, for example, the unit 2000 may be made to monitor the health status of a patient with chronic obstructive pulmonary disease (COPD) by querying the patient, using questions extracted from question hierarchies relating to symptoms associated with COPD. The same unit 2000 may be used to monitor a patient with diabetes by asking questions extracted from a different set of question hierarchies, which are related to symptoms associated with diabetes.

Figure 21:
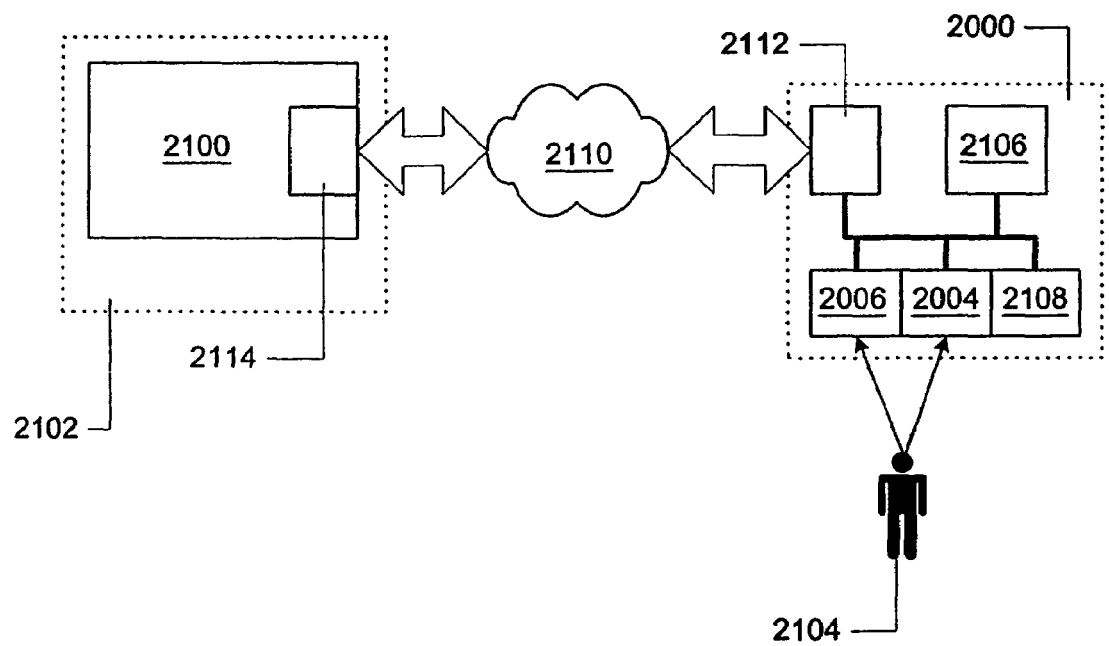
FIG. 21 depicts an embodiment of a system, in which a physiological parameter-measuring device is an optional component.

FIG. 21 is a high-level depiction of a monitoring system employing the embodiment 2000 depicted in FIG. 20, and may be used as a starting point for a more, detailed discussion of the patient monitoring apparatus 2000.

As can be seen from FIG. 21, the system comprises a patient monitoring apparatus 2000 and a central computer 2100. The central computer 2100 is housed within a facility 2102 that is located remote from the patient monitoring apparatus 2000. For example, the patient monitoring apparatus 2000 may be located in the home of an ambulatory patient 2104, while the central computer 2100 is located in a health care facility 2102.

As described previously, the patient monitoring apparatus 2000 is composed of a central processor unit 2106, which is in communication with an input device 2006, an output device 2004, and a memory device 2108. The memory device 2108 has a plurality of question hierarchies stored within it, as discussed more fully, below.

As discussed previously, the output device 2004 may be used to prompt the patient 2104 with questions regarding the patient's wellness. The output device 2004 may consist of a visual display unit that displays the questions in a language of the patient's 2104 choosing. Alternatively, the output device 2004 may consist of an audio output unit that vocalizes the questions. In one embodiment, the audio output unit 2004 may vocalize the questions in a language of the patient's 2104 choosing.

The patient monitoring apparatus 2000 communicates with the central computer 2100 via a network 2110; the patient monitoring apparatus 2000 uses a communication device 2112 to modulate/demodulate a carrier signal for transmission via the network 2110, while the central computer uses a communication device 2114 for the same purpose. Examples of suitable communication devices 2112 and 2114 include internal and external modems for transmission over a telephone network, network cards (such as an Ethernet card) for transmission over a local area network, a network card coupled to some form of modem (such as a DSL modem or a cable modem) for transmission over a wide area network (such as the Internet), or an RF transmitter for transmission to a wireless network.

A system composed as described above may be programmed to carry on periodic (e.g., daily) questioning of a patient 2104, with respect to the patient's 2104 perception regarding his or her own status vis-à-vis a particular set of symptoms. For example, a patient suffering from COPD is likely to experience shortness of breath, both during the day and during the night (amongst many other symptoms). Thus, the system may question the patient 2104 about his own perceptions regarding his shortness of breath. The questions used to determine the patient's 2104 judgment about his own shortness of breath during the day are contained in a first question hierarchy. Similarly, questions related to the patient's 2104 shortness of breath during the night are contained in a second question hierarchy.

The first hierarchy, which is related to shortness of breath during the day, may be structured as follows:

TABLE 5

Question Hierarchy: Shortness of Breath During the Day

| | |
|---|---|
| Question #1 | Are you feeling more short of breath? |
| Question #2 | Do you feel more short of breath in response to physical exertion? |
| Question #3 | Do you feel more short of breath during periods of rest? |
| Question #4 | Does stress make you feel more short of breath? |

Each of the questions in the hierarchy is related to day-time shortness of breath. The first question is broadly focused, simply asking "Are you feeling more short of breath?" Clearly, if the patient 2104 were to answer "no" to such a question, the remainder of the questions would be unnecessary. Thus, the system may be designed to prevent the remaining questions from being asked (this will be discussed in greater detail, below). Question #2 asks a question that is more particularized than question #1: "Do you feel more short of breath in response to physical exertion?" An affirmative answer to this question is more serious, and provides more particularized information, than an affirmative answer to the broader query presented in question #1. Although not essential, each question hierarchy may be constructed in accordance with this paradigm: (1) a negative answer to a preceding questions negates the need to ask any additional questions in the hierarchy; (2) successive questions relate to increasingly more particularized aspects of a given symptom; and (3) successive questions relate to an increasing severity level of a given symptom.

Figure 22:
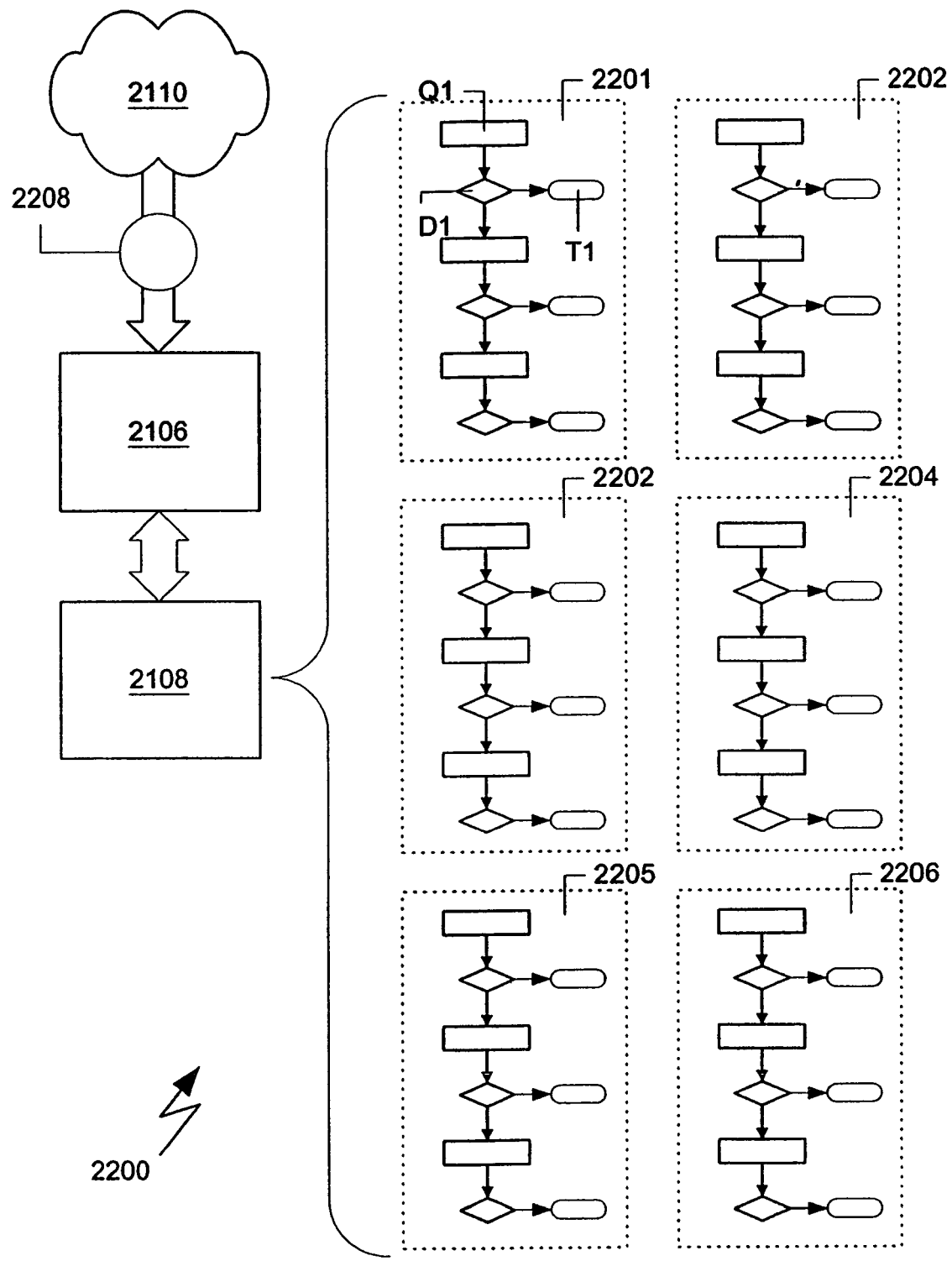
FIG. 22 depicts a memory device programmed with a set of question hierarchies.

FIG. 22 depicts the partial contents of the memory device 2108 of FIG. 21. As can be seen from FIG. 21, the memory device 2108 is programmed with a set of question hierarchies 2200. In the example depicted in FIG. 22, the memory device is programmed with six question hierarchies 2201, 2202, 2203, 2204, 2205, and 2206 (collectively referred to as "the set of question hierarchies 2200"). As described previously, each hierarchy relates to a symptom condition to be monitored, meaning that the number of question hierarchies stored in the memory device 2108 is dependent upon the number of symptoms to be monitored.

Hierarchy 2201 has a basic structure that includes a first question Q1, followed by a first decision point D1. At decision point D1, the patient monitoring apparatus 2000 decides whether or not to ask the subsequent question, Q2. For example, Q1 may be a question that reads "Are you feeling more short of breath?" If the patient 2104 answers "no," this answer is analyzed at decision point D1, and the questioning terminates at terminal point T1. Otherwise, the questioning continues with the next question, Q2, and the process continues.

Each of the hierarchies 2200 depicted in FIG. 22 possesses the above-recited structure, although other structures are possible, some of which are described below. One skilled in the art understands that although each hierarchy 2200 is depicted as consisting of three questions, a hierarchy may consist of any number of questions, including a single question.

As depicted in FIG. 22, the memory device 2108 is in data communication with the monitoring device's 2000 microprocessor 2106, which, in turn, is in data communication with a remote computer 2100 (not depicted in FIG. 22) via a network 2110 and via a communication device 2112 (also not depicted in FIG. 22). The remote computer 2100 transmits a symptom identifier 2208 to the monitoring device's 2000 microprocessor 2106. The symptom identifier 2208 corresponds to a question hierarchy 2200. For example, a symptom identifier with a value of "1" may correspond to hierarchy 2201, while a symptom identifier with a value of "2" corresponds to hierarchy 2202, etc. The microprocessor 2106 responds to having received a symptom identifier 2202 by executing the corresponding hierarchy (i.e., asking a question within the hierarchy, and deciding whether or not to ask a subsequent question therein). Thus, the patient monitoring device 2200 may be made to execute n number of question hierarchies by transmitting to it n number of symptom identifiers.

Given that a known set of symptoms are correlated with any given chronic disease, the patient monitoring device 2000 may be tailored to monitor the health status of a patient 2104 with a particular disease by executing question hierarchies 2200 relating to symptoms corresponding with the patient's 2104 particular disease. Thus, the remote computer 2100 may be programmed with software that presents a menu for each patient 2104. The menu allows the health care provider to select from among a set of chronic diseases. Based upon the selected chronic disease, the remote computer 2100 transmits one or more symptom identifiers (which correspond to symptoms known to accompany the selected disease) to the patient monitoring apparatus 2000. The remote computer 2100 receives the patient's 2104 responses, and scores the response in accordance with a scoring algorithm, discussed in detail below. Based upon the outcome of the score, an exception report may be generated, meaning that a health care provider will be notified of the patient's possible need for assistance. Alternatively, the remote computer 2100 may be programmed to transmit an e-mail message or a numeric page to communicate the information concerning the patient 2104. In principle, any data transmission communicating the patient's 2104 potential need for assistance may be transmitted.

In certain situations, it may be desirable for the patient monitoring device 2000 to obtain information regarding a physiological parameter. For example, if a particular chronic disease is associated with a fever, the patient monitoring device may want to know information concerning the patient's 2104 body temperature. Two general approaches exist for gaining information concerning a physiological parameter. The monitoring system 2000 may be adapted for interfacing with a physiological parameter-measuring unit, as has been disclosed with reference to other embodiments of the invention. The parameter-measuring unit can then directly measure the physiological parameter and transmit the data to the central computer 2100. Many times, this is an appropriate approach. Accordingly, according to one embodiment of the invention, the microprocessor 2106 may interface with a physiological parameter-measuring device, such as a scale or a thermometer, as previously described herein. On the other hand, oftentimes it is possible to ask the patient to measure the parameter for himself (e.g., take his own temperature). This approach has an advantage, in that the cost of obtaining the information is minimized. This approach is particularly useful when an exact measurement of a physiological parameter is not as useful as simply knowing whether the parameter crosses some threshold. Under these circumstances, the cost of directly obtaining precise information may outweigh the financial benefit of knowing such information. Thus, as depicted in FIG. 23, a question hierarchy 2200 may be designed to ask a patient whether one of his physiological parameters exceeds a threshold, T.

Figure 23:
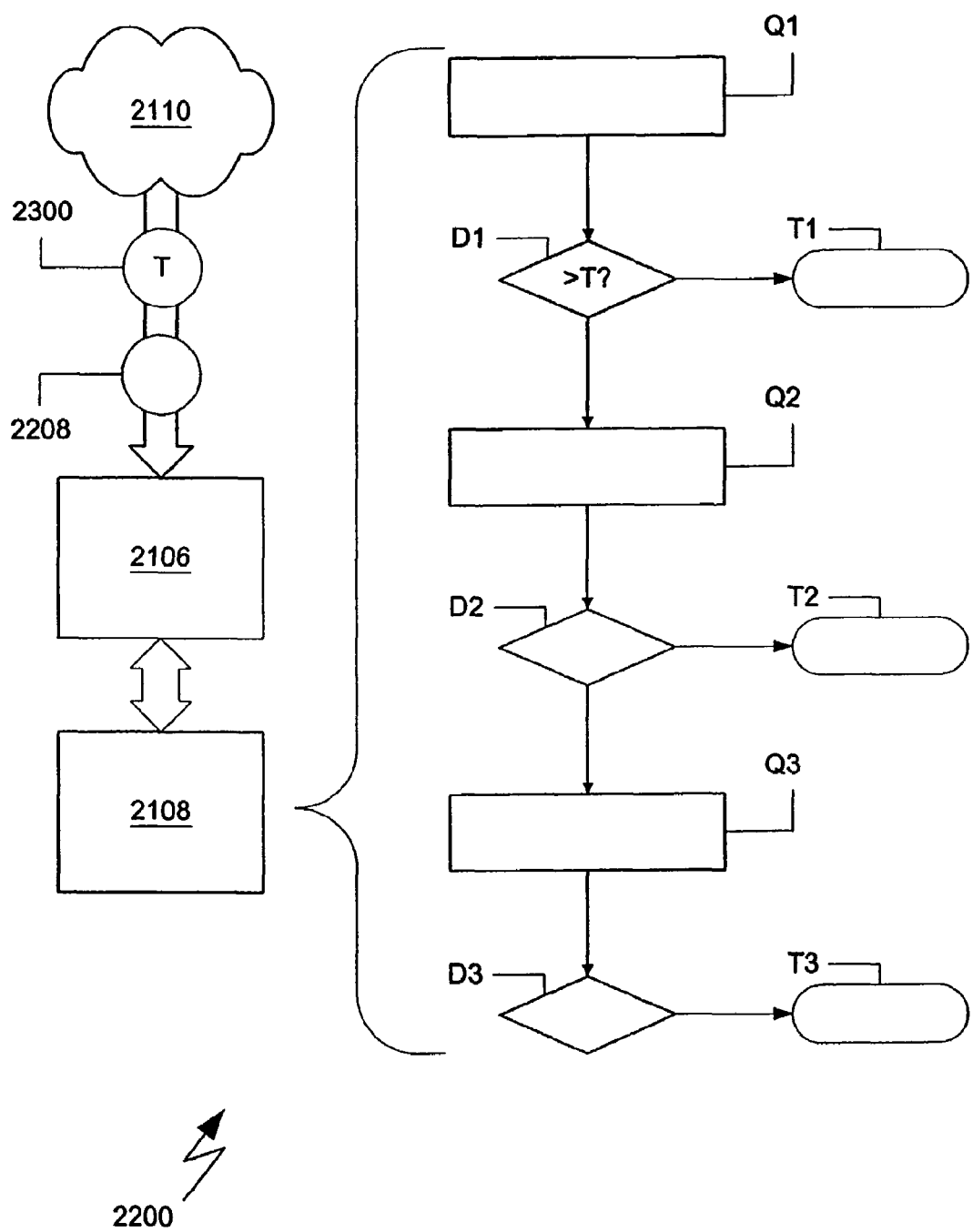
FIG. 23 depicts a particular question hierarchy logical structure, according to one embodiment of the present invention.

The question hierarchy 2200 depicted in FIG. 23 is similar to the question hierarchies 2200 discussed with reference to FIG. 22. The question hierarchy 2200 corresponds to a symptom identifier 2208, which is transmitted to the patient monitoring device 2000 by a remote computer 2100. The hierarchy 2200 possesses several questions Q1, Q2, and Q3, some of which may go unasked, if a decision point D1, D2, or D3 terminates the flow of questioning by transferring execution flow to a terminal point T1, T2 or T3. Of particular note in the question hierarchy 2200 of FIG. 23 is the first question, Q1, and the first decision point D1. The first question, Q1, asks the patient 2104 if a particular physiological parameter of his exceeds a given threshold, T. The value represented by T is transmitted to the patient monitoring device 2000 by the remote computer 2100, as is depicted by threshold datum 2300. Therefore, to invoke this particular hierarchy 2200, the remote computer should transmit both a symptom identifier 2208 and a threshold datum 2300. In response, the patient monitoring device 2000 responds by asking the patient 2104 if his particular physiological parameter exceeds the threshold, T. Next, as is depicted by decision point D1, the patient monitoring device 2000 determines whether or not to proceed with further questions, on the basis of whether or not the parameter exceeded the threshold, T.

Another situation likely to arise in the context of monitoring a patient 2104 with a chronic illness is that the patient 2104 is to be queried regarding his faithfulness to a prescribed health care regimen. For example, if the patient 2104 is a diabetic, the patient is likely to be on a strict diet. The patient monitoring device 2000 may be programmed to ask the patient 2104 if he has been following his diet. If the patient 2104 answers "yes," the device 2000 may respond by praising the patient 2104—a tactic that may be particularly advantageous for young patients. On the other hand, if the patient 2104 answers "no," the device 2000 may respond by reminding the patient 2104 to adhere to his diet.

Figure 24:
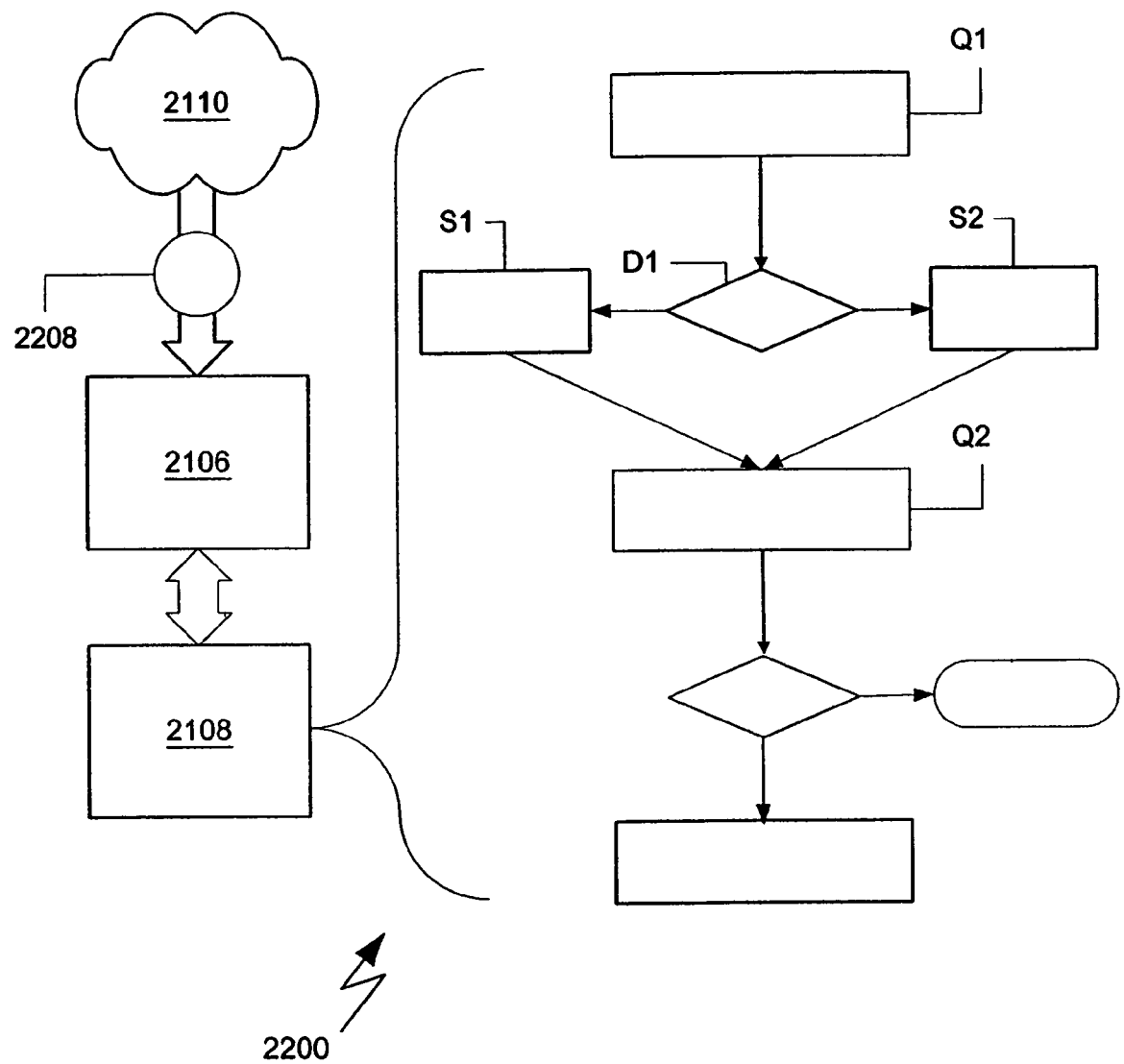
FIG. 24 depicts another question hierarchy logical structure, according to one embodiment of the present invention.

FIG. 24 depicts a question hierarchy 2200 designed to achieve the results of praising a patient 2104 for adhering to a prescribed regimen, or reminding the patient 2104 of the importance of adhering thereto. Of particular note in the question hierarchy 2200 depicted in FIG. 24 is the first question, Q1. The first question, Q1, asks the patient 2104 if he has been adhering to a health care regimen (such as, a diet or a medication regimen). Next, at decision point D1, flow of execution is adjusted based upon whether or not the patient 2104 has been adhering to the regimen. If the patient 2104 has been adhering to the regimen, the patient 2104 is presented with a statement, S1, praising the patient. Otherwise, the patient 2104 is presented with a statement, S2, reminding the patient 2104 to adhere to his regimen. In either event, execution flow is passed to the second question, Q2, and hierarchy execution continues in accordance with the flow described with reference to FIG. 22.

Figure 25:
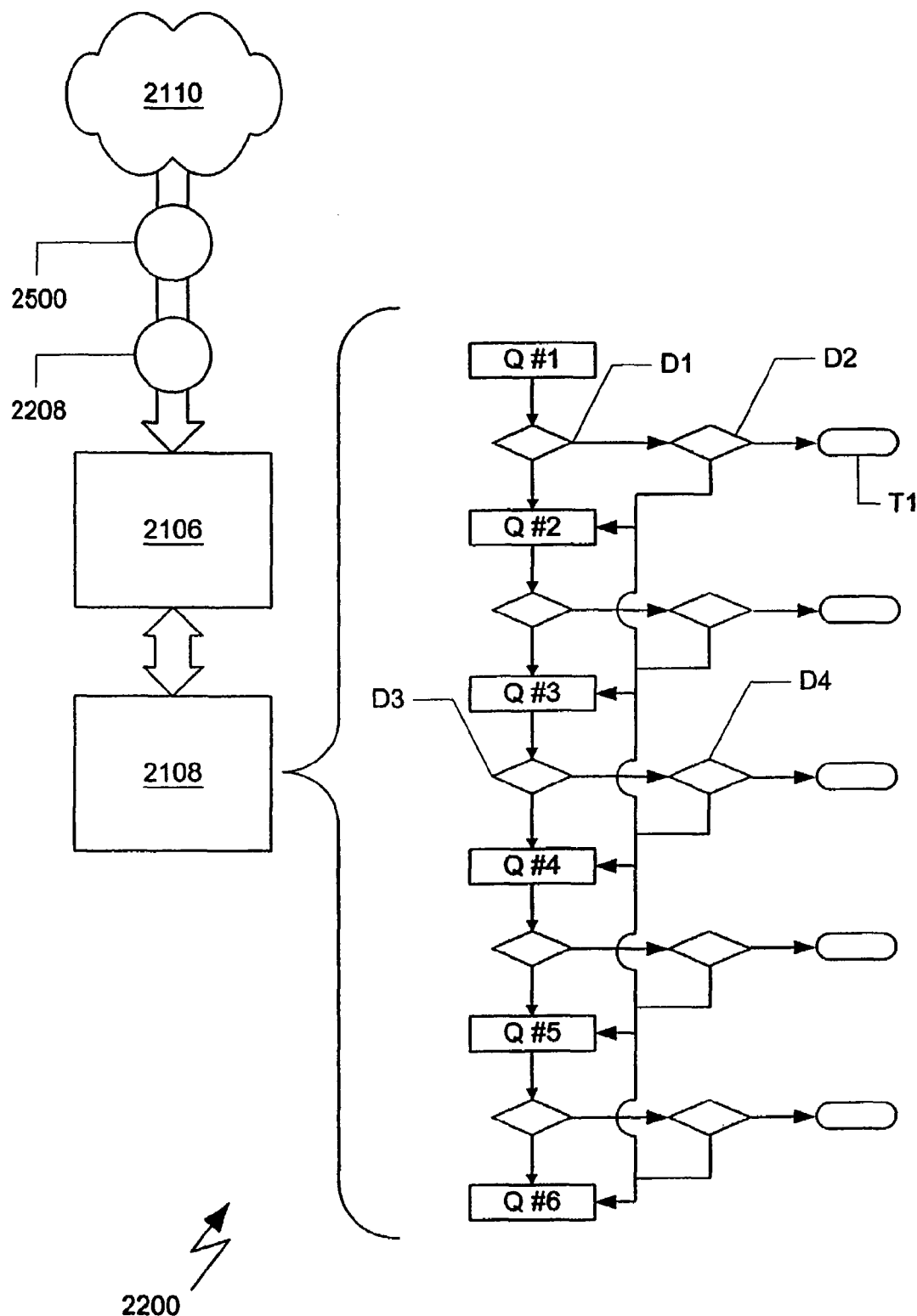
FIG. 25 depicts another question hierarchy logical structure, according to one embodiment of the present invention.

FIG. 25 depicts a question hierarchy 2200 that has been modified to permit the remote computer 2100 to command specific questions within the hierarchy 2200 to be asked, regardless of any answer that may have been previously given by the patient 2104. To achieve this result, the remote computer 2100 should transmit a symptom identifier 2208 corresponding to the question hierarchy 2200. Additionally, a question set 2500 should be transmitted. The question set 2500 may define a set of questions to be forced "on." For example, the question set 2500 may be {3, 5}, meaning that questions 3 and 5 are to be asked, no matter what the patient 2104 has previously answered.

Continuing the discussion assuming that a question set 2500 of {3, 5} had been transmitted, execution of the hierarchy commences with the asking of the first question, Q1. Next, at decision point D1, the patient's 2104 answer to the first question is assessed to determine whether the subsequent question in the hierarchy should be asked. If the answer is such that ordinarily none of the remaining questions should be asked, execution would typically flow to terminal point T1. However, in this embodiment, a second decision point, D2, is interposed between decision point D1 and terminal point T1. At the second decision point, D2, it is determined whether the question set 2500 contains a question number that is higher than the question number that was just asked. In the case of the present example, the question set 2500 contains two such question numbers, because question numbers 3 and 5 are higher than the present question number, 1. If the question set 2500 does contain a question number that is higher than the question number just asked, then execution flows to the smallest such question number (in this case, question number 3, Q3). Thereafter the process repeats, thereby ensuring that each of the question numbers in the question set will be asked.

Figure 26:
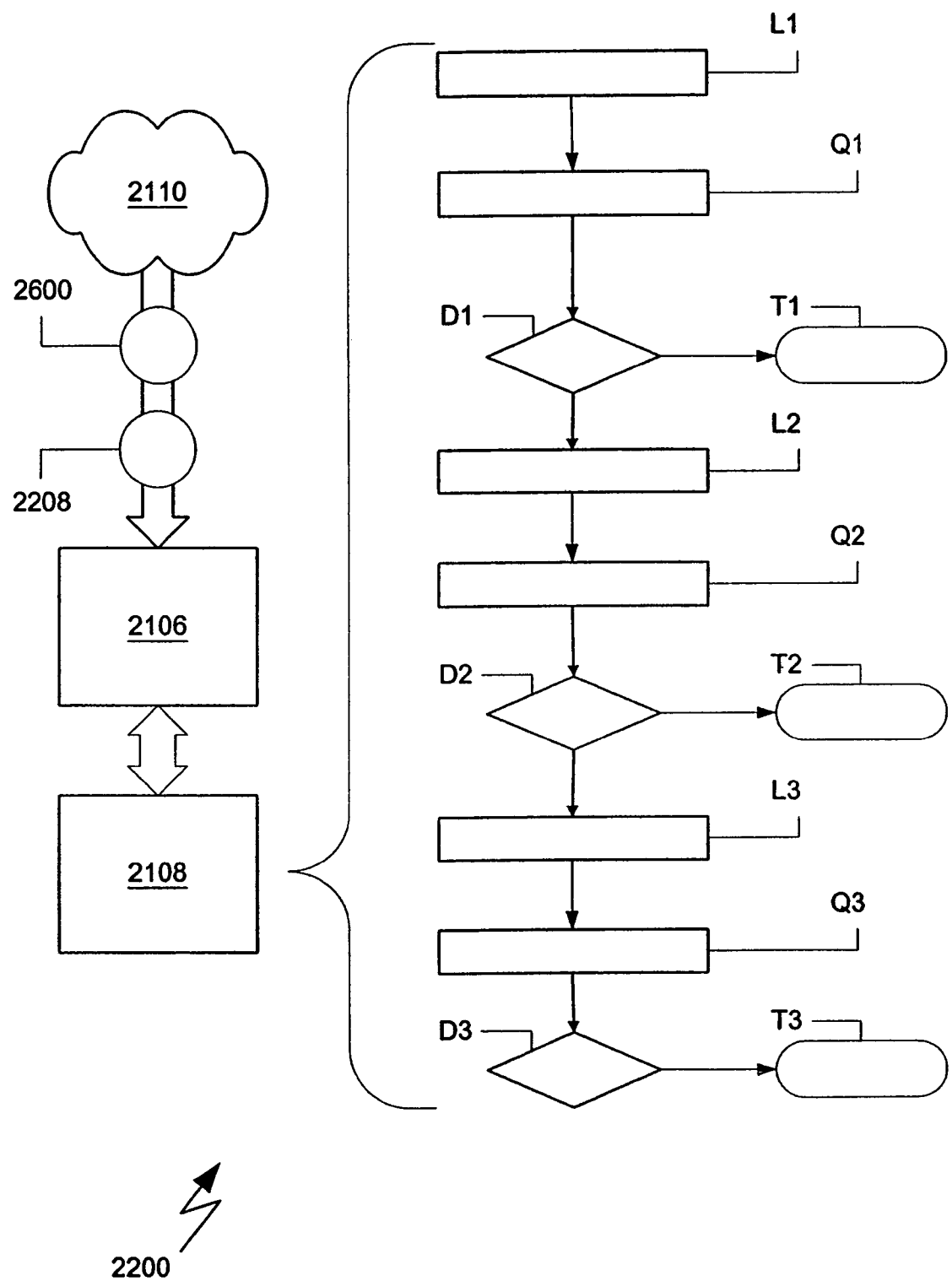
FIG. 26 depicts yet another question hierarchy logical structure, according to one embodiment of the present invention.

FIG. 26 depicts a question hierarchy 2200 that has been modified to permit the remote computer 2100 to command a specific sequence in which the questions within the hierarchy 2200 should be asked. To achieve this result, the remote computer 2100 should transmit a symptom identifier 2208 corresponding to the question hierarchy 2200. Additionally, a sequence set 2600 should be transmitted. The sequence set 2600 is a set of data defining the order in which the questions are to be asked. For example, the sequence set 2600 may be {3, 1, 2}, meaning that the question that would ordinarily be asked third should be asked first, that the question that would ordinarily be asked first should be asked second, and that the question that would ordinarily be asked second should be asked third.

Continuing on with the example, execution of the hierarchy 2200 of FIG. 26 commences with a look-up operation, L1. During the look-up operation L1, the first element of the sequence set 2600 is used to index into an array containing the questions within the hierarchy. In the present example, since "3" is the first element of the sequence set, the third question from the array is retrieved. Next, the retrieved question (identified as Q1 in FIG. 26) is asked, and execution of the hierarchy proceeds as has been generally described with reference to FIG. 22. Thus, by inserting a look-up operation L1, L2, or L3 prior to each questioning operation Q1, Q2, or Q3, any desired sequence of questioning may be commanded.

The question hierarchies disclosed in FIGS. 22-26 may be programmed into the memory device 2108 of the patient monitoring device 2000, thereby obviating the need to transmit the text of the questions from the central computer 2100 to the patient monitoring device 2000. One skilled in the art understands that the question hierarchies 2200 may be implemented in the form of an application-specific integrated circuit, as well. Optionally, the questions within the hierarchies 2200 may written to be answered with either a "yes" or "no," achieving the advantage of simplifying the input required from the patient 2104, and thereby necessitating only "yes" or "no" buttons for the input device 2006. Further, any of the preceding question hierarchies 2200 forms may be combined.

As described earlier, the memory device 2108 may store each of the question hierarchies 2200 in a plurality of languages, so as to permit patients 2104 of many nationalities to use the device 2000. If the output device 2004 is an audio output unit, the questions within each of the question hierarchies 2200 may be stored in a digital audio format in the memory device 2108. Accordingly, the questions are presented to the patient 2104 as a spoken interrogatory, in the language of the patient's 2104 choice.

Figure 27:
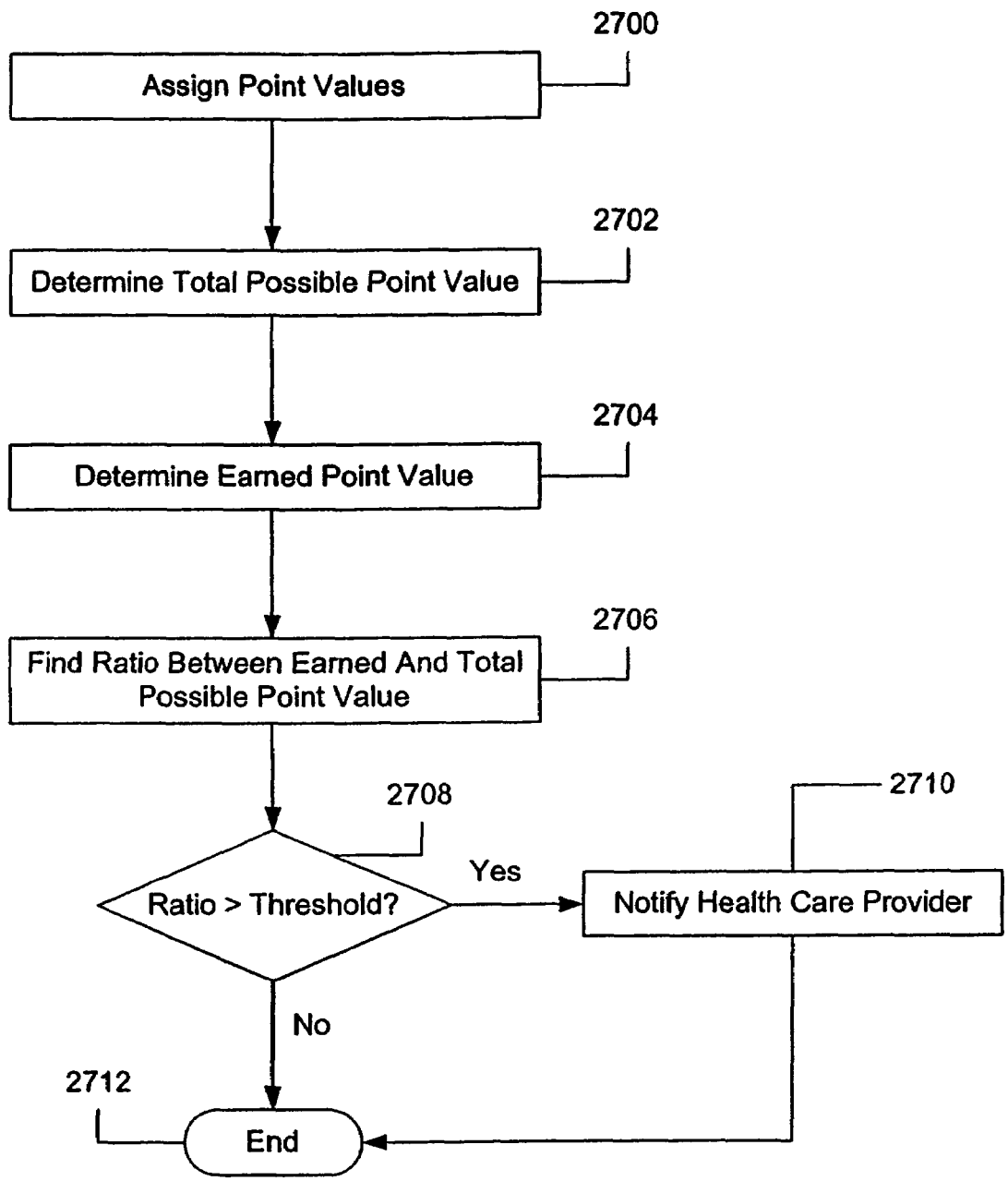
FIG. 27 depicts one method of determining whether a patient is in need of medical assistance, based upon the patient's response to questions presented from a question hierarchy.

FIG. 27 depicts a method by which the patient's 2104 answers to the questions presented in the hierarchies 2200 may be analyzed. As mentioned earlier, depending upon the outcome of the analysis, an exception report may be issued and a health care provider may be notified. According to the method depicted in FIG. 27, during operation 2700 a point value is assigned to each question in each of the invoked question hierarchies 2200. The points assigned to a given question are "earned" by a patient 2104, if the patient answers the question in a particular way. Otherwise, no points are earned. For example, an affirmative response to the question "are you experiencing shortness of breath?" may be worth 10 points, while a negative response to that question is worth nothing. A standard point value may be assigned to each question (each question has a point value of 10, for instance), or different questions may be assigned different point values (a first question is worth 10 points, while a question directed toward a more serious issue may be worth 30 points, for example). A default point assignment scheme may be presented for approval by a health care provider. The health care provider may then adjust the point assignment scheme to fit the needs of an individual patient 2104.

In operation 2702, the point value of each of the questions actually asked to the patient 2104 is determined. Thus, questions that were not asked to a patient 2104 are not included in this point total. In operation 2704, the patient's 2104 earned point value is totaled. Then, in operation 2706, the patient's 2104 earned point total (determined in operation 2704) is divided by the total possible point value (determined in operation 2702).

In operation 2708, it is determined whether the fraction found in operation 2706 exceeds a threshold (as with the point assignment scheme, the threshold may be defined by the health care provider). If so, the patient's health care provider is notified (perhaps by the issuance of an exception report), as shown in operation 2710. Finally, the process terminates in operation 2712.

Figure 28:
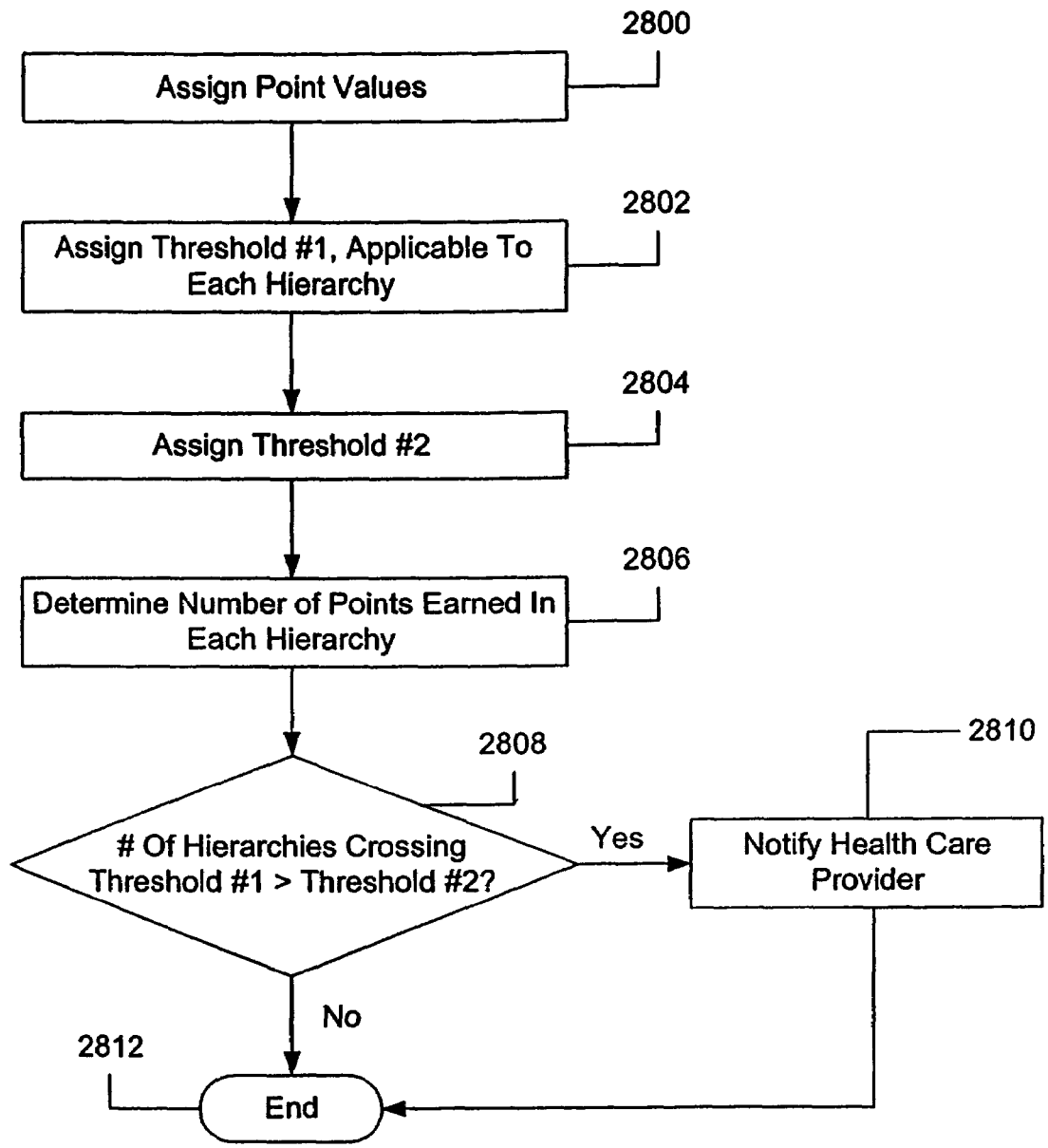
FIG. 28 depicts another method of determining whether a patient is in need of medical assistance, based upon the patient's response to questions presented from a question hierarchy.

FIG. 28 depicts another method by which the patient's 2104 answers to the questions presented in the hierarchies 2200 may be analyzed. According to the method depicted in FIG. 28, during operation 2800 a point value is assigned to each question in each of the invoked question hierarchies 2200. The details of the point assignment scheme are identical to those in operation 2700 of FIG. 27.

Next, in operation 2802, a threshold is assigned to each invoked hierarchy 2200. Again, this threshold may be assigned by default, and the health care provider may be given an option to adjust this threshold. The threshold of operation 2802 applies to each hierarchy 2200, meaning that a decision will be made, on a hierarchy-by-hierarchy basis, whether the patient 2104 has accumulated sufficient points in a particular hierarchy to cross a threshold assigned to that hierarchy 2200. In operation 2804, a second threshold is assigned. The threshold of operation 2804 relates to the number of hierarchies 2200 that may be allowed to exceed the threshold of operation 2802.

In operation 2806, the number of points earned by the patient 2104 in each hierarchy 2200 is determined. Then in operation 2808, it is determined whether the number of hierarchies 2200 in which the threshold of operation 2802 was crossed exceeds the threshold of operation 2804. If so, the patient's health care provider is notified, as shown in operation 2810. Finally, the process terminates in operation 2812.

The methods of FIGS. 27 and 28 are preferably performed by the remote computer 2100, although they may be performed by any other processing device. The aforementioned methods are preferably embodied as software stored in a memory device within the central computer 2100. However, they may be embodied on a computer-readable medium, such as a compact disc, a floppy disc, a network cable, or any other form of media readable by a computer.

Weight Loss/Weight Management System

Figure 29:
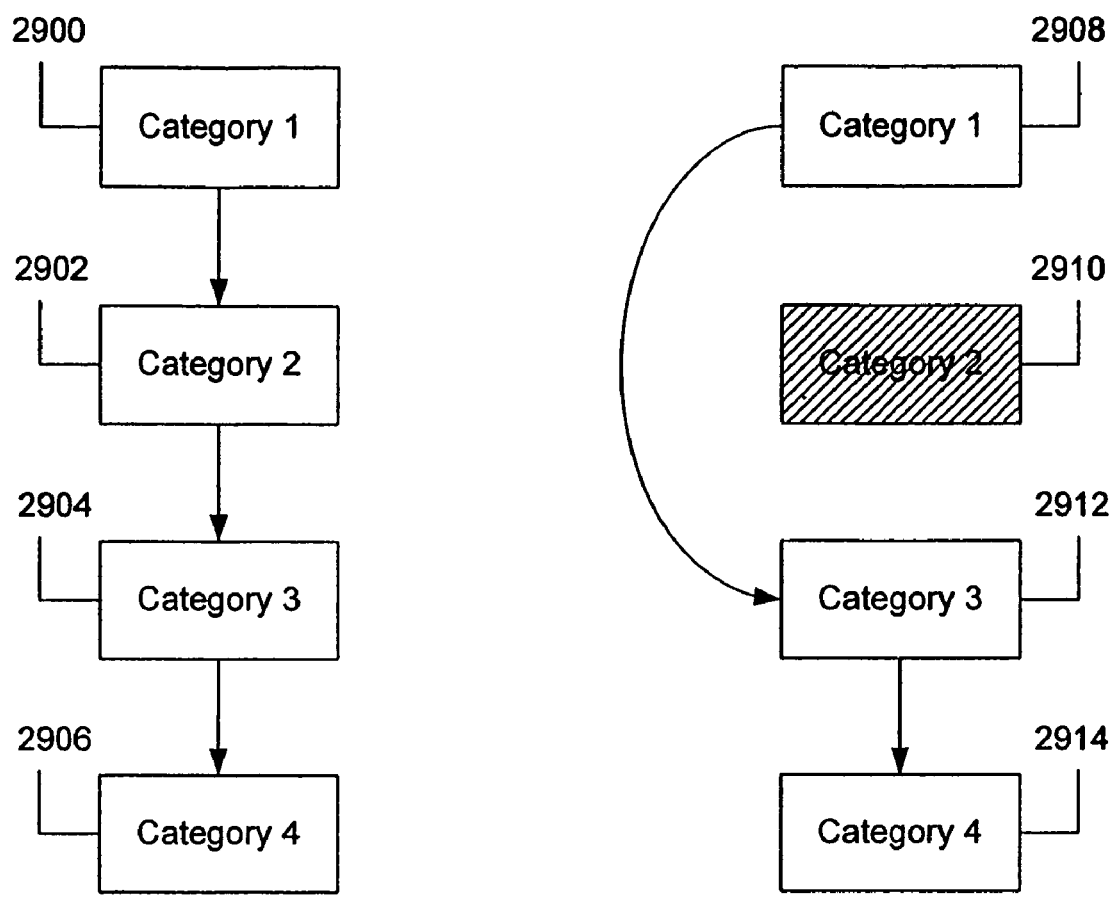
FIG. 29 depicts a questioning scheme according to one embodiment of the present invention.

FIG. 29 depicts a questioning scheme that may be employed by any of the embodiments of the system depicted or referred to in any of the twenty-eight preceding figures. As can be seen from FIG. 29 there is shown a first sequence of questions which have been organized into categories 2900, 2902, 2904, and 2906 and a second sequence of questions which have been organized into categories 2908, 2910, 2912, and 2914. Typically, all of the questions within a category such as category 2900 relate to a given topic. In the case of a system for weight loss or weight management, for example, the category may relate to overeating, and each of the questions may related to different facets of overeating.

As shown in FIG. 29, the typical flow for such a scheme is for the questions within a first category, such as category 1 2900, to be asked followed by the questions within a second category, such as category 2 2902, to be asked. Following this, the questions in category 3 2904 are asked, and finally the questions in category 4 2906 are asked. Of course, in principle, a questioning scheme may have questions organized into any number of categories not simply four as is shown in FIG. 29. Further, it is not necessary that the categories be preceded through in sequential fashion, although this is has been shown in FIG. 29.

As shown by the question sequence composed of categories 2908, 2910, 2912, and 2914, a given category of questions may be deactivated. In this example category 2 2910 is deactivated, as is indicated by the cross hatching. In such an instance, the questions within category 1 2908 are asked, category 2 is skipped because it is deactivated, and the execution flow proceeds to category 3 2912 and category 4 2914. As is discussed later, it is possible for any number of categories to be activated or deactivated and it is also possible to activate or deactivate categories based on a predetermined schedule such as activating or deactivating categories based on the day of the week. For example, category 2 2910 may be activated on Mondays, Wednesdays and Fridays and deactivated on Tuesdays, Thursdays, Saturdays and Sundays. Similarly, example category 4 2914 may be activated on Mondays, Tuesdays and Wednesdays, but deactivated on Wednesdays, Thursdays, Fridays, Saturdays, and Sundays. Categories may be activated and deactivated based on date ranges, as well.

Figure 30:
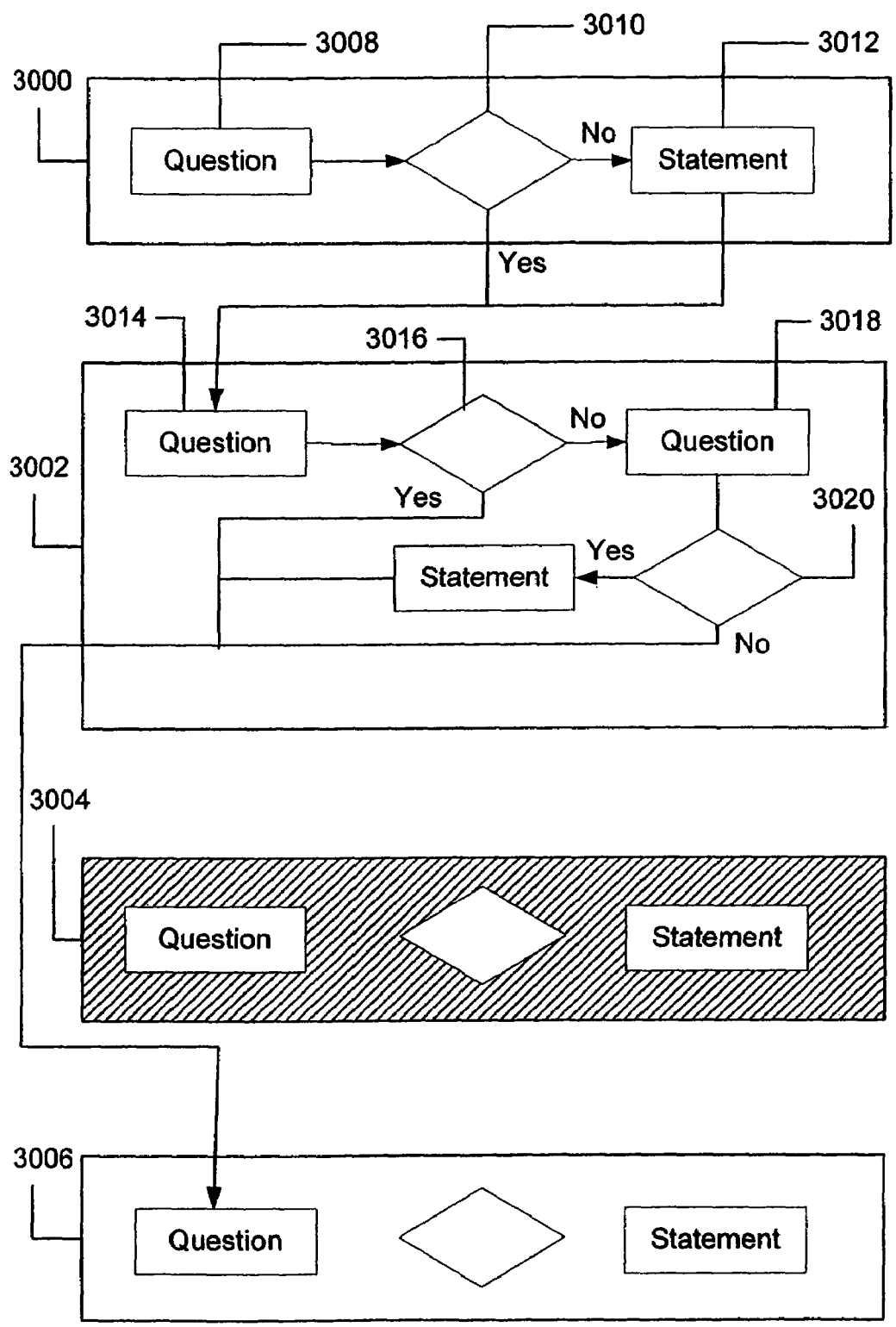
FIG. 30 depicts an exemplary question sequence composed of four categories, according to one embodiment of the present invention.

FIG. 30 depicts a question sequence composed of four categories 3000, 3002, 3004, and 3006. As was the case in FIG. 29, the flow from category to category is largely sequential, in that the flow moves from category 3000 to category 3002, skips over category 3004 because it is cross hatched and depicted as deactivated for the sake of example, and proceeding on to category 3006.

Intracategory execution flow is shown for the sake of example. Turning to question category 3000, it can be seen that therein is included a question 3008 followed by a branch instruction 3010. If, for example, category 3000 were related to the topic of overeating, question 3008 may read "did you eat more than three meals today?" At branch instruction 3010 the answer of the person using the monitoring unit is evaluated, and the flow of execution is directed based on the person's answer. For example if the person answered "no," i.e., he did not eat more than three meals that day, the flow may go on to statement instruction 3012, which may be a praise statement. For example praise statement 3012 may read "good job." Execution flow would then move on to category 3002. On the other hand, if the person answered that he had eaten more than three meals, execution flow would have moved from branch instruction 3010 directly to category 3002.

Category 3002 shows an intracategory execution flow that is a little more complicated than the one shown with reference to category 3000. Assuming for the sake of example that question category 3002 was directed toward the topic of emotional eating, then question 3014 may read "were you happy today?" The flow then moves on to branch instruction 3016. If the person had answers "yes," flow proceeds on to the next active question category, question category 3006 (because question category 3004 is depicted as being deactivated). On the other hand, if the person answers "no" to the question "where you happy today," then flow proceeds from branch instruction 3016 to follow-up question 3018, which may read "did you eat to feel better?" The person's answer is evaluated at branch instruction 3020. Assuming the person answered that he did not eat to feel better, once again flow would move on to question category 3006. On the other hand, if the person answered that he had eaten to feel better, then execution flow moves on to reminder statement 3022 which may read "Remember to stick to your meal plan." Thereafter execution flow would move on to category 3006.

Thus, as can be seen from the preceding example, question categories 3000, 3002, 3004, and 3006 may include: (1) questions related to a topic; (2) branch instructions that control the flow of execution based upon the person's answer to the questions; (3) follow-up questions; and (4) praise or reminder statements based upon the person's answers to the questions. Generally, the flow from category to category is sequential, although this is not necessary. Generally, execution flow skips over deactivated question categories and proceeds on to the next active question category.

Figure 31:
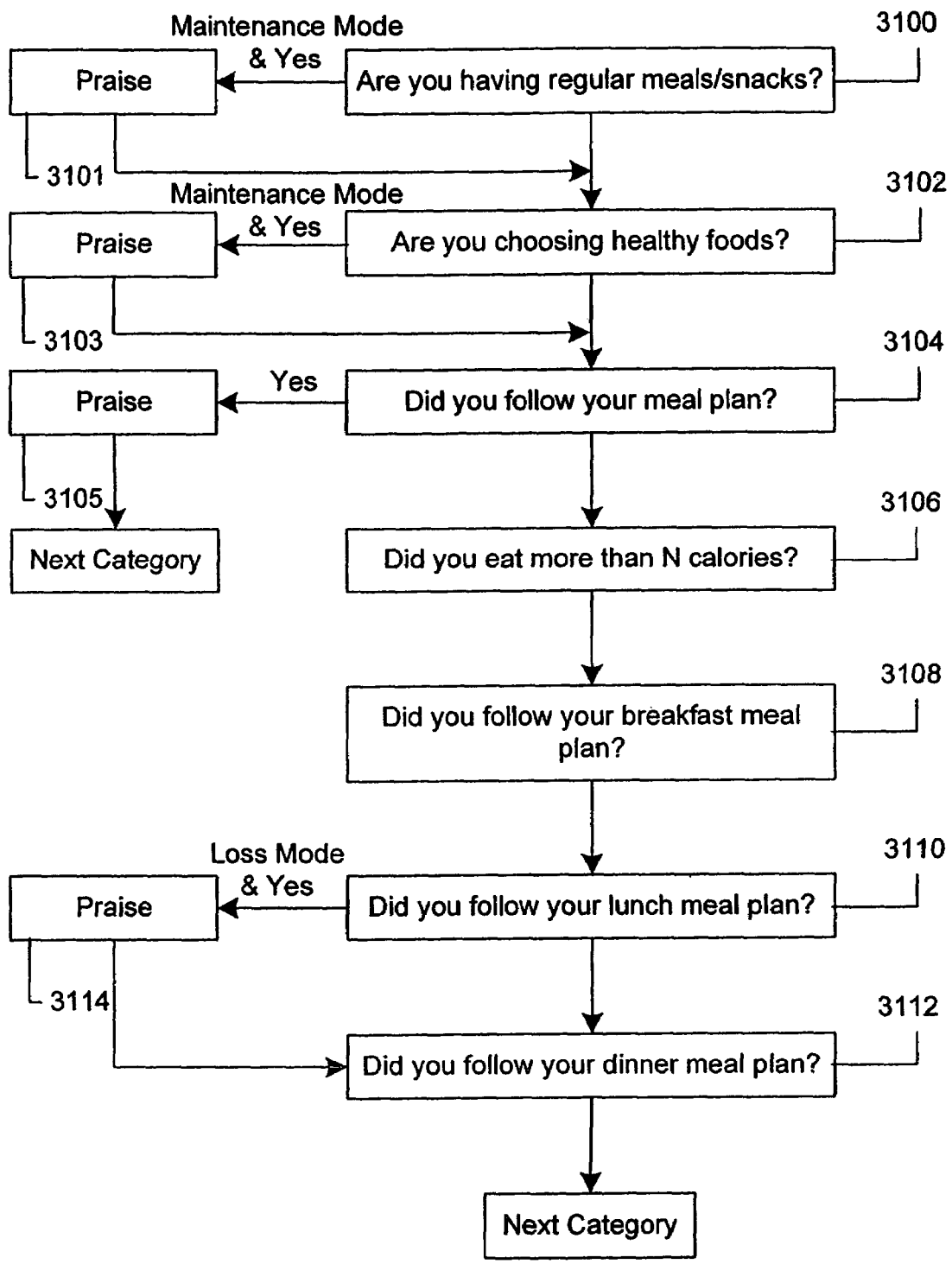
FIG. 31 depicts a questioning scheme influenced by a mode of operation, according to one embodiment of the present invention.

FIG. 31 depicts a question set having questions 3100, 3102, 3104, 3106, 3108, 3110, and 3112. The question set in FIG. 31 is directed toward the topic of meal planning. Thus each question within this category relates to determining whether the person using the monitoring unit exhibited deliberate dietary habits throughout the day.

FIG. 31 also depicts the principle that the monitoring unit, such as monitoring unit 14, may be put into a mode of operation. In the case wherein monitoring unit 14 is programmed for the purpose of encouraging weight loss or weight management, the monitoring unit may be programmed in either a weight loss mode or a weight management mode. Execution flow within a question category may be altered depending upon the mode that the monitoring unit is in. This principle is illustrated in FIG. 31.

Execution flow begins with question 3100: "Are you having regular meals/snacks?" If the person answers "yes," and if the monitoring unit is in weight management mode, execution flows to praise statement 3101, which may read, "You are focused on your goals!" Thereafter, execution flow proceeds to question 3102. On the other hand, if the monitoring unit is in weight loss mode, execution flow moves on to question 3102, regardless of the person's answer. Question 3102 reads, "Are you choosing healthy foods?" Once again, if the person answers "yes," and if the monitoring unit is in weight management mode, execution flow moves on to praise statement 3103, which may read "Great job with this system! Keep it up! " As before, if the monitoring unit is in weight loss mode, execution flow moves on to question 3104, irrespective of the person's answer. Question 3104 reads "did you follow your meal plan?" If the person answers "yes," execution flow moves on to praise statement 3105. Praise statement 3105 may be different based upon whether the monitoring unit is in weight loss mode or weight management mode. For example, if the monitoring unit is in weight loss mode, praise statement 3105 may read, "You're on your way to success." If on the other hand the monitoring unit is in weight management mode, praise statement 3105 may read, "Good job!" Thereafter as can be seen from FIG. 31 the remaining questions in this question category are skipped and the next activated category is executed. On the other hand if the person were to answer "no" to question 3104, execution flow moves on to question 3106, which reads "Did you eat more than N calories". "N" is a variable which may be set by the remote computer, such as the remote computer 32 depicted in FIG. 4, and may be individualized for a particular user. Thereafter, execution flow moves on to question 3108, which reads "Did you follow your breakfast meal plan?" Irrespective of the person's answer, execution flow moves on to question 3110, which reads "Did you follow your lunch meal plan". If the person answers "yes," and the monitoring unit is in weight loss mode, execution flow moves onto praise statement 3114, which may read "Great job with this system! Keep it up!" Thereafter, execution flow moves on to question 3112. On the other hand, if the monitoring unit is in weight management mode execution flow moves from question 3110 to question 3112 irrespective of the person's answer. The final question in the exemplary question category reads "did you follow your meal plan?" Upon answering this question execution flow moves on to the next active category.

Although FIG. 31 shows specific questions that may be included within a question category directed to meal planning, other question categories may exist in a system for weight loss or weight management. Those categories may include categories directed toward dietary recording, overeating, skipping of meals, eating at home, portion size, eating out, grocery shopping behavior, label reading, water consumption, happiness, stress, depression, support, body image, fit of clothing, body measurements, program satisfaction, exercise and lesson plans.

In sum, FIG. 31 depicts the following general principles. The monitoring unit may be programmed to be in one of a plurality of modes of operation. Based on the mode of operation, the monitoring unit may alter intracategory and/or intercategory execution flow. For example, the monitoring unit may ask a different follow-up question, may give a different praise or reminder statement, may execute a different category, may omit a follow-up question, and/or may omit a praise or reminder statement, based upon the selected mode of operation. Although not depicted by FIG. 31, each of the questions (such as 3100-3112) within a category are individually activatable and deactivatable. Individual questions may be activated or deactivated according to a schedule, or may be activated or deactivated indefinitely. For example, any question within a group may be deactivated for a given use, although the group as a whole may be active. Thus, for example, the question "Are you choosing healthy foods?" (question 3102) may be activated on Mondays, Wednesdays and Fridays, but deactivated on Tuesdays, Thursdays, Saturdays and Sundays. Conversely, a question may be activated, although the group in which the question resides is deactivated. Such programmability permits a manageable number of questions to be presented to the person using the monitoring unit. Further, such programmability allows the person's experience to vary from day to day, so that the person maintains his or her interest in the unit.

The questioning schemes depicted in FIGS. 29-31 may be embodied according to the question hierarchy technology described with reference to FIGS. 20-28 herein. Such an embodiment is within the scope of the invention and disclosure herein.

Figure 32:
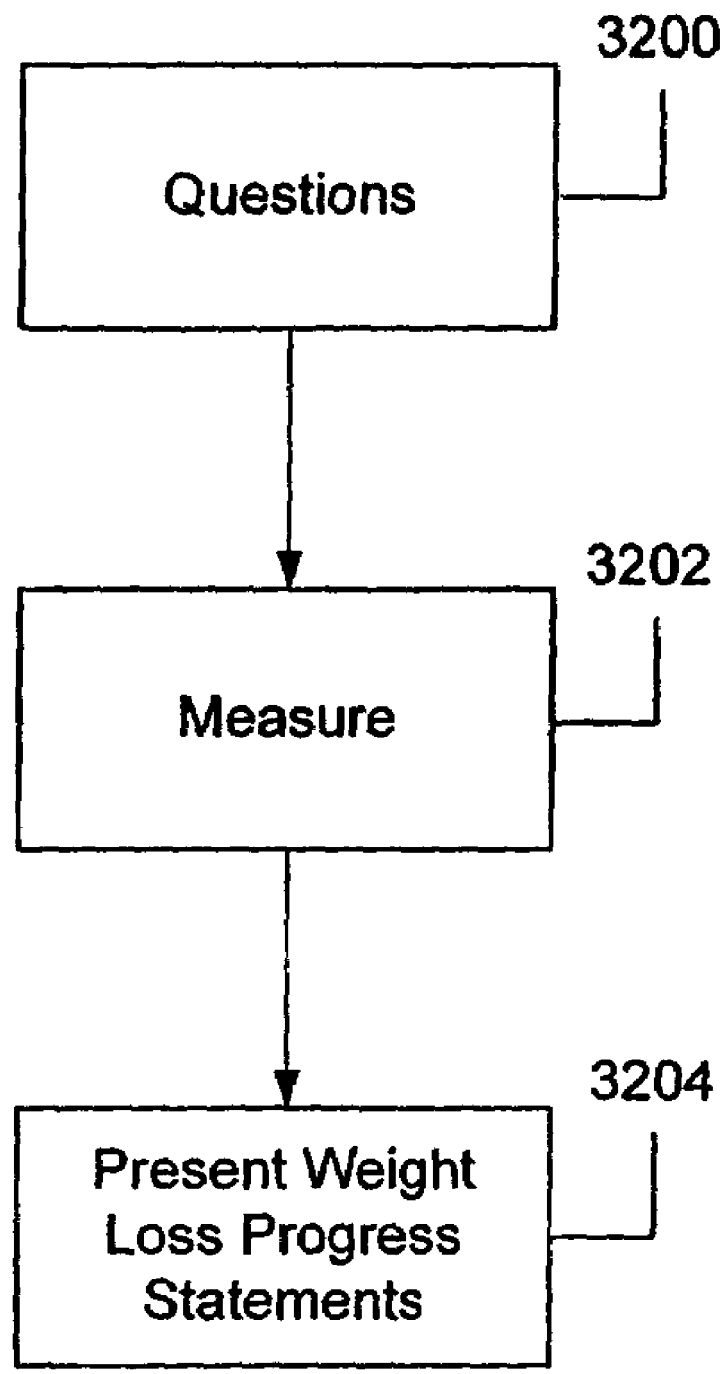
FIG. 32 depicts an example of execution flow for a monitoring unit designed for encouraging weight loss or weight management, according to one embodiment of the present invention.

FIG. 32 depicts an example of execution flow for a monitoring unit designed for encouraging weight loss or weight management. As can be seen from FIG. 32, the monitoring unit may initially ask the person questions related to weight loss or weight management according to a questioning scheme as described with reference to FIGS. 29 through 31. Further, the monitoring unit may measure the weight of the person as shown in operation 3202. After execution of operation 3202, the monitoring unit may transmit the person's answers to the questions and the person's weight to a remote computing system so that the information can be processed and stored and so that the remote computing system can determine if a health care provider should be alerted. Details related to generation of alerts for health care providers are discussed below. Finally, as shown in operation 3204, the monitoring unit may present weight loss progress statements to the person. The weight loss progress statements may take on several forms, each of which may be activated or deactivated during designated time intervals, as is discussed below. For example, one form of progress statement may be activated during Mondays, Tuesdays, and Wednesdays, while another form is activated on Thursdays, Fridays, Saturdays, and Sundays.

Examples of weight loss progress statements include a presentation of the person's present weight followed by the presentation of the person's weight at some point in the past such as a week ago, a month ago, three months ago, six months ago, nine months ago, a year ago or even two years ago. Alternatively, a weight loss progress statement may include a presentation of the person's present weight followed by the person's average weight (or some other measure of central tendency) over a particular time interval such as that person's average weight one week ago, one month ago, three months ago, six months ago, nine months ago, a year ago, or even two years ago. As another alternative, the person may be presented with their weight when they began using the monitoring unit and may also be presented with his or her present weight. Yet another alternative is a presentation of the person's present weight and a presentation of the person's milestone weight. A milestone weight is a weight that is intermediate the person's weight when he or she began using the monitoring unit and a final goal weight that the person wants to achieve. Still further, a weight loss progress statement may include a statement of the percentage of the total weight loss goal the person has met, or a statement of the person's total weight loss goal. If the monitoring unit is in weight maintenance mode as opposed to weight loss mode, the progress statement may include a statement of what the maintenance weight is for the particular person. The maintenance weight may actually be a range. For example a person having a weight goal of 165 pounds may have a maintenance weight range between 160 and 170 pounds.

Although the discussion related to the progress statements generated in operation 3204 of FIG. 32 has been in the context of discussing weight loss, progress statements may be produced for any other measurable parameter. For example, a progress statement may be generated to show the variation, over an interval of time, in activity level or number of steps a person has taken. Other examples of parameters that may be the subject of progress statements include caloric intake, fat intake, water consumption, intake of dietary fiber, vitamin intake, or intake of any other nutritional item.

Figure 33:
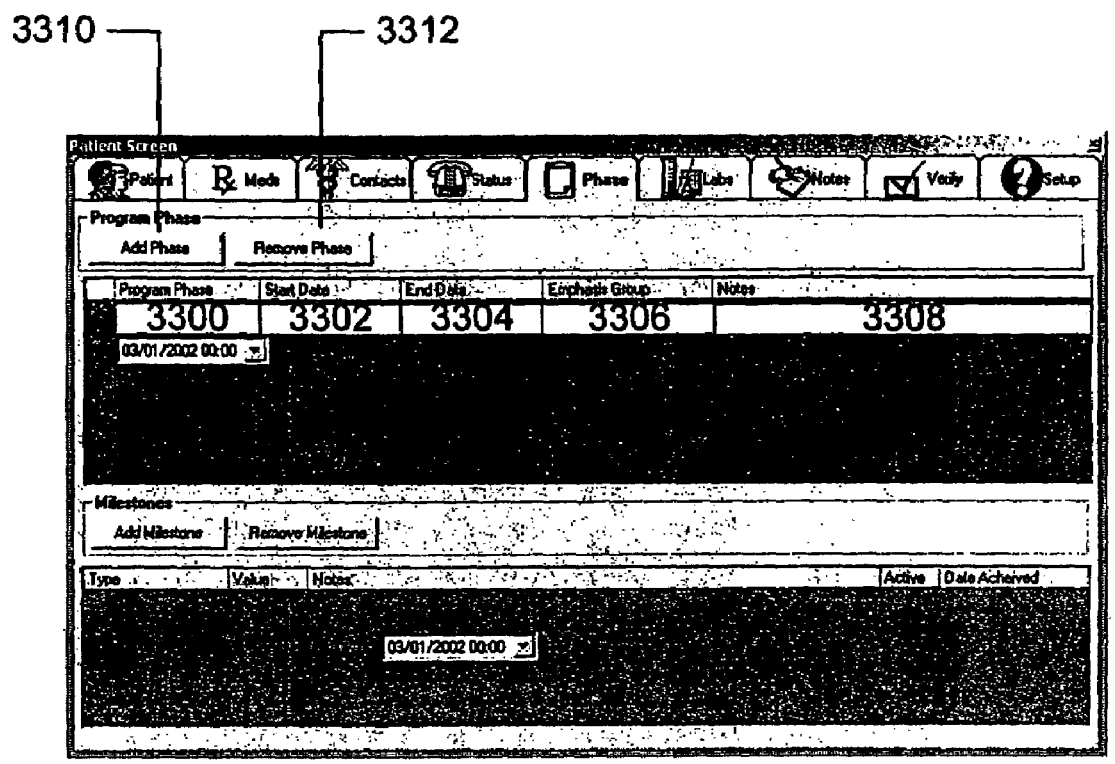
FIG. 33 depicts a program phase screen that permits a user of the remote computing system to divide the person's weight loss or weight management program into phases, according to one embodiment of the present invention.

FIG. 33 depicts a program phase screen that permits a user of the remote computing system, such as remote computing system 32 shown in FIG. 4, to divide the person's weight loss or weight management program into phases. A phase is an interval of time during which certain question categories are asked while other question categories are not asked. A phase may be added by selecting the "add phase" button 3310. This selection allows the user to select a phase name entered in field 3300, a start date for the phase entered in field 3302, and end date for the phase entered in field 3304, and an emphasis group entered in field 3306. The emphasis group identifies the question categories that are to be executed by the monitoring unit between the start date 3302 and end date 3304. For example, if the user of the remote computing system wished the person using the monitoring unit to have questions related to meal planning and overeating presented to them during a first phase, the emphasis group 3306 would include meal plan and overeating categories but may exclude other categories not appropriate for this phase. Notes associated with each phase may be stored in the note field 3308. To remove a phase, highlight the particular phase and select the "remove phase" button 3312. In principle a weight loss or weight management program may be divided into any number of phases, not simply a weight loss and weight management phase.

Phases permit a user of the remote computing system to customize questioning appropriate to a particular person's needs. One additional benefit of phases is that it prevents the person using the monitoring unit from always being presented with the same set of questions.

Figure 34:
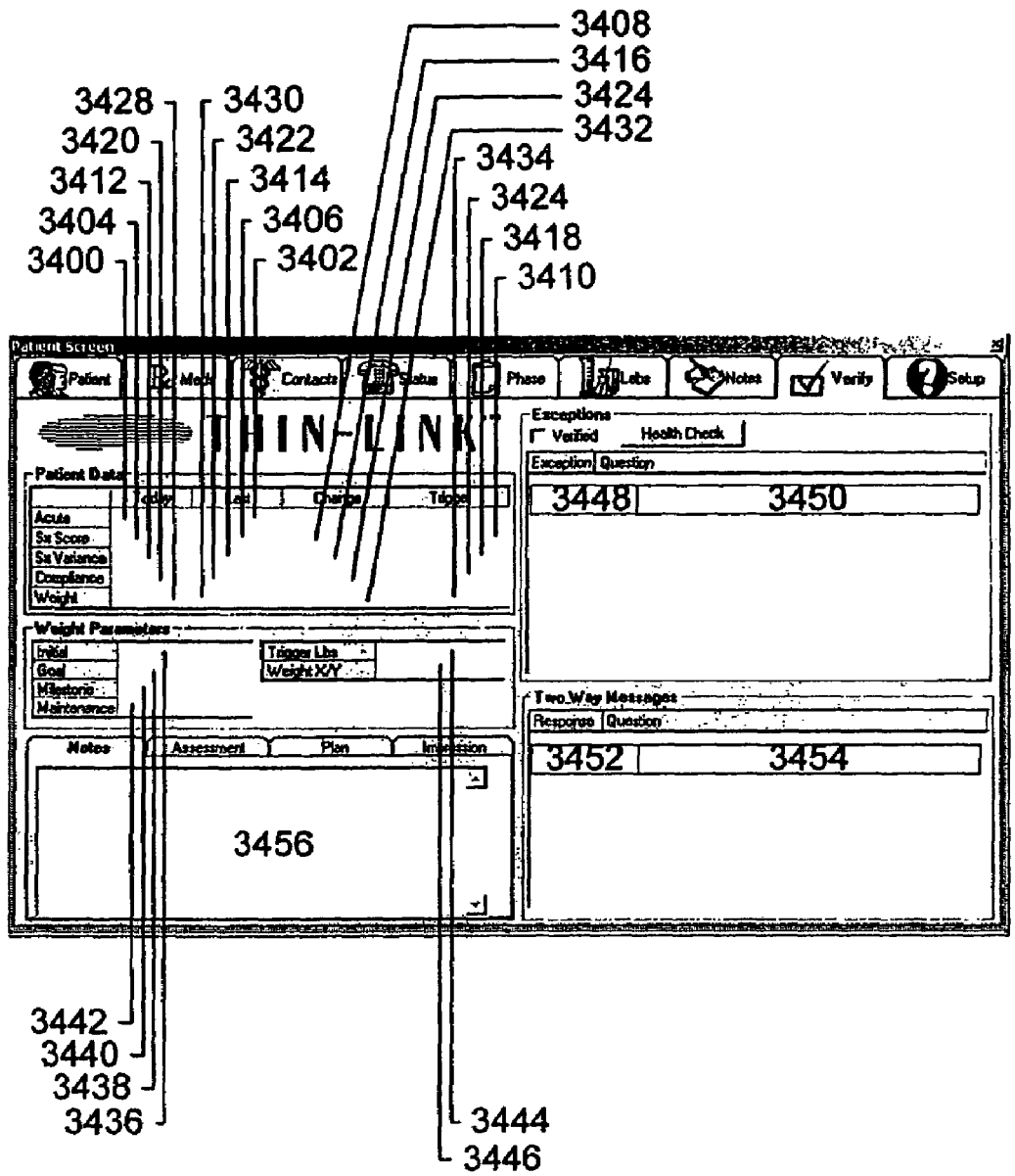
FIG. 34 depicts a verification screen that may be executed by the remote computing system according to one embodiment of the present invention.

FIG. 34 depicts a verification screen in which patient data is displayed in the upper left-hand corner. As can be seen from FIG. 34, the patient data portion of the screen is a grid having rows labeled Acute, Sx Score, Sx Variance, Compliance and Weight and columns labeled Today, Last, Change and Trigger. The first four row labels relate to different types of questions. The monitoring unit may be programmed to ask three different kinds of questions: (1) acute questions; (2) compliance questions; and (3) scored questions. Acute questions are questions that attempt to determine whether the person needs immediate attention. For example, the person's answers to acute questions may indicate that the person needs contact with an operator, case manager, health care professional, dietician, counselor or any individual responsible for monitoring the person's information or overseeing the person's weight loss or weight management. Compliance questions determine whether the person needs follow-up because that person is simply not complying with the plan, and scored questions may be used to determine whether the person needs follow-up because the person's answers, in general, indicate that the plan is not working for one reason or another. The term "Sx" (which typically is known to be an abbreviation for "symptom") is used to refer to scored questions. As the term is used herein, the term "symptom" or "Sx" refers not just to physical symptoms, but to lifestyle modifications (e.g., cooking at home more often), behavior modifications (e.g., reading food labels), psychological outlook (e.g., having a happy or depressed state of mind), actions undertaken by the person using the monitoring unit, or other information relating to success or failure of weight loss or weight management for the person using the monitoring unit. Thus, questions relating to "symptoms" may inquire into any sort of information relating to success or failure of weight loss or weight management for the person using the monitoring unit.

Turning first to the row labeled "acute," there are two fields, fields 3400 and 3402, which may contain data. Field 3400 contains an indication of whether the person is considered acute on the present day, and field 3402 contains an indication of whether the person was considered acute the last time the person used the monitoring unit. If a person is determined to be acute, an alert may be sent to a health care professional so that the health care professional can contact the person. The determination of whether a person is acute may be made on the basis of a person's answer to a single question. For example, if a person were to answer "no" to the question "Do you feel life is worth living," this single answer would cause the system to determine that the person was acute. On the other hand, the system may determine that a particular person is acute on the basis of answers to several questions. For example consider the following three questions: (1) Were you stressed today?; (2) Are you finding ways to manage your stress?; and (3) Were you angry today? An affirmative response to all three questions may be sufficient to trigger the decision that the patient is acute.

Moving on to the next row, which is labeled "Sx Score," it can be seen that this row contains four fields, fields 3404, 3406, 3408 and 3410. This row and the following row, labeled "Sx Variance," relate to scored questions. Scored questions are general questions that have a point value or score associated with them. "Points" are accumulated based upon the person's answers to the scored questions. A total score may tallied for each use of the monitoring unit. Field 3404 shows the person's present total score, while field 3406 shows the total score earned by the person the last time the person used the monitoring unit. Field 3408 shows the difference between the person's present score and the score the last time he or she used the unit. Field 3410 shows a triggering condition, which indicates whether an alert will be generated based upon the person's answers to the scored questions. The trigger condition may be a simple threshold to which the person's score is compared or can be a threshold based upon a percent score.

For example, the threshold may be a score of twenty, with any score exceeding the threshold causing the remote computing system to generate an alert. Alternatively the trigger 3410 may express a trigger condition that is activated when a person's score changes by more than a given number of points in a given number of days. For example, an alert may be generated if the person's score changes by more than ten points in three days.

As stated above, the trigger condition may be expressed as a percentage value. Per such a scenario, the scoring scheme may be implemented as follows. A score is assigned to each answer provided by the person using the monitoring unit. A total score is arrived at by summing each of the scores earned by the person's various answers. The total score is divided by the total possible score the person could have earned. The total possible score, which serves as the divisor, is arrived at by summing the highest scores available for each question actually posed to the person using the monitoring unit. Questions not actually posed to the person using the monitoring system do not figure into the calculation of the total possible score. The quotient arrived at per the preceding procedure is compared to a percentage threshold. If the quotient exceeds the threshold, an alert is generated.

The third row, labeled "Sx Variance" relates to the variance in scores earned by the person using the monitoring unit. For example, field 3412 presents the variance in score earned by the person using the monitoring unit, and field 3414 presents the variance in scores earned by the person the last time the person used the monitoring unit. Field 3416 shows the difference between field 3412 and 3414. Field 3418 relates to a trigger condition which if satisfied, may cause the remote computing system to generate an alert. For example, an alert may be generated if a person exhibits a change in variance that exceeds a given percentage over a given number of days.

The fourth row is labeled "Compliance" and has four fields, fields 3420, 3422, 3424, and 3426. This row relates to the way the person using the monitoring unit answers the compliance questions. One point may be earned for each answer indicating that a person is not complying with the plan. Field 3420 shows the number of compliance points earned, and field 3422 shows the number of compliance points earned the last time the person used the monitoring unit. Field 3424 shows the difference between fields 3420 and 3422. Field 3426 presents a trigger condition which if satisfied may cause the remote computing system to generate an alert. For example, an alert may be generated if a person earns more than a given number of compliance points in a given number of days.

The fifth and final row is labeled Weight and contains four fields, field 3428, 3430, 3432 and 3434. Field 3428 shows the person's current weight, and field 3430 shows the person's weight the last time the he or she used the monitoring unit. Field 3432 shows the difference between field 3428 and 3430. Field 3434 indicates a trigger condition which if satisfied may cause the remote computing system to generate an alert. The alert condition expressed in field 3434 may be a simple threshold. For example, if the person's weight exceeds a threshold of 180 pounds, a health care professional may be alerted. Alternatively, the trigger condition expressed in field 3434 may relate to a change in the person's weight. For example, if the person's weight changes by more than a given number of pounds in a given number of days, an alert may be generated.

The screen depicted in FIG. 34 also contains a weight parameter section, which contains fields 3436 through 3446. The data presented in this portion of the screen allows the user of the remote computing system to obtain a quick overview of the weight condition of the person using the monitoring unit. Field 3436 presents the weight of the person using the monitoring unit at the point in time in which he began using the monitoring unit. Field 3438 presents a person's goal weight, which is a weight at which the person using the monitoring unit ultimately wants to reach. Field 3440 presents the person's milestone weight, which is a weight somewhere between the person's starting weight 3436 and goal weight 3438. The person's maintenance weight range is indicated in field 3442. This weight range is the range the person should stay in after reaching his or her goal weight. Field 3444 shows a threshold weight which if exceeded may cause the remote computing system to generate an alert and field 3446 indicates a trigger condition caused by weight change which if satisfied may cause the remote computing system to generate an alert. For example, if field 3446 contains the data "5/10," this would mean that an alert may be generated if the person exhibited a weight change of more than 5 pounds in 10 days.

The screen depicted in FIG. 34 also contains an exception portion, which contains fields 3448 and 3450. The data in fields 3448 and 3450 is intended to provide an indication to the user of the remote computing system of which questions caused an alert to be generated. In field 3448, data is contained which indicates whether the alert was generated due to answers to acute questions, scored questions or compliance questions. Field 3450 contains the particular question that caused an alert to be generated. For example, a person using the monitoring unit may be indicated as being acute because of affirmative answers to the questions: (1) Were you stressed today?; (2) Are you finding ways to manage stress?; (3) Were you angry today? Per such a scenario, three entries are found in the exceptions portion. The exceptions type field 3448 reads "Acute" for all three entries. The first entry reads "Were you stressed today". This second entry reads "Are you finding ways to manage stress," and the third entry would read "Were you angry today." Thus, for each question that contributed to an alert being generated, there exists an entry in the exception portion of the screen depicted in FIG. 34. The text of the question is presented in field 3450 and the type of the question is presented in field 3448.

The screen depicted in FIG. 34 also contains a portion relating to two-way messages. This portion of the screen contains two fields, fields 3452 and 3454. Field 3454 presents the text of a two-way message and field 3452 presents the person's corresponding answer. Two-way messaging is discussed in detail herein in the portions of the specification related to FIGS. 11 through 18.

Patient notes may be entered in field 3456, which is located in a note portion of the screen.

Figure 35:
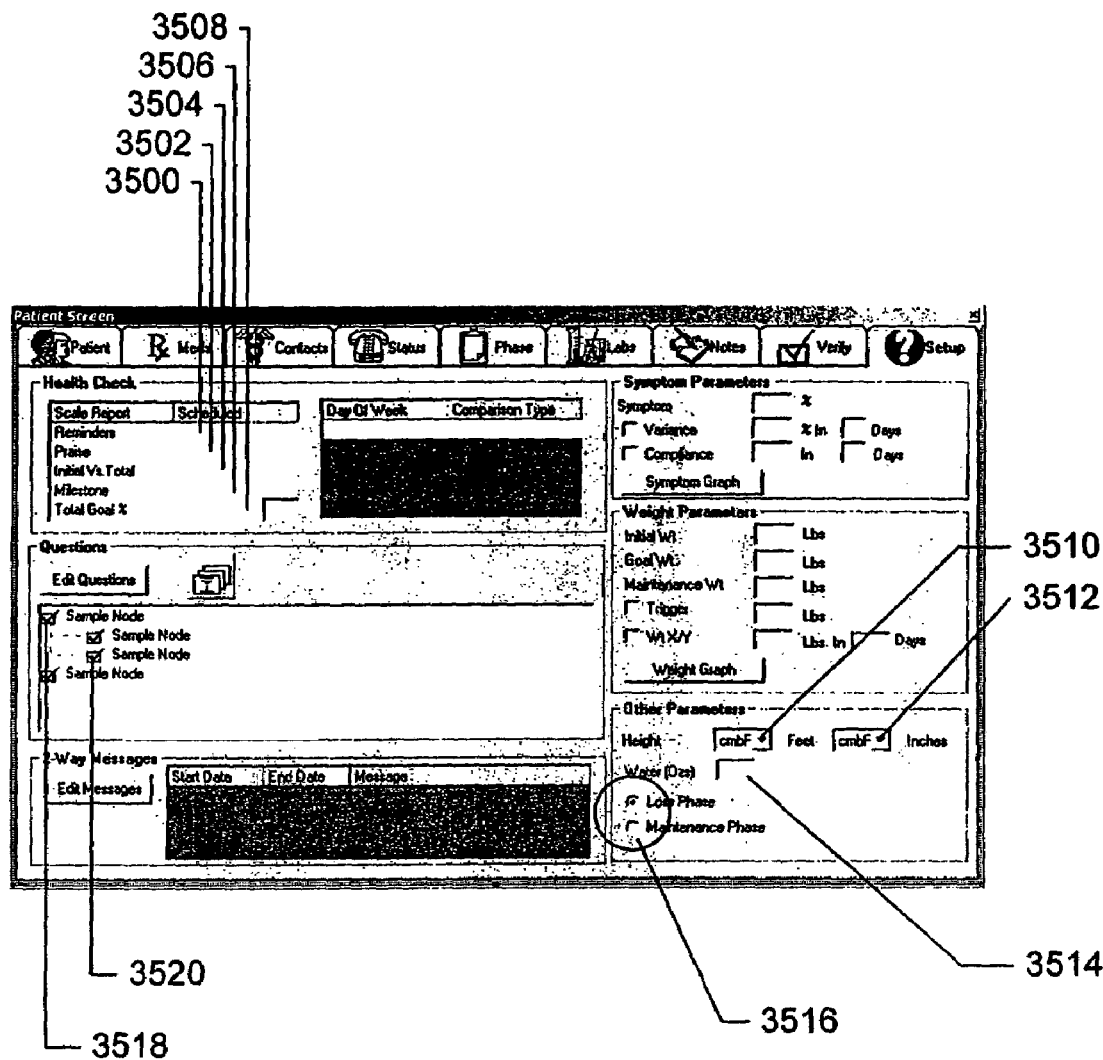
FIG. 35 depicts a set-up screen that may be executed by the remote computing system according to one embodiment of the present invention.

A set-up screen is depicted in FIG. 35. The set-up screen contains a health check portion of the screen, which contains fields 3500-3508. In field 3500, the user of the remote computing system can schedule the days of the weeks on which reminders are to be turned on. An example of a reminder was presented in FIG. 30 and labeled by reference numeral 3022. ("Remember to stick to your meal plan.") These forms of reminders may be turned off. If reminders are deactivated, a reminder statement is not presented, even if execution flow would ordinarily indicate that a reminder is to be given. Thus, for example, reminders may be scheduled for Monday, Wednesday, and Friday. On these days reminders will be presented to the patient. On Tuesdays, Thursdays, Saturdays and Sundays no reminders will be given to the patient. Similarly, praise statements (field 3502) may be scheduled for certain days of the week. Fields 3504, 3506, and 3508 permit weight loss progress statements to be scheduled for certain days of the week.

The screen depicted in FIG. 35 also contains a symptom parameter section in which the trigger condition depicted in fields 3410 and 3418 on FIG. 34 may be set.

The screen depicted in FIG. 35 also contains a weight parameter section in which the information shown in fields 3436, 3438, and 3442-3446 in FIG. 34 may be set.

The screen depicted in FIG. 35 also contains an "Other Parameters" portion. In field 3510 and 3512, the height in feet and inches of the person using the monitoring unit may be entered. In field 3514 the number of ounces of water the person using the monitoring unit is to consume may be entered, and via the selection buttons identified by reference numeral 3516, the phase in which the monitoring unit is programmed to be may be selected. For example, the monitoring unit may be selected for weight loss phase or weight maintenance phase. Other parameters may be set from this screen, as well. In principle, this portion of the screen may contain fields that allow entry of ideal values for any parameter characterizing the person using the monitoring unit. For example, this portion of the screen may contain fields that allow entry of ideal values distance the person is to walk, number of steps the person is to take in a day, number of calories the person is to consume in a day, and so on. The values entered in these fields may be used in the process of generating an alert (described above) or in progress reports. For example, an alert may be generated if the activity level of the person falls short of a threshold. Additionally, an alert may be generated if, over a span of time, the person's number of calories burned, number of steps taken over, or distance walked falls short of a threshold. Still further, an alert may be generated if the number of calories consumed by the person using the monitoring device exceeds a threshold. The values compared against these thresholds may be input manually (e.g., may be estimated) by the person using the monitoring device, or may be directly measured by a measuring device that communicates such data to the monitoring device. The thresholds may be equal to the ideal values entered into the fields in this portion of the screen, or may be calculated therefrom, such as by multiplying the values in these fields by a factor (e.g., multiplying ideal caloric intake by 1.1 or 1.2).

The screen depicted in FIG. 35 also contains a "Questions" section. This section relates to the question hierarchy technology discussed with reference to FIGS. 20-28. For example the check box 3518 pertains to a first question hierarchy, which is depicted as consisting of two questions. The check box 3518 allows the entire hierarchy to be activated or deactivated. Check box 3520 permits a particular question, which is within the hierarchy controlled by check box 3518, to be activated or deactivated.

A monitoring unit may be programmed to utilize a personal identifier code. In such an embodiment the monitoring unit is rendered usable by more than one person. For example, a user of the monitoring unit commences his use of the monitoring unit by entering a personal identifier code. The monitoring unit uses the personal identifier code to determine the identity of the user. The monitoring unit proceeds to execute on the basis of data (such as data presented on the screens depicted in FIGS. 33-35) that is associated with the personal identifier code. Thus, for example, the monitoring unit asks questions appropriate for the particular user and responds with praise and reminder statements appropriate for the particular user. The particular user's answers and measured weight are transmitted to a remote computing system in association with the personal identifier code. This permits the remote computing system to know whose data it has just received.

Such an embodiment may be useful in a setting in which multiple members of a family all desire to use the same monitoring unit. Alternatively, such an embodiment with the system may be useful in a health club setting in which one or a small number of monitoring units are used for a large populace of users. The personal identifier code may be a name and/or a password that are entered into the input device of the monitoring unit (e.g., the personal identifier may be entered via a keypad into the monitoring unit). Alternatively, the personal identifier code may be any sequence of data uniquely associated with a user of a monitoring unit. The personal identifier code may be encoded upon a magnetic strip, upon an infrared signal, or upon a radio frequency signal.

According to one embodiment, the monitoring unit may require its user to wear an activity meter. An activity meter is a device that measures the activity level of a person wearing the meter and determines a numeric indication of that activity level. Examples of activity meters include pedometers, accelerometers, and calorie counters. A calorie counter is a device in which dietary input is entered, and on the basis thereof, calories consumed is arrived at. The monitoring unit may ask the user to enter readings from the activity meter so that this information may be transmitted to the remote computing system. Alternatively, the monitoring unit may interface directly with the activity meter so that the readings may be transmitted without intervention by the user. For example, with reference to FIG. 4, the activity meter may be interfaced with IO port 28 so that the information therein can be communicated directly to CPU 38. The activity meter may communicate with the monitoring unit via a radio frequency link, an infrared link, a wireless network, a wireless communication technology and protocol such as Bluetooth® which is a set of wireless technologies owned and made available from Bluetooth SIG Inc., or via a serial or parallel port embodied in a cradle, for example.

Activity meters provide a way for the monitoring unit and remote computing system to verify the answers provided by the user of the monitoring unit with respect to exercise levels. In some cases the readings provided by the activity meter may supplant any questioning regarding the exercise level of the person using the monitoring unit.

Activity meters may be used to gather information related to a person's activity level over a period of time, so that the information can be presented to that person. For example, the monitoring unit may prepare a status presentation that compares the person's present activity level to the person's activity level a week ago, two weeks ago, a month ago, six months ago, a year ago, or two years ago. Alternatively, the monitoring unit may compare the person's present activity level with the person's average (or median or other measure of central tendency) activity level over a past interval of time. The status presentation may be presented to the person via the output device of the monitoring unit. Alternatively, the status presentation may be e-mailed to the person (from the remote computing system, for example), may be made available to the person via a web site, may be presented via a printed report, or may be faxed to the person, for example.

A website may be provided as a front end access point to allow the person using the monitoring unit (or another designated person such as a health care provider, spouse, or parent) to access information collected by the monitoring unit. For example, the website may allow access to a database that stores information collected by the monitoring unit. The person gains access to the information in the database by entering a personal identifier, which is a set of data uniquely associated with the particular person. The database is accessed based upon the personal identifier, and one or more webpages are then presented to the person. The webpages may include indications of the person's weight loss progress (as discussed above), comparisons regarding the person's activity level (such as has been discussed above), or may present any of the information presented on the screen shown in FIG. 34. Alternatively, the indications of the person's weight loss progress, comparisons regarding the person's activity level, or any of the information presented on the screen shown in FIG. 34 may be communicated from the monitoring unit to a device such as a palm-top computer, a television set, or a telephone (e.g., via a modem) for presentation to a designated person.

Thus, it will be appreciated that the previously described versions of the invention provide many advantages, including addressing the needs in the medical profession for an apparatus and method capable of monitoring and transmitting weight loss and/or weight maintenance parameters of persons to a remote site whereby a medical professional caregiver can evaluate such physiological and wellness parameters and make decisions regarding the patient's treatment.

Also, it will be appreciated that the previously described versions of invention provide other advantages, including (according to certain embodiments) addressing the need for an apparatus for monitoring and transmitting such weight loss and/or weight maintenance parameters that is available in an easy to use portable integrated single unit.

Also, it will be appreciated that the previously described versions of the invention provide still other advantages, including addressing the need for medical professional caregivers to monitor and manage the patient's condition to prevent unnecessary weight gain and the occurrence of health problems that are concomitant therewith.

Although the invention has been described in considerable detail with reference to certain preferred versions thereof, other versions are possible.

Figure 36:
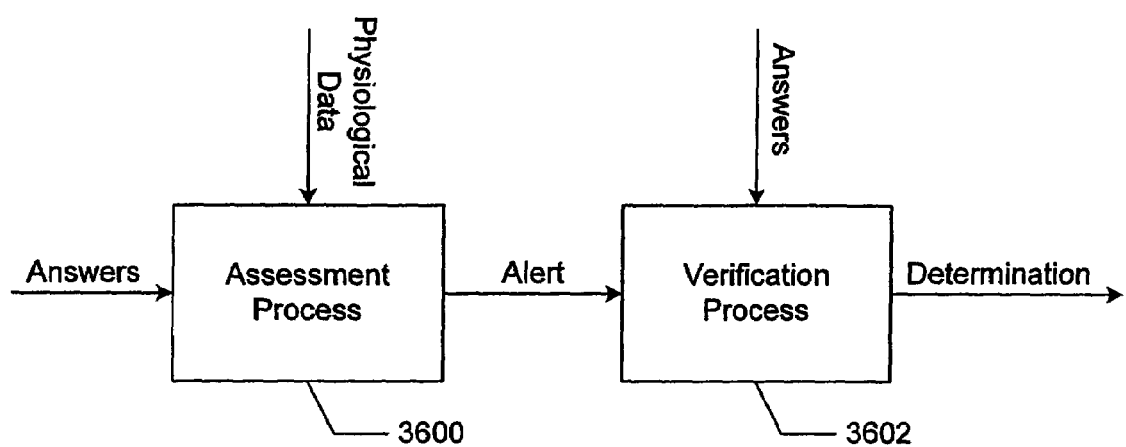
FIG. 36 depicts an interactive system of assessment and verification of an alert generated by a patient monitoring system, according to one embodiment of the present invention.

Automated Interactive Verification of an Alert Generated by a Patient Monitoring Device FIG. 36 depicts a patient monitoring scheme wherein an alert is initially generated, and subsequently verified. As can be seen from FIG. 36, the scheme includes two processes: an assessment process 3600 and a verification process 3602. According to the scheme of FIG. 36, a patient monitoring device (such as the patient monitoring devices 1100 or 2100 depicted in FIGS. 11 and 21, respectively) may be configured to measure at least one physiological parameter exhibited by a patient, and to prompt the patient with a set of questions. As described previously herein, the physiological parameter may include the patient's weight, the patient's blood glucose level, the patient's transthoracic impedance, etc. As also described previously herein, the questions may relate to the patient's perception of his or her physical condition (example: "Do your ankles exhibit swelling?" or "Do you feel shortness of breath when you exercise?").

Upon acquisition of the physiological data and patient answers, an initial assessment process 3600 is initiated. The assessment process 3600 may be performed by the patient monitoring device, or may be initiated by a remote computing system (such as the remote computing systems 1102 or 2100 depicted in FIGS. 11 and 21, respectively) with which the patient monitoring device communicates. The assessment process analyzes the patient answers and physiological data, as described previously herein, in order to arrive at a preliminary conclusion regarding whether the patient may need medical attention (for example, a preliminary conclusion may be drawn that the patient is experiencing an acute episode of a chronic disease, and therefore receive further medical attention). If the assessment process 3600 determines that the patient may need medical attention and/or further clinical triage, an alert is generated. As used herein, the terms "alert" and "exception" are synonymous.

In response to the generation of an alert, a verification process 3602 is initiated. The verification process 3602 involves analysis of both the data set (answers and physiological data) operated upon by the assessment process 3600 and additional data. The additional data may come in the form of additional patient answers to additional questions. On the basis of the original data set and the additional data, a determination is made whether the patient actually needs medical assistance.

Traditionally, the verification process 3602 has been performed by trained medical personnel, such as by a nurse, case manager or disease manager. Typically, a nurse obtains the original data set that was the basis for the alert, and examines the information therein. Thereafter, the nurse places a telephone call to the patient, and questions the patient further, in order to determine if further medical intervention is required.

On any given day, a call center may expect to observe an alert generated by 10%-20% of its telemonitored patient populace. A typical nurse can perform on the order of forty to fifty calls per day, meaning that a single nurse can manage on the order of 250 patients. From these figures, it can be seen that the number of patients a particular call center can manage is directly related to the number of nurses or operators employed. Unfortunately, nurses are oftentimes in short supply and may be expensive. Therefore, employment of a multitude of nurses tends to drive health care costs up, and perhaps prevents some of the populace from obtaining the health care services they need.

Figure 37:
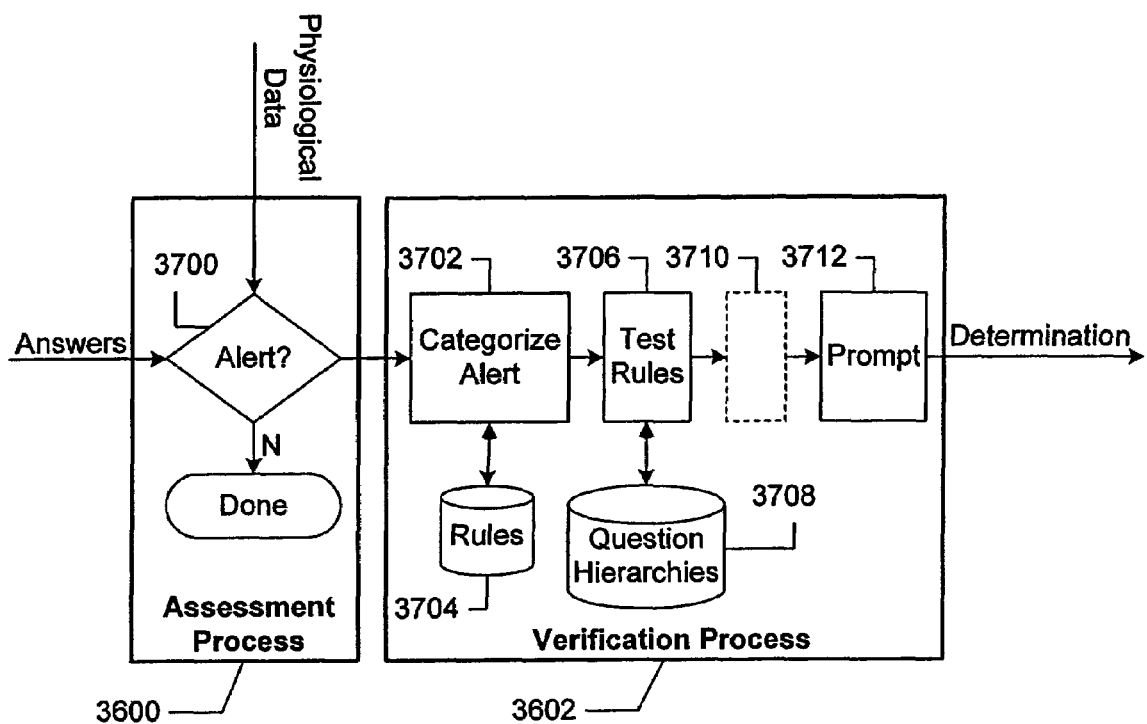
FIG. 37 depicts an embodiment of the system of FIG. 36, according to one embodiment of the present invention.

To address the aforementioned challenge, the verification process 3602 may be automated, so as to reduce or eliminate the need for nurse involvement in the process 3602. FIG. 37 depicts a kernel for automation of the assessment and verification scheme presented in FIG. 36.

The kernel depicted in FIG. 37 includes modules. The modules may be embodied as software, firmware, or hardware, such as one or more application-specific integrated circuits (ASICs), as is understood by those of skill in the art. As can be seen, the kernel of FIG. 37 includes modules for implementation of the assessment and verification processes 3600 and 3602 described with reference to FIG. 36. For example, the kernel includes an alert generation module 3700. The alert generation module 3700 receives the physiological data and answers from the patient, and determines whether an alert should be generated. Examples of processes by which this initial assessment may be made are disclosed above, and are therefore not presently reiterated. If no alert is generated, no verification is needed, and the process may halt. On the other hand, if an alert is generated, then a verification process 3602 is initiated. Such process may begin immediately after a single data element is input (such as a single answer or single physiological data element). Such a single element may begin the interactive assessment and verification process. Such an interactive process may also be used to provide immediate patient self-management feedback and recommendations. In other words, reception of a single answer or physiological parameter may constitute a sufficient basis upon which an assessment process may generate an alert. Accordingly, the verification process may commence after the reception of but a single answer or physiological parameter.

To effect verification 3602, the original data set, which was the basis of the alert, may be received by a categorization module 3702. The categorization module 3702 assesses the original data, in order to classify the alert in one or more categories. A category is a broad articulation of why the alert was generated. For example, an alert may be classified as a "high weight" alert, meaning that the alert was generated because the patient's weight exceeds some threshold. Thus, "high weight" is an example of a category. Additionally, an alert may be classified "symptom score" alert, meaning that the patient's answers corresponded to a score exceeding a threshold. Examples of schemes for scoring of a patient's answers and for comparison of the score to a threshold are described previously herein, and are therefore not presently discussed further. Other examples of assessments, categories and alerts are known, and other examples may readily present themselves to those of skill in the art. Furthermore, other examples may be derived and presented in many forms, which may include but are not limited to statistically validated surveys such as the Kansas City Quality of Life, SF-12, SF-36, and others. Such assessments, categories, and alerts are within the scope of the present invention.

In the wake of having classified the alert as falling into one or more categories, recognizing that a single alert may comprise its own category, a data store 3704 of rules is accessed. The data store 3704 contains a set of rules corresponding to each category. A rule or rule set is retrieved for each category in which the alert was classified. For example, if the alert was categorized as falling within two categories (e.g., "high weight" and "symptom score"), then two rule sets are retrieved (e.g., one rule set corresponding to "high weight" and another rule set corresponding to "symptom score"). However, according to some embodiments, one or more rules or rules sets may be retrieved in the absence of having categorized the alert. In any event, thereafter, the rule set(s) are passed to a testing module 3706. The testing module 3706 tests the original data set against each rule within each retrieved rule set, and identifies which rules are "triggered." A rule is said to be "triggered" if its assessment results in an affirmative result or a Boolean "1".

A rule set is composed of various rules that the original data set, and/or historical recordings of past original data sets, and/or other data collected by the central computing system may be tested against to better understand the nature and/or cause of the alert. Therefore, each triggered rule may correspond to a hypothesized nature or cause of the alert, which may, in turn, correspond to a line of questioning helpful in exploring the hypothesized nature or cause. For example, Table 6 (below) presents a rule set corresponding to a "high weight" alert.

TABLE 6

| | Rule Set: High Weight |
|---|---|
| Rule #1 | Minimal Weight Gain & No Alert Over Past 20 Days |
| Rule #2 | Minimal Weight Gain & Alert For Two Or More Days |
| Rule #3 | Minimal Weight Gain & Positive Weight Trend |
| Rule #4 | Minimal Weight Gain & Report Of Missed Medication |
| Rule #5 | Minimal Weight Gain & Medication Side Effect |
| Rule #6 | Minimal Weight Gain & Hospitalized in Past 14 Days |
| Rule #7 | Moderate Weight Gain & No Alert Over Past 20 Days |
| Rule #8 | Moderate Weight Gain & Alert For Two Or More Days |
| Rule #9 | Moderate Weight Gain & Positive Weight Trend |
| Rule #10 | Moderate Weight Gain & Report Of Salty Meal |
| Rule #11 | Moderate Weight Gain & Report Of Missed Medication |
| Rule #12 | Moderate Weight Gain & Medication Side Effect |
| Rule #13 | Moderate Weight Gain & Hospitalized in Past 14 Days |
| Rule #14 | Moderate Weight Gain & No Alert In Past 7 Days |
| Rule #15 | Significant Weight Gain |
| Rule #16 | Weight Gain For Two Or More Days |
| Rule #17 | Minimal Weight Gain & Report Of New Or Increased Symptoms |

TABLE 6-continued

Rule Set: High Weight

| | |
|---|---|
| Rule #18 | Moderate Weight Gain & Report Of New Or Increased Symptoms |
| Rule #19 | Moderate Weight Gain Exhibited Over A Single Day |
| Rule #20 | Minimal Weight Gain Exhibited Over Past Two Days |
| Rule #21 | Moderate Weight Gain Exhibited Over Past Two Or More Days |
| Rule #22 | Minimal Weight Gain For One Day & No Symptoms |
| Rule #23 | Minimal Weight Gain For One Day & Usual Symptoms Reported |
| Rule #24 | High Trigger Weight Change Within Minimal Weight Range & Current Weight Is Less Than Last Reported Weight |
| Rule #25 | Moderate Weight Gain Over High Weight Trigger & Weight Decreased From Previous Day & Usual Symptoms |
| Rule #26 | High Trigger Weight Change Within Minimal Weight Range & Current Weight Is Less Than Last Reported Weight & Hospitalized For CHF Within Past 14 Days |
| Rule #27 | Moderate Weight Gain Exhibited Over A Single Day & No Symptoms |

As mentioned previously, the testing module 3706 tests the original data set against each rule within each retrieved rule set, and identifies which rules are triggered. For each rule that is triggered, a question hierarchy is retrieved from a data store 3708. Of course, although FIG. 37 depicts data stores 3704 and 3708 as being distinct from one another, the data stores 3704 and 3708 may be embodied as a single data store. A question hierarchy includes a set of questions. Each question has an answer that may be selected from a set of discrete answers (e.g., "true-or-false," or "a, b, c, or d"). The question may be posed to the patient, who selects an answer from amongst the set of discrete answers. On the basis of the patient's answer, a subsequent question is posed, and/or an instruction is given, and/or a conclusion is reached, and/or an action is carried out. The answer to the subsequent question, and/or the outcome of the action undertaken determines the next question to be posed, and/or instruction to give, and/or conclusion to reach, and/or action to undertake, and so on. Each question hierarchy is configured to explore the hypothesized nature or cause deduced from a given triggered rule. Examples of question hierarchies are presented with reference to FIGS. 20-28 herein, and are therefore not presently discussed further. Of course, one skilled in the art of medical diagnosis may readily create question hierarchies directed to exploration of triggered rules, and such question hierarchies are within the scope of the present invention.

After retrieval of the question hierarchies from the data store 3708, some optional operations may be performed upon the hierarchies by an optional preparation module 3710. For example, the preparation module 3710 may inspect the retrieved question hierarchies for questions included in more than one such hierarchy. The preparation module may remove redundant questions, so that a given question is posed but a single time to the patient. Further, the preparation module 3710 may examine the question hierarchy to determine if any of the questions therein have already been posed to the patient prior to the initial assessment process 3600. If so, the answers thereto may be extracted from the original data set and inserted into an appropriate data space in the question hierarchy, so that the patient is not re-asked a question that he or she was asked by the monitoring device. Further, the preparation module 3710 may determine that the question hierarchy requires modification based on the patients co-morbidities. Further, the preparation module 3710 may examine prior questions posed to the patient and determine such new questions are inappropriate.

In the wake of operation of the optional preparation module 3710, the question hierarchies are presented to the patient via a prompting module 3712. According to one embodiment, the prompting module 3712 may guide an operator through a series of questions, which the operator poses to the patient via the telephone. For example, a first question may be presented to the operator via an output device. The operator may pose the question to the patient, obtain the patient's answer, and enter the answer via an input device, thereby obtaining a second question (or instruction, etc).

Alternatively, all of the modules 3700, 3702, 3706, 3710, and 3712 and data stores 3704 and 3708 may be programmed into a memory device in the patient monitoring apparatus. Alternatively, all of the modules 3700, 3702, 3706, 3710, and 3712 and data stores 3704 and 3708 may be programmed into an interactive television module or web interface. For example, the patient monitoring devices 1100 and 2100 presented in FIGS. 11 and 21 include memory devices 1112 and 2108, respectively. The aforementioned modules and data stores may be stored in the aforementioned memory devices 1112 and 2108, so that both the assessment process 3600 and the verification process 3602 are performed by the patient monitoring device.

Whether the modules are embodied in software/firmware stored in the patient monitoring device, or whether they are stored in the remote computing system, the outcome of presentation of the question hierarchies to the patient may include a determination of whether or not the patient needs to consult with a health care professional or otherwise see or speak with a physician or nurse. Other outcomes are possible. For example, the verification process 3602 may interact with software executed by the remote computing system. Such software is described in U.S. patent application Ser. No. 10/788,900, filed on Feb. 27, 2004 by Cosentino, and entitled "SYSTEM FOR COLLECTION, MANIPULATION, AND ANALYSIS OF DATA FROM REMOTE HEALTH CARE DEVICES," which is hereby incorporated by reference for all it teaches. According to one embodiment, the software is configured to interact with the verification process 3602, so as to automatically create a follow-up entry or an intervention entry, when appropriate. For example, if the question hierarchy arrives at a point whereby an instruction is given to the patient to increase his medication dosage, an intervention entry is automatically created reflecting this action. Similarly, if the question hierarchy arrives at a conclusion that a follow-up action must be taken in the future, a follow-up entry reflecting this conclusion may be automatically created.

Automatic Initiation of Data Transmission

According to one embodiment, the outcome of the verification process 3602 or assessment process 3600 may initiate a data communication (e.g., telephone call, page, short message service exchange, etc.) to medical office or call center. For example, traversal of a question hierarchy may lead to a conclusion that a nurse or other professional needs to be contacted, to schedule a medical appointment, for example, or for further assessment of the patient, or for other medical care plan management. At such a juncture, the patient monitoring apparatus automatically initiates a data transmission, telephone call, or other communication session to the appropriate network address, telephone number, or receiving location. For example, the data transmission may be carried out by a modem, telephone, cellular telephone, television, pager, hand-held wireless device, or other apparatus, that is integrated with, or otherwise in communication with, the patient monitoring device. An example of such a system is depicted in FIG. 38.

Figure 38:
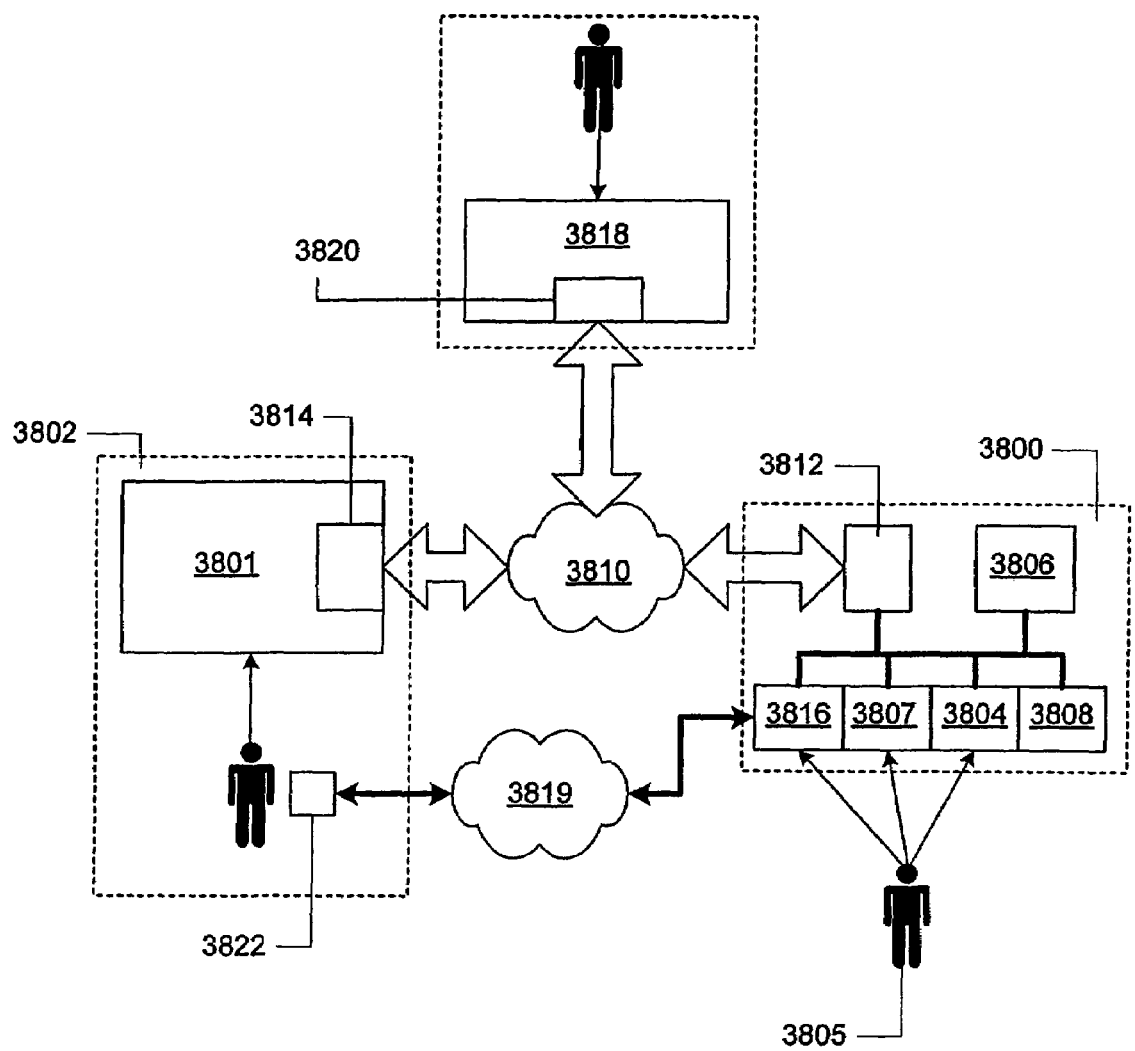
FIG. 38 depicts an embodiment of a patient monitoring system, according to one embodiment of the present invention.

FIG. 38 is a high-level depiction of a monitoring system employing the aforementioned embodiment. As can be seen from FIG. 38, the system comprises a patient monitoring apparatus 3800, a central computer 3801, and a computer system 3818 located at an oversight association, such as an HMO. The central computer 3801 is housed within a facility 3802 that is located remote from the patient monitoring apparatus 3800. For example, the patient monitoring apparatus 3800 may be located in the home of an ambulatory patient 3805, while the central computer 3801 is located in a call center, disease management company or health care facility 3802. The central computer may be coupled to a communication network 3810 or 3819, such as to the Internet, public switched telephone network, or other network.

As described previously, the patient monitoring apparatus 3800 is composed of a central processor unit 3806, which is in communication with an input device 3807, an output device 3804, and a memory device 3808. The memory device 3808 may have each of the modules and data stores described with reference to FIG. 37 stored therein. Additionally, the memory device 3808 may have a telephone number or network address, etc. to contact in the event that a nurse follow-up telephone call or communication session is necessitated stored therein.

As discussed previously, the output device 3804 may be used to prompt the patient 3805 with questions regarding the patient's wellness and may also provide immediate feedback to the patient based on such answers. The output device 3804 may consist of a visual display unit such as LCD, touchscreen or television that displays the questions in a language of the patient's 3805 choosing. Alternatively, the output device 3804 may consist of an audio output unit that vocalizes the questions and combined with an input device such as an interactive voice response system records such answers. In one embodiment, the audio output unit 3804 may vocalize the questions in a language of the patient's 3805 choosing. As yet another alternative, the input device 3807 and output device 3804 may be embodied jointly as an interactive voice response system.

The patient monitoring apparatus 3800 communicates with the central computer 3801 via a network 3810; the patient monitoring apparatus 3800 uses a communication device 3812 to modulate/demodulate a carrier signal for transmission via the network 3810, while the central computer 3801 uses a communication device 3814 for the same purpose. Examples of suitable communication devices 3812 and 3814 include internal and external modems for transmission over a telephone network, network cards (such as an Ethernet card) for transmission over a local area network, a network card coupled to some form of modem (such as a DSL modem or a cable modem) for transmission over a wide area network (such as the Internet), or an RF transmitter for transmission to a wireless network. Of course, the oversight association's computer 3818 may use a similar communication device 3820 for the same purpose, as well. The patient monitoring device 3800 may include a physiological parameter transducer (not depicted) in data communication with the processor 3806. Alternatively, the patient monitoring device 3800 may couple to an external physiological parameter transducer through an input/output port, for example. Alternatively, the patient monitoring device may communicate via telemetry, RF transmission, or other wireless means with an implanted device such as a pacemaker, defibrillator or synchronization device as described above in the present document. For example, a portion or all of the physiological parameter data may be communicated to the patient monitoring device from an implantable medical device, such as a pacemaker, defibrillator, cardiac resynchronization therapy (CRT) device, stimulator, etc. Additionally, the patient monitoring device 3800 may exclude a physiological transducing unit altogether.

If during traversal of the question hierarchies, it is determined that a data transmission should be initiated with a medical attendant (e.g., a nurse, physician, health care attendant, etc.), then the patient monitoring device 3800 may initially transmit the data set operated upon by the verification process (or some subset thereof) to the central computer system 3801 (this is an optional step).

Next, the patient monitoring device 3800 may attempt to establish a two-way communication session with a nurse or other professional at the call center, clinic, etc. 3802. The two-way communication session may occur as a computer-to-patient monitoring device session transacted through the network 3810. Per such a scenario, the nurse or other professional could observe the data set initially transmitted to the central computer 3801, and could then join the electronic two-way communication session to make further inquiry of the patient 3805.

Alternatively, the patient monitoring apparatus may make use of another communication device 3816, by which a communication session is initiated with another communication device 3822 accessed by the professional at the call center 3802. For example, the communication device 3822 may be a telephone, a cellular telephone, a pager, a Blackberry® device, or other wireless communication device. The communication device 3816 utilized by the patient monitoring device 3800 may initiate a communication session with the professional's device 3822, so that two-way communication may be established. Per this scenario, the data set operated upon by the verification process (or some subset thereof) may be transmitted from the patient monitoring device 3800 to the professional's communication device 3822. As an alternative, the central computing system 3801 may communicate the information to the professional's communication device 3822. In either event, at the time that the two-way communication session is initiated, the professional has access to the information, so that the professional has data that serves as the basis for further inquiry of the patient 3805.

In the event that the communication device 3816 is embodied as a telephony device, then the processor 3806 may initiate a telephone call via a telephone unit 3816 under control of the processor 3806. The telephone unit 3816 may be instructed of the appropriate number to call by the processor 3806, or may be preprogrammed to call a specific telephone number. Thus, immediately at the time the question hierarchy is interacting with the patient, a nurse may be called, thereby saving the nurse time and effort of having to initiate the telephone call. In the event that the communication device 3812 is a telephone modem, the telephone unit 3816 may be integrated as a part of the modem 3812, with an external speaker and microphone coupled thereto for facilitation of conversation between the nurse and the patient. Alternatively, if embodied as a distinct device, the unit 3816 may include a speaker and microphone suitable for enablement of "speaker phone" communication.

It is possible that, for one reason or another, the two-way communication session cannot be established (example: communication devices 3816 and 3822 are telephonic devices, and the call center's 3802 telephone lines are busy). In such an instance, subsequent re-attempts to establish the communication session may be initiated by the patient monitoring apparatus 3800. If, however, a threshold number of re-attempts (e.g., twelve re-attempts) prove fruitless, then a data transmission may be made to the computer system 3818 at the oversight association. According to one embodiment, the patient monitoring device initiates the data transmission to the computer system 3818, and transmits a data packet containing content sufficient to inform that oversight association's computer 3818 that the patient 3805 has not yet been contacted. According to one embodiment, the aforementioned data packet may have a unique code associated therewith. Thus, when a two-way communication session is finally established between the patient and the professional, a corresponding code may be transmitted from the professional's communication device 3822 or computer system 3801 to the oversight association's computer 3818 to confirm that the patient 3805 has been contacted.

Parameter Adjustment

Figure 39A:
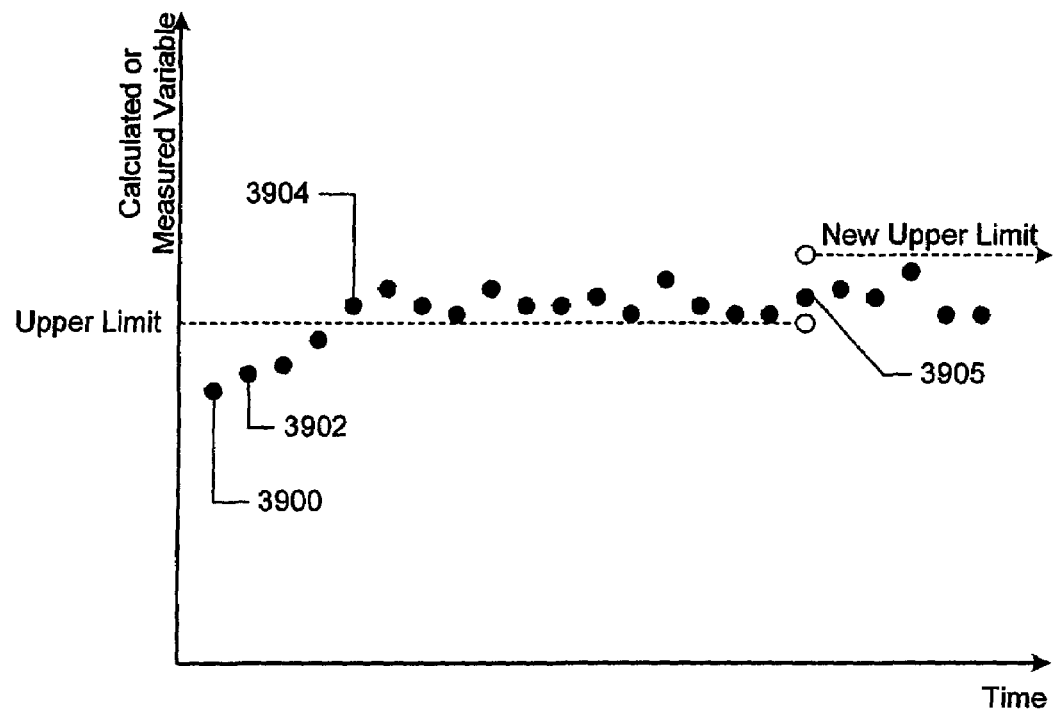
FIG. 39A depicts a Cartesian plane presenting a measured or calculated parameter that is compared with a threshold.

When managing large patient populations, constant parameter adjustment is required. Such parameter adjustment for biometric measurements, symptom thresholds and other parameters requires a skilled resource and can be time intensive. The central computing system (such as computing system 3801) may be programmed to automatically readjust certain parameters from time to time. The graph depicted in FIG. 39A presents a background for understanding this feature. A Cartesian plane is depicted in FIG. 39A, with a measured or calculated variable presented along the y-axis, and successive measurements presented along the x-axis. The measured variable describes a quantifiable condition or state of the patient's body. For example, the measured variable may be weight, blood glucose, blood oxygen level, blood pressure, transthoracic impedance (examples of measured variables), or may be a score describing a patient's self-reported symptoms (an example of a calculated variable). Oftentimes, such scores are monitored as a part of the assessment process 3600 (FIG. 36), as has been described above. An alert may be generated when the score exceeds a threshold (or falls beneath a threshold), when a score exhibits a sustained trend (e.g., weight increase exhibited over the span of at least N days), or when a score as measured or calculated on a given day differs from a score as measured or calculated on a previous day by more than a prescribed quantity, etc.

Notably, each of the aforementioned sorts of variable monitoring schemes shares a common premise, namely, that a change in the monitored variable's value corresponds to a change in the chronic condition being monitored. Sometimes, however, this premise is incorrect. For example, a patient's weight may vary because the patient is experiencing an acute episode of pulmonary edema, in which case the premise is correct—the change in the patient's weight over time reveals a change in the state of the chronic condition. On the other hand, a patient's weight may vary over time because the patient has gained or lost fatty or muscular tissue. Per such a scenario, the change in the patient's weight is unrelated to the chronic condition being monitored.

As mentioned above, in some instances an alert may be generated in the event that the measured variable exceeds or falls short of a threshold. Such a strategy may prove unreliable in the situation where the monitored variable has exhibited change for reasons unrelated to the chronic condition being monitored. With respect to FIG. 39A, one may assume, for the sake of illustration, that the measured variable is a patient's weight, and that each darkened dot on the Cartesian plane represents a given daily weight measurement for a particular patient. Thus, point 3900 represents a particular patient's weight on a given day, and point 3902 represents the patient's weight as measured on a successive day, and so on.

Examination of the graph of FIG. 39A reveals that on the day that the point 3904 was measured, the patient's weight exceeded an upper limit threshold, meaning that the initial assessment process 3600 (FIG. 36) would have generated an alert or exception that day. In response thereto, a verification process 3602 (FIG. 36) would have been initiated, and for the sake of illustrating the foregoing concepts, one may assume that the verification would have turned out to be negative (i.e., an interview of the patient would reveal that the patient did not need medical attention). As shown in FIG. 39A, a similar result would have occurred for fourteen consecutive days.

After two weeks of generating an alert, and thereby initiating a verification process, the software on the central computing system (or patient monitoring device, if implemented thereupon) may be programmed to re-establish a new threshold, as shown in FIG. 39A. The premise for the re-establishment is that the patient has simply gained weight, and is not experiencing edema, so the upper limit should be modified.

Figure 39B:
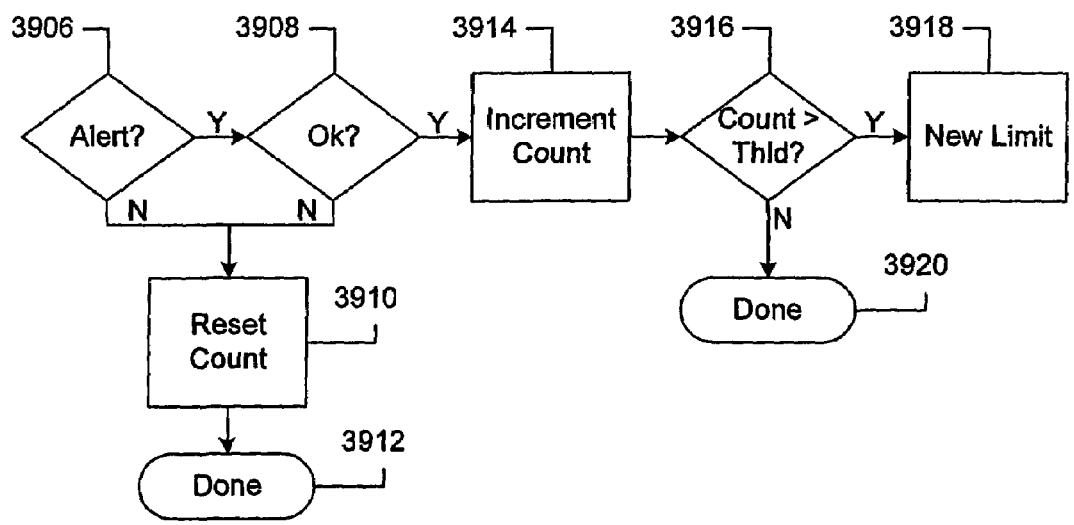
FIG. 39B depicts a scheme for altering the threshold depicted in FIG. 39A, according to one embodiment of the present invention.

FIG. 39B depicts one method for altering a threshold. As shown therein, the process begins by determining whether, for a given monitored parameter, that parameter has caused an alert during the assessment process 3600 (FIG. 36), as shown in operation 3906. If so, control is passed to operation 3908, whereupon it is determined whether the subsequent verification process 3602 (FIG. 36) has shown the patient to not be in need of medical assistance. If the answer to either of these inquiries 3908 is in the negative, then control is passed to operation 3910, whereupon a count variable is reset to zero, and the process is halted (operation 3912). On the other hand, if the answer to both of the inquiries of operations 3906 and 3908 is in the affirmative, the count variable is incremented (operation 3914), indicating that another day has transpired whereby a particular variable generated an alarm, but the patient has proven to be in satisfactory condition.

In operation 3916, the count variable is compared against a threshold, which may be selectable. For example, the threshold may be equal to fourteen days, as shown in the example of FIG. 39A. If the count variable exceeds the threshold, the threshold(s) against which the variable is tested for generation of an alert may be adjusted (operation 3918). Otherwise, the process is halted (operation 3920).

There exist many possibilities for adjusting such a threshold. For example, the software may be programmed to find a measure of central tendency over a span of the preceding N days. Then, an offset variable may be added (and/or subtracted) to the central tendency, to generate a new upper threshold and/or lower threshold. For example, in the context of the graph of FIG. 39A, execution of operation 3918 may include finding the average patient weight over the fourteen-day period preceding the measurement of point 3905. Then, an offset variable may be added to the average value, creating an upper threshold limit, and an offset value may be subtracted therefrom, yielding a lower threshold limit. Of course, other measures of central tendency may be used, such as arithmetic mean, geometric mean, median, etc. Also, other schemes for adjusting a threshold on the basis of observed historical data may readily present themselves to ones of ordinary skill in the art, and are within the scope of the present invention.

Assessment of Questions

As described with reference to FIG. 36, the assessment and verification processes consist, in large part, of analysis of a patient's answers to questions. Consequently, the assessment and verification processes are only as good as the questions that are asked. To ensure that informative questions are asked, a system may be configured to ask a great multitude of questions, in the hope that at least some of them will be informative. On the other hand, such a strategy exhibits a drawback: the patient tires of answering the great number of questions.

Figure 40A:
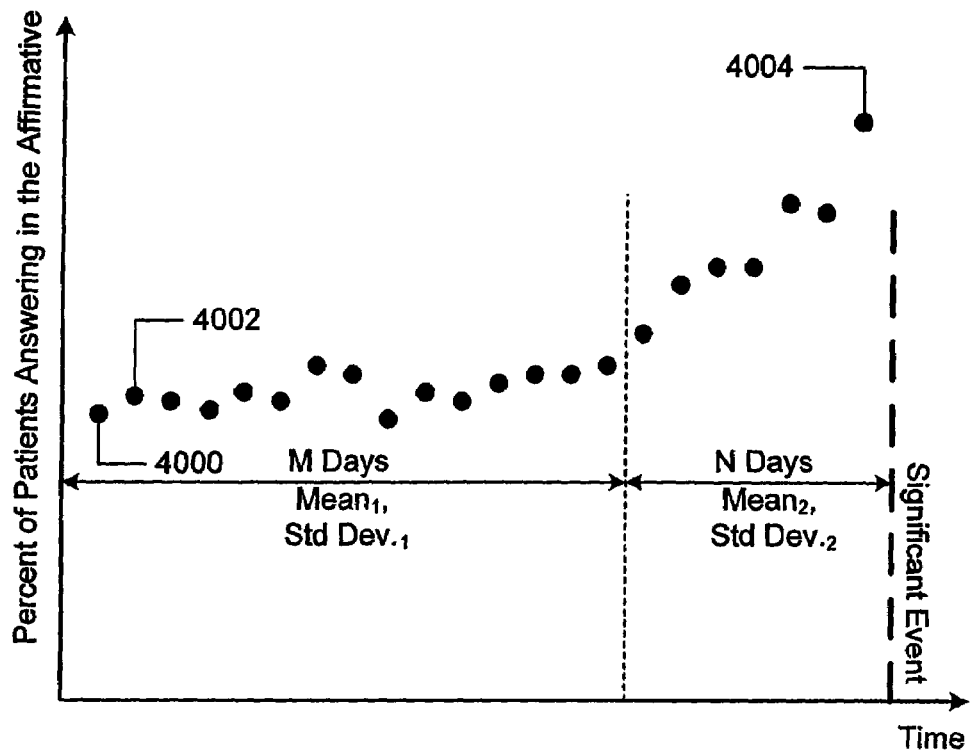
FIG. 40A depicts a Cartesian plane the effectiveness of a given question in predicting the onset of a medically significant event, according to one embodiment of the present invention.

To address this issue, it may be desirable to have a tool by which to gain insight into the effectiveness of a question with respect to its ability to predict the onset of a significant health care related event (e.g., hospitalization). FIG. 40A depicts a chart that provides the illustrating concepts upon which such a tool may function.

FIG. 40A depicts a Cartesian plane that presents data revealing the effectiveness of a given question in predicting the onset of a significant health care related event for a given patient population. The Cartesian plane has a plurality of darkened dots presented therein. Each darkened dot represents the percentage of the given patient population answering the given question in the affirmative (measured along the y-axis) on a given day (measured along the x-axis). Thus, point 4000 represents the percentage of the patient populace answering the given question in the affirmative on a given day, and point 4002 represents the percentage of the patient populace answering the given question in the affirmative on a successive day.

A vertical dashed line on the chart represents the point in time at which the patient populace experienced a significant health care related event. For the sake of illustration, the dashed line is referred to herein as representing a day on which each patient in the patient populace was hospitalized. Accordingly, the point 4004 preceding the dashed line represents the percentage of the patient populace answering a question in the affirmative on the day preceding hospitalization.

As can be seen from FIG. 40A, for the given patient population measured by the chart therein, the percentage of the patient populace answering the question in the affirmative on a given day increases dramatically in the days immediately preceding hospitalization. It is therefore fair to conclude that the particular question corresponding to the chart of FIG. 40A is an effective predictor for the particular patient population. According to one embodiment, the central computing system may be programmed to create and display a chart such as the one depicted in FIG. 40A.

Figure 40B:
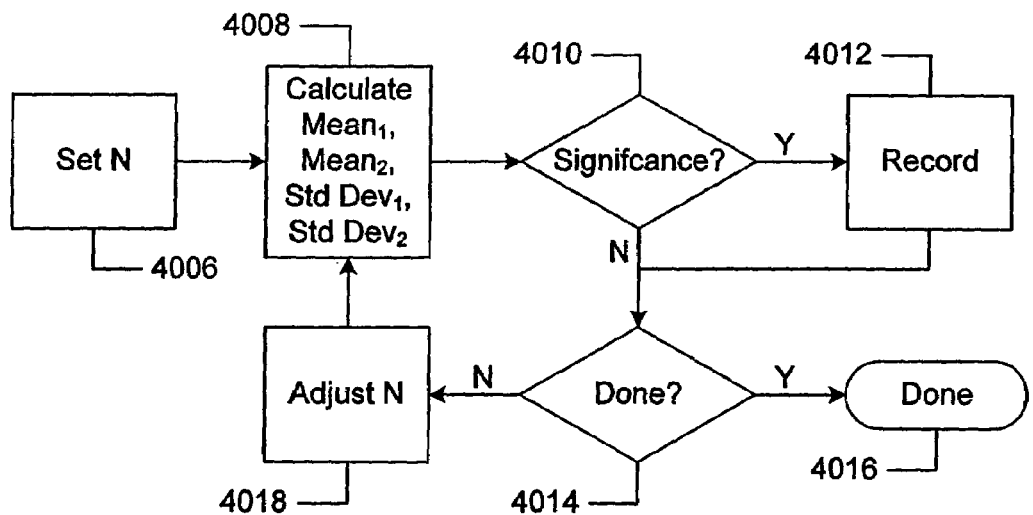
FIG. 40B depicts a scheme for assessing data, such as that expressed in the chart of FIG. 40A, according to one embodiment of the present invention.

FIG. 40B depicts an example of a method by which the effective of a question may be measured. The method begins with selection of variables M and N, in operation 4006. N represent the number of points preceding hospitalization to be considered for formulation of statistics describing a group to be assessed for effectiveness. M represents the number of points preceding the assessment group to be considered for formulation of statistics describing a control group. For example, if N=7 and M=10, then operations 4008, 4010, and 4112 cooperate to determine whether a given question appears to predict the onset of hospitalization up to seven days prior thereto, when considered in light of a control group of ten data immediately preceding points.

Next, in operation 4008, the mean and standard deviation of the set of N points and the set of M points are calculated. Thereafter, as shown in operation 4010 the median of the set N of points is compared against the median and standard deviation of the set of M points. If the median of the set of N point falls more than a given number of standard deviations away from the median of the set of M points, the question is deemed to have significance, and the data may be recorded, as shown in operation 4012. Thereafter, it is determined whether the analysis process is complete, as shown in operation 4014. If so, the process halts (operation 4016).

On the other hand, if the process is to continue, then N is adjusted (operation 4018), and control returns to operation 4008, and the process continues as described above.

Cooperation with Implanted Device

Figure 41:
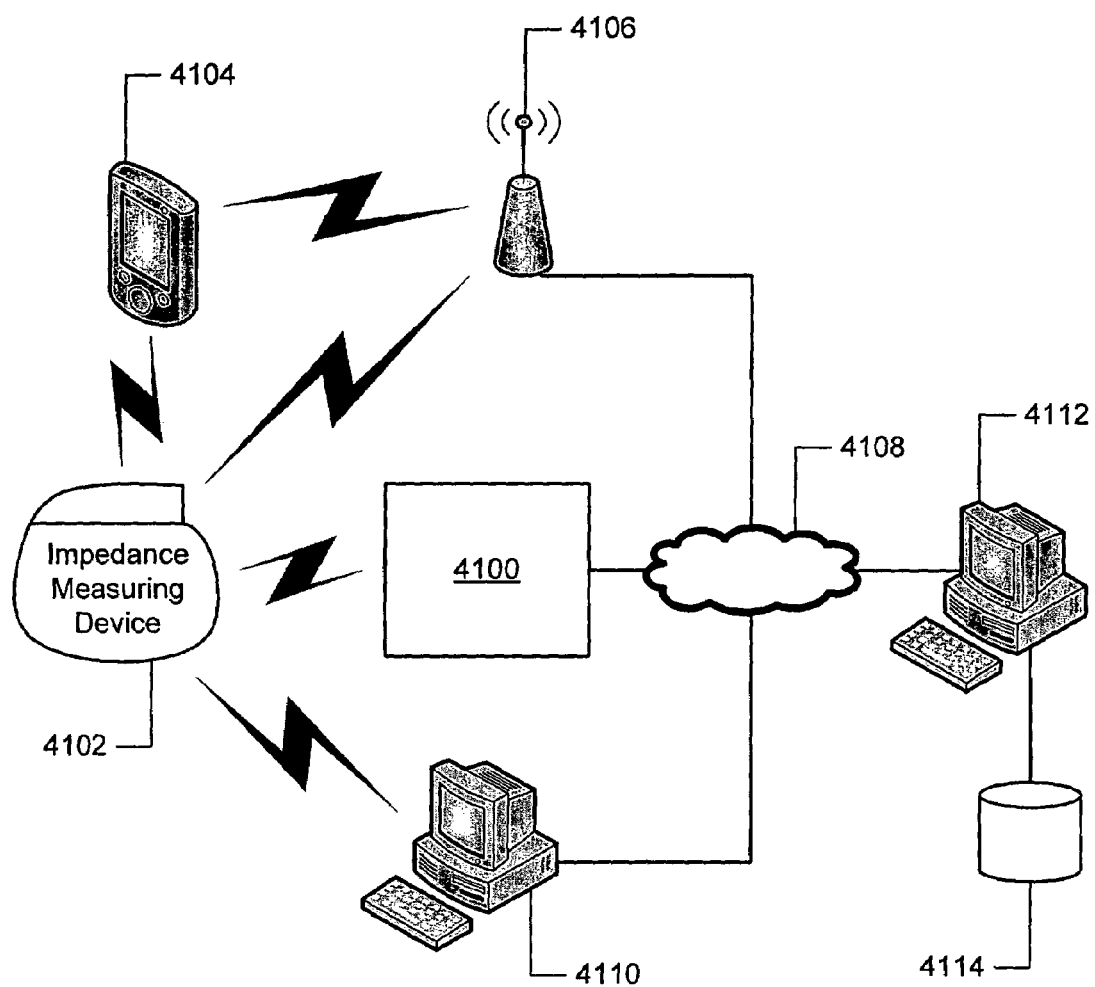
FIG. 41 depicts a patient monitoring device that cooperates with an implanted device 4102, according to one embodiment of the present invention.

FIG. 41 depicts a patient monitoring device 4100 (such as the patient monitoring devices 1100, 2100, or 3800 depicted in FIGS. 11, 21 or 38, respectively) that cooperates with an implanted device 4102. For example, the implanted device 4102 may be a cardiac rhythm management device, such as a pacemaker, cardiodefibrillator, resynchronization device, or congestive heart failure (CHF) device. Alternatively, the implanted device 4102 may be any other implanted medical device, such a bioimpedance measuring device, a transthoracic impedance measuring device, an infusion pump, etc. For the sake of discussion only, the implanted device 4102 is depicted and discussed herein as being a cardiac rhythm management device.

Figure 42:
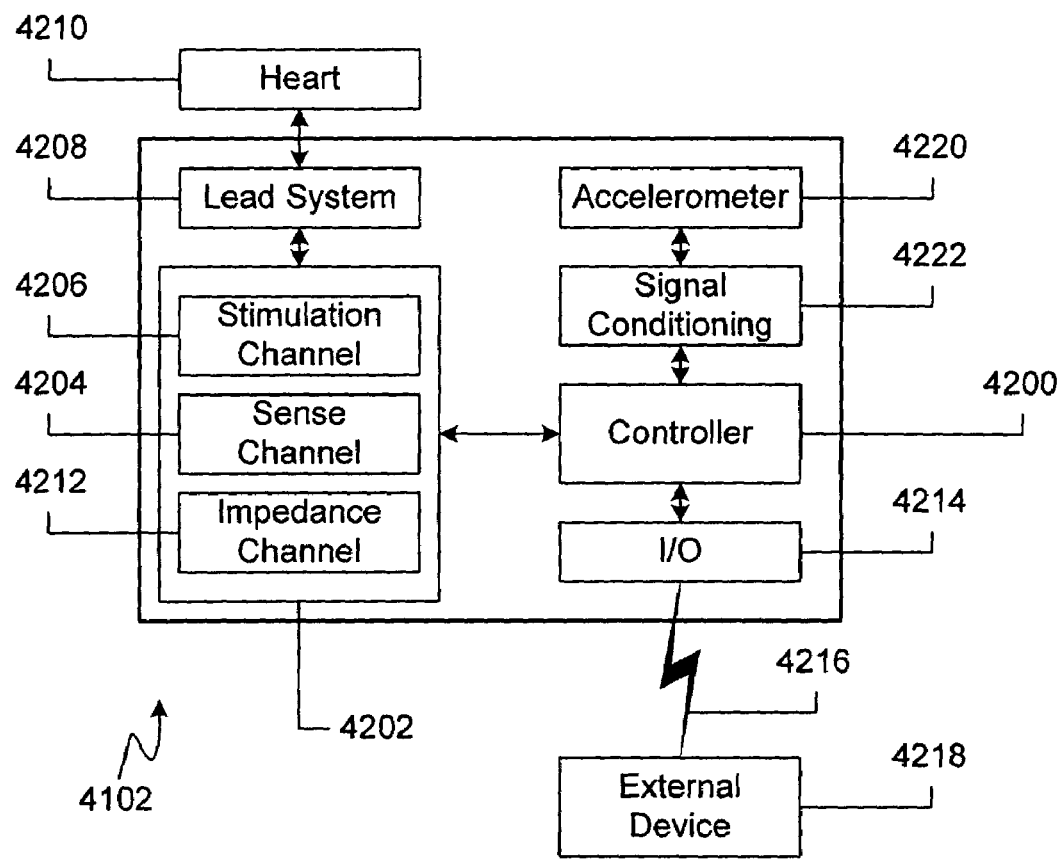
FIG. 42 depicts a simple example of a cardiac rhythm management device.

For the sake of generally orienting the reader regarding a cardiac rhythm management device, FIG. 42 depicts a simple exemplary embodiment of such a device. As can be seen from FIG. 42, a cardiac rhythm management device 4102 typically includes a controller 4200 that controls the device 4102. The controller 4200 may include a microprocessor and various memory units, or may be embodied as an application-specific integrated circuit (ASIC). For example, the controller 4200 may include multiple memory units, such as a flash memory in which firmware for controlling the operation of the device is stored, and a random access memory (RAM) into which various values with which the firmware interacts are stored. The RAM may store values that have been measured by the device 4102, thereby developing a data set, as discussed below.

The controller 4200 is coupled to a channel system 4202, which is interposed between the controller 4200 and a lead system 4208. The lead system 4208 is, in turn, coupled to a patient's heart 4210. The channel system 4202 serves as an interface between the controller 4200 and the lead system 4210.

The channel system 4202 may include a stimulation channel 4206 by which the controller 4200 may command the device 4102 to deliver a stimulation pulse to the heart 4210. Additionally, the channel system 4202 may include a sense channel 4204 by which the controller 4200 may detect the electrical activity of the heart 4210 (e.g., may detect depolarization of the heart 4210, for example). The channel system 4202 may include more than one sense and stimulation channel 4204 and 4206. For example, in the context of a dual-chamber device, the channel system may include both ventricular and atrial sense and stimulation channels.

According to one embodiment, the device of FIG. 42 measures transthoracic impedance. By way of background, it is known that thoracic impedance is inversely proportional to thoracic fluid volume, i.e., pulmonary fluid. This inverse relationship exists because pulmonary fluid is characterized by greater conductivity than the various tissues that otherwise fill the thorax. Thus, as thoracic fluid content increases, transthoracic impedance decreases. Accordingly, a reduction in transthoracic impedance may correspond to an increase in thoracic fluid content, which, in turn, may indicate impending decompensated heart failure for a given patient.

According to one embodiment, the device 4102 of FIG. 42 measures transthoracic impedance using the lead system 4208. For example, the device may include an impedance-measuring channel 4212 that communicates information related to measured transthoracic impedance to the controller 4200. The impedance-measuring channel 4212 may be embodied as a separate channel, may be embodied as a part of the stimulation and/or sense channels 4204 and 4206, or may be embodied as a portion of a channel devoted to measuring respiration, for example.

As the cardiac rhythm management device 4102 operates, it generates a data set that characterizes various physiological aspects of the patient, and describes the operation and/or response of the device 4102. For example, the device 4102 may periodically, or upon command, measure the transthoracic impedance exhibited by the patient, and may store such measurements. Optionally, the controller 4200 may calculate a long-term average and/or short-term average of the transthoracic impedance exhibited by the patient over a period of time. The long-term average may be used as a reference point against which the short-term average is compared, in order to determine whether the patient's transthoracic impedance is abnormally depressed. The long-term average, short-term average, and each of the individual impedance measurements constitute a portion of the data set generated by the cardiac rhythm management device, for example. Other elements of data may be present within the data set developed by the device 4102. For example, the device 4102 of FIG. 42 includes an accelerometer 4220, which generates a signal in proportion to its own acceleration. The accelerometer is coupled to the controller 4200 via a signal conditioning system 4222. The signal conditioning system 4222 is configured to filter the signal from the accelerometer to yield frequencies within bands of interest, in light of the information to be gleaned from the accelerometer (of course, the signal conditioning system 4222 may include an analog-to-digital converter and/or level shifters, etc., necessary for interface with the controller 4200). Thus, during operation, the accelerometer 4220 may deliver information to the controller 4200 regarding the physical activity of the patient. According to one embodiment, the accelerometer information, or a portion thereof, or a value derived therefrom (such as one or more averages describing physical activity throughout various portions of the day), is stored by the controller 4200. The stored accelerometer information thereby becomes a part of the data set developed by the device 4102. Furthermore, the accelerometer 4220 may be used to detect heart sounds present within a cardiac cycle. (In such instances, the accelerometer 4220 may be external to the device, and may be located at the distal end of a lead within the lead system 4208. Alternatively, the device may include two accelerometers—an internal accelerometer for detecting physical activity of the patient, and an external accelerometer for detecting heart sounds). Heart sound information, such as amplitude, shape, and/or frequency information concerning the S1, S2, S3, and/or S4 heart sounds may be stored and may constitute a portion of the data set developed by the device 4102. Still further, as alluded to earlier, the device may measure transthoracic impedance in order to obtain information concerning the patient's respiration (e.g., rate, volume, etc.). (It is known that a transthoracic impedance signal contains information concerning thoracic fluid volume within its low frequency bands, and contains information concerning respiration in its relatively higher frequency bands. Thus, various filtering mechanisms may be employed to extract the information of relevance, depending upon whether thoracic fluid volume or respiration information is sought.) Information concerning the patient's respiration throughout various periods of the day may also be stored as a part of the data set developed by the device 4102. Still further, it is known for a cardiac rhythm management device 4102 to generate event markers that indicate the time and date on which the device 4102 observed a particular cardiac rhythm abnormality. The event markers may also constitute a part of the data set developed by the device 4102.

The cardiac rhythm management device 4102 includes an input/output (I/O) channel 4214. The I/O channel 4214 establishes a communication link 4216 with an external device 4218. The communication link 4216 may, for example, be an RF link, such as an RF link according to the IEEE 802.11 standards, may be an inductive link, or may be any other form of suitable link. The communication link 4216 permits the data set developed by the device 4102 to be delivered to another device that develops its own data set, whereupon the two data sets may be commingled, and whereupon the two data sets may be usefully analyzed for the purpose of extracting reliable predictive and/or diagnostic information concerning the patient (this is discussed at greater length, below).

Returning to FIG. 41, four examples of external devices 4218 with which the cardiac rhythm management device 4102 may communicate are depicted. For example, the cardiac rhythm management device 4102 may communicate with the patient monitoring device 4100. Alternatively, it may communicate with a wireless device 4104, such as a personal digital assistant (PDA) outfitted with a suitable communication interface to communicate with a wireless access point 4106. Thus, data communicated from the cardiac rhythm management device may be relayed to a wired network 4108, and may ultimately reach any device coupled to the network 4108. Further, the cardiac rhythm management device 4102 may communicate with a programmer 4110 (such as a programmer that is typically found in a doctor's office for the purpose of reprogramming and interrogating the cardiac rhythm management device 4102), which may, in turn, communicate the data through a network 4108.

By virtue of communicating with an external device 4218 (such as wireless device 4104, patient monitoring device 4100, or programmer 4110) that is coupled to a network 4108, the data set maintained by the cardiac rhythm management device 4102 may be commingled with the data set developed by the patient monitoring device 4100. The data sets may be commingled in any of the devices 4100-4114 coupled (directly or indirectly) to the network 4108. According to one embodiment, the data sets are commingled by a server 4112 in data communication with a data store 4114. The server 4112 may be accessed by health care professionals that provide medical services to a given patient. Thus, according to one embodiment, the server 4112 includes a secure web server, that permits retrieval of information stored within the data store 4114. According to another embodiment, the data sets are initially commingled by the patient monitoring device 4100. Per this embodiment, the patient monitoring device 4100 is configured to communicate with the cardiac rhythm management device 4102, and can both read data therefrom (e.g., can interrogate the device 4102), and can optionally write data thereto (e.g., may have complete or limited ability to program the device 4102). Upon commingling, the two data sets provide information from which various medical conclusions about the patient may be drawn. For example, as discussed below, the two data sets jointly provide information that may reliably indicate and/or predict decompensation of heart failure.

Figure 43:
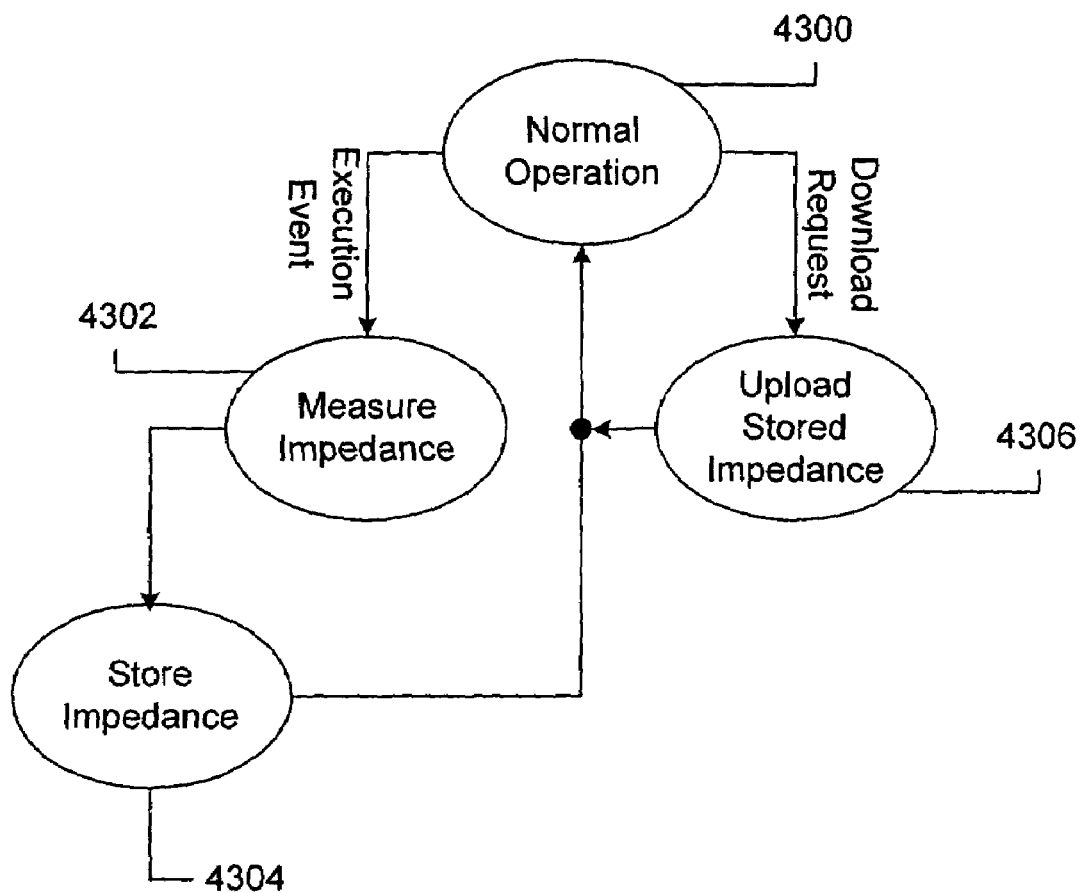
FIG. 43 depicts a state transition diagram for the generation of a measurement, according to one embodiment of the present invention.

As mentioned previously, the cardiac rhythm management device generates a data set during its operation. According to one embodiment, the data set generated thereby is constructed according to the method depicted in FIG. 43. As can be seen, from FIG. 43, the method of data set construction begins with the device acting according to its normal operation, as shown in state 4300. Thereafter, an execution event occurs, which causes the device to transition to measurement state 4302 (which is titled "Measure Impedance" for the sake of example, but refers to any measurement which might be taken by the device). The execution event causing the state transition refers to any event appropriate to initiate the taking of a measurement. The execution event may be, for example, the occurrence of a specific time of day (e.g., a measurement is always taken at 3:00 AM or 12:00 PM), or may be the detection or a rhythm abnormality (e.g., the device detects the onset of atrial or ventricular fibrillation, or detects a synchronization abnormality between the various chambers of the heart). According to another embodiment, the execution event is a command from the patient monitoring apparatus, meaning that the patient monitoring apparatus commands the taking of a measurement, such as an impedance measurement, thereby causing transition to state 4302. In instances in which a measurement is sensitive to factors that may vary throughout the day (example: posture), it may be advantageous to have the measurement initiated by command of the patient. For example, thoracic impedance measurements are known to be sensitive to, amongst other things, patient posture (the thoracic cavity tends to fill with fluid as a person reclines, meaning that even a healthy person exhibits an impedance drop when reclining). Therefore, according to one embodiment, the patient monitoring device is fashioned as a scale, as depicted in FIGS. 1A-1E. The patient weighs himself, using the patient monitoring device, answers questions posed by the device, and initiates measurement of transthoracic impedance (the measurement is initiated by virtue of a command transmitted from the patient monitoring apparatus to the device). At the time the measurement is initiated, the patient is known to be standing on the scale, meaning that variability of transthoracic impedance known to occur from posture is eliminated. The device responds by taking the measurement, and storing the measurement, as shown in state 4304. Thereafter, the device returns to normal operation state 4300.

Upon returning to normal operation state 4300, the device may be partially or entirely interrogated by the patient monitoring apparatus. For example, the patient monitoring apparatus may request that only specific data items be transmitted from the device to the apparatus (example: the apparatus may request that only impedance measurements be transmitted from the device to the monitoring apparatus). On the other hand, the patient monitoring apparatus may request a complete interrogation procedure, so as to read all of the data stored therein. In the wake of operation 4306, the data set generated by the cardiac rhythm management device is commingled with the data set generated by the monitoring apparatus within the memory of the apparatus. Upon commingling of the data sets, significant conclusions regarding the medical status of the patient may be drawn. Prior to discussion regarding the drawing of conclusions, it should be noted that the data sets developed by the patient monitoring apparatus and the cardiac rhythm management device may commingle in any computing environment depicted in FIG. 41. Another point should be noted. It is within the scope of this disclosure to program any of the devices in FIG. 41 to pose the questions, and/or to execute the methods disclosed herein. For example, the PDA 4104 may be programmed to pose the question sets disclosed herein, and to implement the methods disclosed herein. Since the PDA lacks a scale, the PDA may simply prompt the patient to weight himself, and to enter the measurement. On the other hand, the PDA may contain an interface (example: RF interface to communicate with a scale) permitting communication with a scale. Weight measurements are communicated from the scale to the PDA through the communication link. Once completed, the PDA may travel with the patient, meaning the patient may interact with his device through the PDA throughout the day, and that the patient may answer questions through the PDA at any time throughout the day (the questions may be created dynamically by health care professionals, as discussed with reference to the two-way messaging portions disclosed herein, for example).

At any of the devices having access to both the data set generated by the cardiac rhythm management device and the data set generated by the patient monitoring apparatus, the following conclusions may be drawn (it is understood that other conclusions may be drawn as well).

Transthoracic impedance tends to be an early indicator of decompensated heart failure. However, as noted above, impedance measurements may falsely indicate the accumulation of heart failure for a variety of reasons (example: if the measurements are taken with leads implanted in the heart, the measurements may be subject to rhythmic physiological cycles, such as the cardiac rhythm and respiration cycle, the effects of which may be only partially filtered out). On the other hand, patient weight is known to be another indicator of decompensated heart failure. Occasionally, a patient with decompensated heart failure does not exhibit a significant weight gain. (Initially, fluid within the patient is redistributed to lungs, meaning that in the early stages of decompensation the patient may exhibit no weight gain, even though fluid has begun to accumulate in the lungs). Patient weight is also subject to influences other than the accumulation of thoracic fluid. A patient exhibiting both a decrease in thoracic impedance and a weight gain are may be more reliably identified as being likely to experience imminent decompensation of heart failure. Thus, any of the devices of FIG. 41 may be programmed to look for both conditions, and to generate an alert when both conditions are present. On the other hand, an alert may be generated when only a single measurement indicates the possibility of decompensation (e.g., only impedance is depressed, or only weight is elevated), but the patient's answers to the questions indicate symptoms consistent with decompensation. Thus, any of the devices of FIG. 41 may be programmed to identify an abnormal impedance or weight combined with answers consistent with decompensation, and to generate an alert when both conditions are present.

Other combinations of data may be observed by any of the devices of FIG. 41 to determine decompensation. For example, it is known that atrial fibrillation may be transitory (may last for only a few hours or a few days). If the atrial fibrillation is sufficiently short-lived, the patient may exhibit no weight gain, even though the heart is decompensating. However, the device may communicate the occurrence of an event marker indicating the beginning of atrial fibrillation to the patient monitoring apparatus. The patient monitoring apparatus may also interrogate the device to obtain the transthoracic impedance exhibited by the patient. A decrease in impedance, combined with an atrial fibrillation marker may indicate that the patient is decompensating, and that the patient should be seen. Thus, any of the devices of FIG. 41 may be programmed to look for both conditions, and to generate an alert when both conditions are present. Further, the patient monitoring apparatus may seek to verify its conclusions by identifying patients with answers consistent with decompensation. Therefore, any of the devices of FIG. 41 may be programmed to identify occurrences of atrial fibrillation markers, depressed transthoracic impedance, and patient answers consistent with decompensation, and to generate an alert when these conditions are present.

Acute coronary syndrome may be determinable from the combined data sets of the device and the patient monitoring apparatus. For example, the patient monitoring apparatus may interrogate the device to obtain recently stored records of heart sounds. The frequency/amplitude/shape information within the heart sound data may be analyzed to determine that a wall within the heart does not appear to be moving. Such a conclusion, combined with patient answers consistent with acute coronary syndrome may be identified by any of the devices in FIG. 41, and an alert may be generated in response to their occurrence.

Aspects of the invention described as being carried out by a computing system or are otherwise described as a method of control or manipulation of data may be implemented in one or a combination of hardware, firmware, and software. Embodiments of the invention may also be implemented as instructions stored on a machine-readable medium, which may be read and executed by at least one processor to perform the operations described herein. A machine-readable medium may include any mechanism for storing or transmitting information in a form readable by a machine (e.g., a computer). For example, a machine-readable medium may include read-only memory (ROM), random-access memory (RAM), magnetic disc storage media, optical storage media, flash-memory devices, electrical, optical, acoustical or other form of propagated signals (e.g., carrier waves, infrared signals, digital signals, etc.), and others.

The Abstract is provided to comply with 37 C.F.R. Section 1.72(b) requiring an abstract that will allow the reader to ascertain the nature and gist of the technical disclosure. It is submitted with the understanding that it will not be used to limit or interpret the scope or meaning of the claims.

In the foregoing detailed description, various features are occasionally grouped together in a single embodiment for the purpose of streamlining the disclosure. This method of disclosure is not to be interpreted as reflecting an intention that the claimed embodiments of the subject matter require more features than are expressly recited in each claim. Rather, as the following claims reflect, inventive subject matter lies in less than all features of a single disclosed embodiment. Thus, the following claims are hereby incorporated into the detailed description, with each claim standing on its own as a separate preferred embodiment. Therefore, the spirit and scope of the appended claims should not be limited to the description of the preferred versions contained herein.

The claimed invention is:

1. A computer-implemented method of detecting an impending decompensation of heart failure in a patient, the method comprising:
   receiving, at a computer, transthoracic impedance data measured by a cardiac rhythm management device implanted in the patient, wherein the cardiac rhythm management device measures the transthoracic impedance data while the patient is standing on a scale;
   obtaining, at the computer, a weight measurement, the weight measurement indicating a weight of the patient, the computer obtaining the weight measurement from the scale, the scale measuring the weight of the patient while the patient is standing on the scale; and
   receiving, at the computer, answers provided by the patient to one or more questions posed to the patient;
   detecting, at the computer, impending decompensation of acute heart failure, based at least in part upon the weight measurement, the answers and the transthoracic impedance data received from the cardiac rhythm management device,
   wherein the act of detecting impending decompensation of heart failure comprises generating a score based at least in part upon the answers provided by the patient or the weight measurement and comparing the score to a threshold.

2. The method of claim 1, further comprising generating an alert when impending decompensation of acute heart failure is detected.

3. The method of claim 2, further comprising communicating the alert to a health care provider.

4. The method of claim 1, wherein the cardiac rhythm management device is a pacemaker.

5. A computer-implemented method of detecting impending decompensation of heart failure in a patient, the method comprising:
   receiving, at a computer, transthoracic impedance data measured by a cardiac rhythm management device implanted in the patient, the cardiac rhythm management device measuring the transthoracic impedance data in response to detecting a rhythm abnormality in the patient's heart;
   posing one or more questions to the patient with the computer;
   receiving, at the computer, answers to the one or more questions;
   obtaining, at the computer, a weight measurement of the patient; and
   detecting, at the computer, impending decompensation of heart failure, based at least in part upon the answers, the weight measurement and the transthoracic impedance data received from the cardiac rhythm management device
   wherein the act of detecting impending decompensation of heart failure comprises:
      generating, at the computer, a score based at least in part upon the answers or the weight measurement; and
      comparing the score to a threshold.

6. The method of claim 5, further comprising generating an alert when impending decompensation of heart failure is detected.

7. The method of claim 6, further comprising communicating the alert to a health care provider.

8. The method of claim 5, wherein the cardiac rhythm management device is a pacemaker.

9. A computer-implemented method of detecting impending decompensation of heart failure in a patient, the method comprising:
   receiving, with a processor device external to the patient, transthoracic impedance data measured by a cardiac rhythm management device implanted in the patient, the cardiac rhythm management device measuring the transthoracic impedance data in response to detecting a rhythm abnormality in the patient's heart;
   measuring a physiological parameter of the patient;
   communicating the physiological parameter to the processor device;
   receiving, with the processor device, answers to one or more questions posed to the patient; and
   detecting, with the processor device, impending decompensation of heart failure, based at least in part upon a comparison between a score and a threshold, the processing device generating the score based upon the transthoracic impedance data, the answers and the physiological parameter.

10. The method of claim 9, further comprising communicating the physiological parameter, the answers, and the transthoracic impedance data to a remote computer.

11. The method of claim 9, further comprising generating an alert when impending decompensation of heart failure is detected.

12. The method of claim 11, further comprising communicating the alert to a health care provider.

13. The method of claim 9, wherein the cardiac rhythm management device is a pacemaker.

* * * * *